US011091556B2

(12) United States Patent
Morsey et al.

(10) Patent No.: US 11,091,556 B2
(45) Date of Patent: Aug. 17, 2021

(54) CANINIZED HUMAN ANTIBODIES TO HUMAN IL-4R ALPHA

(71) Applicant: Intervet Inc., Madison, NJ (US)

(72) Inventors: Mohamad Morsey, Omaha, NE (US); Yuanzheng Zhang, Edison, NJ (US)

(73) Assignee: Intervet Inc., Madison, NJ (US)

( * ) Notice: Subject to any disclaimer, the term of this patent is extended or adjusted under 35 U.S.C. 154(b) by 323 days.

(21) Appl. No.: 16/061,712

(22) PCT Filed: Dec. 15, 2016

(86) PCT No.: PCT/EP2016/081138
§ 371 (c)(1),
(2) Date: Jun. 13, 2018

(87) PCT Pub. No.: WO2017/102920
PCT Pub. Date: Jun. 22, 2017

(65) Prior Publication Data
US 2018/0371097 A1 Dec. 27, 2018

Related U.S. Application Data

(60) Provisional application No. 62/401,368, filed on Sep. 29, 2016, provisional application No. 62/469,486, filed on Dec. 18, 2015.

(51) Int. Cl.
*C07K 16/24* (2006.01)
*C07K 16/28* (2006.01)
*A61P 17/00* (2006.01)

(52) U.S. Cl.
CPC .......... *C07K 16/2866* (2013.01); *A61P 17/00* (2018.01); *C07K 2317/21* (2013.01); *C07K 2317/24* (2013.01); *C07K 2317/33* (2013.01); *C07K 2317/34* (2013.01); *C07K 2317/524* (2013.01); *C07K 2317/526* (2013.01); *C07K 2317/53* (2013.01); *C07K 2317/71* (2013.01); *C07K 2317/73* (2013.01); *C07K 2317/732* (2013.01); *C07K 2317/76* (2013.01)

(58) Field of Classification Search
None
See application file for complete search history.

(56) References Cited

U.S. PATENT DOCUMENTS

| 6,005,079 | A | 12/1999 | Casterman et al. |
|---|---|---|---|
| 6,703,360 | B2 | 3/2004 | McCall et al. |
| 6,808,710 | B1 | 10/2004 | Wood et al. |
| 6,936,704 | B1 | 8/2005 | Freeman et al. |
| 7,038,013 | B2 | 5/2006 | Freeman et al. |
| 7,101,550 | B2 | 9/2006 | Wood et al. |
| 7,105,328 | B2 | 9/2006 | Wood et al. |
| 7,186,809 | B2 | 3/2007 | Pluenneke |
| 7,208,579 | B2 | 4/2007 | Watson et al. |
| 7,261,890 | B2 | 8/2007 | Krah, III et al. |
| 7,432,059 | B2 | 10/2008 | Freeman et al. |
| 7,595,048 | B2 | 9/2009 | Honjo et al. |
| 7,635,757 | B2 | 12/2009 | Freeman et al. |
| 7,638,492 | B2 | 12/2009 | Wood et al. |
| 7,700,301 | B2 | 4/2010 | Wood et al. |
| 7,709,214 | B2 | 5/2010 | Freeman et al. |
| 7,722,868 | B2 | 5/2010 | Freeman et al. |
| 7,807,158 | B2 | 10/2010 | Endl et al. |
| 8,008,449 | B2 | 8/2011 | Korman et al. |
| 8,337,842 | B2 | 12/2012 | Hansen |
| 8,354,509 | B2 | 1/2013 | Carven et al. |
| 8,569,460 | B2 | 10/2013 | Hansen |
| 8,652,470 | B2 | 2/2014 | Hansen |
| 8,735,553 | B1 | 5/2014 | Li et al. |
| 8,791,242 | B2 | 7/2014 | Mattson et al. |
| 8,877,189 | B2 | 11/2014 | Eriksson et al. |
| 9,067,999 | B1 | 6/2015 | Honjo et al. |
| 9,580,496 | B2 | 2/2017 | Gearing |
| 9,616,120 | B2 | 4/2017 | Hansen |
| 9,790,280 | B2 | 10/2017 | Rue et al. |
| 2002/0165135 | A1 | 11/2002 | McCall et al. |
| 2007/0003546 | A1 | 1/2007 | Lazar et al. |
| 2007/0037210 | A1 | 2/2007 | Chemtob et al. |
| 2007/0148164 | A1 | 6/2007 | Farrington et al. |
| 2010/0266617 | A1 | 10/2010 | Carven et al. |
| 2011/0318373 | A1 | 12/2011 | Sasikumar et al. |
| 2012/0039906 | A1 | 2/2012 | Olive |
| 2014/0356372 | A1 | 12/2014 | Stahl et al. |
| 2015/0017176 | A1 | 1/2015 | Kostic et al. |
| 2016/0311902 | A1 | 10/2016 | Morsey et al. |
| 2016/0333096 | A1 | 11/2016 | Morsey et al. |

FOREIGN PATENT DOCUMENTS

| EP | 1537878 B1 | 6/2005 |
|---|---|---|
| EP | 1836226 B1 | 6/2011 |
| EP | 2705057 B1 | 3/2016 |

(Continued)

OTHER PUBLICATIONS

Paul (1993) Fundamental Immunology, #rd edition, pp. 292-295.*
Bendig (1995) Methods: a companion. Methods in Enzymology 8: 83-93.*
MacCallum et al. (1996) J. Mol. Biol. 262: 732-745.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Skolnick and Fetrow. From genes to protein structure and function: novel applications of computational approaches in the genomic era. Trends in Biotechnology, 2000. vol. 18, pp. 34-39.*

(Continued)

*Primary Examiner* — Michael D Pak
(74) *Attorney, Agent, or Firm* — Michael D. Davis

(57) ABSTRACT

The present invention provides caninized human anti-human IL-4Rα antibodies that have specific sequences and a high binding affinity for canine IL-4Rα. The invention also relates to use of these antibodies in the treatment of dogs against atopic dermatitis.

10 Claims, 5 Drawing Sheets

Specification includes a Sequence Listing.

(56) References Cited

FOREIGN PATENT DOCUMENTS

| JP | 2014140982 | | 1/2016 |
|---|---|---|---|
| WO | 9404678 | A1 | 3/1994 |
| WO | 9425591 | A1 | 11/1994 |
| WO | 1999051642 | A1 | 10/1999 |
| WO | 2003042402 | A2 | 5/2003 |
| WO | 2003060080 | A2 | 7/2003 |
| WO | 2005032399 | A2 | 4/2005 |
| WO | 2008083174 | A2 | 7/2008 |
| WO | 2008156712 | A1 | 12/2008 |
| WO | 2010070346 | A2 | 6/2010 |
| WO | 2010110838 | A2 | 9/2010 |
| WO | 2010117448 | A2 | 10/2010 |
| WO | 2010117760 | A2 | 10/2010 |
| WO | 2012135408 | A1 | 10/2012 |
| WO | 2012153121 | A1 | 11/2012 |
| WO | 2012153122 | A1 | 11/2012 |
| WO | 2012153123 | A1 | 11/2012 |
| WO | 2012153126 | A1 | 11/2012 |
| WO | 2013030568 | A1 | 3/2013 |
| WO | 2013034900 | A1 | 3/2013 |
| WO | 2013063186 | A2 | 5/2013 |
| WO | 2013124666 | A1 | 8/2013 |
| WO | 2014197470 | A1 | 12/2014 |
| WO | 2015091910 | A2 | 6/2015 |
| WO | 2015091911 | A2 | 6/2015 |
| WO | 2015091914 | A2 | 6/2015 |
| WO | 2016050721 | A1 | 9/2015 |
| WO | 2016006241 | A1 | 1/2016 |
| WO | 2016156588 | A1 | 10/2016 |

OTHER PUBLICATIONS

Wu, Nie, Huse, and Watkins. Humanization of a murine monoclonal antibody by simultaneous optimization of framework and CDR residues. Journal of Molecular Biology, 1999. vol. 294, pp. 151-162.*
Al-Lazikani, Standard Conformations for the Canonical Structures of Immunoglobulins, J. Mol. Biol., 1997, 927-948, 273.
Alegre, A non-activating "humanized" anti-CD3 monoclonal antibody retains immunosuppressive properties in vivo, Transplantation, 1994, 1537-1543, 57.
Amgen vs. Sanofi and Regeneron, Case 17-1480, Document 176, filed Feb. 6, 2018, United States Court of Appeals for the Federal Circuit, Response to Petition for Rehearing En Banc, 27 pages.
Atherton, MJ et al., Cancer immunology and canine malignant melanoma: A comparative review, Veterinary Immunology and Immunopathology, 2016, pp. 15-26, 169.
Barber et al., Restoring function in exhausted CD8 T cells during chronic viral infection, Nature, 2006, pp. 682-687, vol. 439.
Baudino et al., Crucial Role of aspartic acid at position 265 in the CH2 domain for muri e IgG2a and IgG2b Fc-assiciated effector functions, J. Immunology, 2008, pp. 6664-6669, vol. 181.
Bendig, Mary E., humanization of Rodent Monoclonal Antibodies by CDR Grafting, Methods: A companion to methods in Enzymology, 1993, 83-93, 8.
Bergeron et al., Comparative functional characterization of canine IgG subclasses, Veterinary Immunology and Immunopathology, 2014, pp. 31-41, 157, WO.
Berglund, L et al., The epitope space of the human proteome, Protein Science, 2008, pp. 606-613, 17.
Brown, Blockade of Programmed Death-1 Ligands on Dendritic Cells Enhances T Cell Activation and Cytokine Production, J. Immunol., 2003, pp. 1257-1266, vol. 170.
Chan et al., Therapeutic antibodies for autoimmunity and inflammation, The Journal of Immunology, 2010, pp. 301-316, 10-5, WO.
Chothia et al, Canonical Structures for the Hypervariable Regions of Immunoglobins, J. Mol. Biol., 1987, 901-917, 196.
Chothia et al., Conformations of immunoglobin hypervariable regions, Nature, 1989, 877-883, 342.

Cobbold, et al., The immunology of companion animals: reagents and therapeutic strategies with potential veterinary and human clinical applications, Immunology Today, 1994, pp. 347-353, 15-8.
Colman, Effects of amino acid sequence changes on antibody-antigen interactions, Research Immunology, 1994, 33-36, 145.
Dong et al., Tumor-associated B7-H1 promotes T-cell apoptosis: A potential mechanism of immune evasion, Nature Medicine, 2002, pp. 793-800, vol. 8(8).
Dorai, H et al., Aglycosylated chimeric mouse/human IgG1 antibody retains some effector function, Hybridoma, 1991, pp. 211-217, 10(2).
Esch, et al., Programmed Death 1-Mediated T Cell Exhaustion during Visceral Leishmaniasis Impairs Phagocyte Functioni, The Journal of Immunology, 2013, pp. 5542-5550, 191, WO.
Galizzi et al., Molucular cloning of a cDNA encoding the human interleukin 4 receptor, International Immunology, 1990, 669-675, 2(7).
Gearing, DP et al., A fully caninised anti-NGF monoclonal antibody for pain relief in dogs, BMC Veterinary Research, 2013, pp. 1-11, vol. 9 (226), WO.
Geczy, T et. al., Molecular basis for failure of "Atypical" C1 domain of Vav1 to bind diacylglycerol/phorbol ester, The Journal of Biological Chemistry, 2012, pp. 13137-13158, 287(16).
GenBank accession No. AAL35301.1, amino acid sequence of IgGA heavy chain, 1 page.
GenBank accession No. AAL35302.1, amino acid sequence of IgGB heavy chain, 1 page.
GenBank accession No. AAL35303.1, amino acid sequence of IgGC heavy chain, 1 page.
GenBank accession No. AAL35304.1, amino acid sequence of IgGD heavy chain, 1 page.
GenBank accession No. ABY55569.1, lambda light chain amino acid sequence, 1 page.
GenBank accession No. ABY57289.1, kappa light chain amino acid sequence, 1 page.
GenBank accession No. NP000409.1, mature predicted canine IL-4 receptor alpha chain protein sequence shares 65% identity with human IL-4 receptor alpha chain, 1 page.
GenBank accession No. NP999505.1, mature predicted canine IL-4 receptor alpha chain protein sequence shares 70% identity with swine IL-4 receptor alpha chain, 1 page.
GenBank accession No. XP54077.3, an 823 amino acids, including a 25 amino acid leader sequence, 1 page.
GenBank accession XM547077.4, Full length canine IL-4 receptor alpha chain sequence, 1 page.
Harskamp et al., Immunology of Atopic Dermatitis: Novel Insights into Mechanisms and Immunomodulatory Therapies, Seminars in Cutaneous Medicine and Surgery, 2013, 132-139, 32.
Hutchins, Improved bio distribution, tumor targeting and reduced immunogenicity in mice with a gamma 4 variant of CAMPATH-1H, Proc. Natl. Acad. Sci. USA, 1995, pp. 11980-11984, 92.
Ikebuchi et al., Blockade of bovine PD-1 increases T cell funtion and inhibits bovine leukemia virus expression in B cells in vitro, Veterinary Research, 2013, 1-15, 44-59.
International Search Report for PCT/EP2015/081138 dated May 4, 2017, 22 pages.
Iwai, Involvement of PD-L1 on tumor cells in the escape from host immune system and tumor immunotherapy by PD-L1 blockade, Proc. Natl. Acad. Sci. USA, 2002, pp. 12293-12297, vol. 99.
Jackson, et al., In Vitro Antibody Maturation, Improvement of a High Affinity, Neutralizing Antibody Against IL-1Beta, The Journal of Immunology, 1995, pp. 3310-3319, 154, WO.
Kabat, The Structural Basis of Antibody Complementarity, Adv. Prot. Chem., 1978, 1-75, 32.
Kabat, Unusual Distributions of Amino Acids in Complementarity-determining (Hypervriable) Segment of Heavy and Light Chains of Immunoglobulins and Their Possible Roles in Specificity of Antibody-combining Sites, J. Biol. Chem., 1977, 6609-6616, 252.
Khantasup, K et al., Design and generation of humanized single-chain Fv derived from mouse hybridoma for potential targeting application, Monoclonal antibodies, 2015, pp. 404-417, 34(6).

(56) References Cited

OTHER PUBLICATIONS

Lin, The PD-1/PD-L1 complex resembles the antigen-binding Fv domains of antibodies and T cell receptors, Proc. Natl. Acad. Sci. USA, 2008, pp. 3011-3016, vol. 105.
Lund et al., J. Immunol., J. Immunol., 1996, pp. 4963-4969, 157.
Lyford-Pike, et al., Evidence for a Role of the PD-1:PD-L1 Pathway in Immune Resistance of HPV-Associated Head and Neck Squamous Cell Carcinoma, Cancer Research, 2012, pp. 1733-1741, 73-6, WO.
Malajian et al., New pathogenic and therapeutic paradigms in atopic dermatitis, Cytokine, 2015, 311-318, 73.
McDermott, et al., PD-1 as a potential target in cancer therapy, Cancer Medicine, 2013, pp. 662-673, WO.
McEarchern, Engineered anti-CD70 antibody with multiple effector functions exhibits in vitro and in vivo antitumor activities, Blood, 2007, 1185-1192, 109.
Mimura, Y et al., Glycosylation engineering of therapeutic IgG antibodies: challenges for the safety, functionality and efficacy, Protein Cell, 2018, pp. 47-62, 9(1).
Minty et al., Interleukin-13 is a new human lymphokine regulating inflammatory and immune responses, Nature, 1993, 248-250, 362.
Mosley et al., The Murine Interleukin-4 Receptor: Molecular Cloning and Characterization of Secreted and Membrane Bound Forms, Cell, 1989, 335-348, 59(2).
Muyldermans, Recognition of antigens by single-domain antibody fragments: the superfluous luxury of paired domains, Trends Biochem. Sci., 2001, 230-235, 26.
National Service Foundation Award Abstract #1262435, ABI Innovation: Predicting the combined impact of multiple mutations on protein functional adaptation, 2012, 2 pages.
NCBI Reference Sequence: XP_543338.3, Sep. 24, 2013, XP055179334, retrieved from Internet: URL:http://www.ncbi.nlm.nih.gov/protein/XP_543338.
Nomi et al., Clinical Significance and Therapeutic Potential of the Programmed Death-1 Ligand/Programmed Death-1 Pathway in Human Pancreatic Cancer, Clinical Cancer Research, 2007, pp. 2151-2157, vol. 13.
Nuttall et al., Canine Atopic Dermatitis—what have we learned?, Veterinary Record, 2013, 201-207, 172(8).
Okazaki, PD-1 and PD-1 ligands: from discovery to clinical application, Int. Immunol., 2007, pp. 813-824, vol. 19.
Paul, WE, Fundamental Immunology, Fundamental Immunolgy, third edition, 1993, 292-295, Third Edition.
Rahman et al., The Pathology and Immunology of Atopic Dermatitis, Inflammation & Allergy—Drug Targets, 2011, 486-496, 10.
Regeneron Pharmaceuticals, Inc., Sanofi and Regeneron Report Positive Proof-of-Concept Data for Dupilumab, an IL-4R alpha Antibody, in Atopic Dermatitis, 71st Annual Meeting of the American Academy of Dermatology, Mar. 2, 2013, pp. 1-3, XP007922251.
Reichmann, Single domain antibodies: comparison of camel VH and camelised human VH domains, J. Immunol. Methods, 1999, 25-38, 231.
Roguin, LP et al., Monoclonal antibodies inducing conformational changes on the antigen molecule, Scandinaavian Journal of Immunology, 2003, pp. 387-394, 58.
Rudikoff, S et al., Single amino acid substitution altering antigen-binding specificity, PNAS, 1982, pp. 1979-1983, 79.
Sazinsky, Aglycosylated immunoglobin G1 variants productively engage activating Fc receptors, Proc. Natl. Acad. Sci., 2008, 20167-20172, 105.
Shields, High Resolution Mapping of the Binding Site on Human IgG1 for FcγRI, FcγRII, FcγRIII, and FcRn and Design of IgG1 Variants with Improved Binding to the FeyR, J. of Biol. Chem., 2001, 6591-6604, 276-9.
Strome et al., B7-H1 Blockade Augments Adoptive T-Cell Immunotherapy for Squamous Cell Cancinoma, Cancer Research, 2003, pp. 6501-6505, vol. 63.
Tang et al., Cloning and characterization of cDNAs encoding four different canine immunoglobulin Y chains, Veterinary Immunology and Immunopathology, 2001, pp. 259-270, 80.
Tao, MH et al., Role of carbohydrate in the structure and effector functions mediated by the human IgG constant region, The Journal of Immunology, 1989, pp. 2595-2601, 143(8).
Thompson et al., PD-1 Is Expressed by Tumor-Infiltrating Immune Cells and Is Associated with Poor Outcome for Patients with Renal Cell Carcinoma, Clinical Cancer Research, 2007, pp. 1757-1761, vol. 15.
Thompson et al., Tumor B7-H1 Is Associated with Poor Prognosis in Renal Cell Carcinoma Patients with Long-Term Follow-up, Cancer Res., 2006, pp. 3381-3385, vol. 66.
Tsushima et al., Predominant expression of B7-H1 and its immunoregulatory roles in oral squamous cell carcinoma, Oral Oncol., 2006, pp. 268-274, vol. 42.
Tzartos, SJ, Epitope mapping by antibody competition, Methods in Molecular Biology, 1996, pp. 55-66, 66.
Van Der Kaaij et al., Molecular cloning and sequencing of the cDNA for dog interleukin-4, Immunogenetics, 1999, 142-143, 49.
Vatrella, Dupilumab: a novel treatement for asthma, Jornal of Asthma and Allergy, 2014, 123-130, 7.
Wintterle et al., Expression of the B7-Related Molecule B7-H1 by Glioma Cells: A Potential Mechanism of Immune Paralysis, Cancer Res., 2003, pp. 7462-7467, vol. 63.
Wong, et al, Structural Requirements for a Specificity Switch and for Maintenance of Affinity Using Mutational Analysis of a Phage-Displayed Anti-Arsonate Antibody of Fab Heavy Chain First Complementarity-Determining Region, Journal of Immunology, 1998, pp. 5990-5997, 160, WO.
Yang et al, Canine Interleukin-13: Molecular Cloning of Full-Length cDNA and Expression of Biologically Active Recombinant Protein, Journal of Interferon and Cytokine Research, 2000, 779-785, 20.
Yokota et al., Isolation and characterization of a human interleukin cDNA clone, homologous to mouse B-cell stimulatory factor 1, that expresses B-cell- and T-cell-stimulating activities, Proc. Natl. Acad. Sci. USA, 1986, 5894-5898, 83.
Zhang et al., Structural and Functional Analysis of the Costimulatory Receptor Programmed Death-1, Immunity, 2004, pp. 337-347, vol. 20.

* cited by examiner

CANINIZED HUMAN ANTIBODIES TO HUMAN IL-4R ALPHA

CROSS-REFERENCE TO RELATED APPLICATIONS

This application is a national stage entry under 35 U.S.C. § 371 of PCT/EP2016/081138 filed on Dec. 15, 2016, which claims priority to U.S. 62/401,368 filed on Sep. 29, 2016 and U.S. 62/269,486 filed on Dec. 18, 2015, the contents of which are hereby incorporated by reference in their entireties.

FIELD OF THE INVENTION

The present invention relates to caninized human antibodies to human IL-4Rα that have specific sequences and a high binding affinity for canine IL-4Rα. The invention also relates to use of the antibodies of the present invention in the treatment of atopic dermatitis in dogs.

BACKGROUND OF THE INVENTION

The immune system comprises a network of resident and recirculating specialized cells that function collaboratively to protect the host against infectious diseases and cancer. The ability of the immune system to perform this function depends to a large extent on the biological activities of a group of proteins secreted by leukocytes and collectively referred to as interleukins. Among the well-studied interleukins are two important molecules identified as interleukin-4 (IL-4) and interleukin-13 (IL-13). IL-4 and IL-13 are two closely related proteins that can be secreted by many cell types including CD4$^+$ Th2 cells, natural killer T cells (NKT), macrophages, mast cells, and basophils. IL-4 and IL-13 display many overlapping functions and are critical to the development of T cell-dependent humoral immune responses. Despite their similarities in overall structure, cell sources and biological functions, each of these cytokines mediates certain specialized functions, which has stimulated considerable research aimed at identifying the receptors and the downstream signaling pathways through which these interleukins mediate both their common and unique biological activities.

It is now known that IL-4 binds with high affinity to two receptors i.e., type-I and type-II IL-4 receptors. The type I IL-4 receptor consists of the IL-4 receptor α chain and the common γ C chain, which is also part of the receptor for several other interleukins including IL-2, IL-7, IL-9, and IL-15. The Type II IL-4 receptor consists of the IL-4 receptor α chain and the IL-13 receptor α1 chain. On the other hand, IL-13 binds to the type-II IL-4 receptor, and to a unique receptor designated IL-13 receptor α2. The binding of IL-13 to the IL-13 receptor α2 does not transduce a signal and this receptor is also secreted in a soluble form. Accordingly the IL-13 receptor α2 has often been referred to as a decoy receptor.

The genes encoding the IL-4 protein from various species have been cloned and expressed in bacterial and mammalian cells. For example, the cDNA encoding human IL-4 shows that the mature human IL-4 is a secreted polypeptide of 129 amino acids with a predicted molecular weight of 15 Kd [Yokota et al., *Proc Natl Acad Sci USA*. 83(16): 5894-5898 (1986)]. The cDNA encoding the canine IL-4 protein has also been identified and shown to encode a 132 amino acid polypeptide that shares 40% identity with human IL-4 [van der Kaaij et al., *Immunogenetics* 49:142-143(1999)]. The gene encoding human IL-13 has been cloned and expressed in a variety of host systems [Minty et al., *Nature* 362:248-50 (1993)]. A cDNA encoding human IL-13 shows that the mature IL-13 is a secreted polypeptide with a 12.4 Kd apparent molecular weight. A cDNA encoding canine IL-13 also has been identified [Yang et al., *J. Interferon and Cytokine Research* 20:779-785 (2000)]. The predicted canine IL-13 mature polypeptide consists of 111 amino acids and shares 61.8% identity with human IL-13.

The genes encoding the human and mouse IL-4 receptor α chains have been cloned and expressed in a variety of host systems. For example, the cDNA encoding the human IL-4 receptor α chain has been described by Galizzi et al., [*International Immunology* 2(7):669-675 (1990)] and the cDNA encoding the murine IL-4 receptor α chain has been described by Mosley et al., [*Cell*, 59(2):335-348 (1989)]. The cDNA for human IL-4 receptor α chain encodes for 825 amino acid residues including a 24 amino acid residue signal sequence. The murine protein is 15 amino acid residues shorter than the human receptor and has an overall sequence identity of 50% at the amino acid level.

Genes encoding equine, canine, and feline IL-4 receptor α chains have also been disclosed [see, U.S. Pat. No. 7,208,579 B2]. In addition, a cDNA predicted to be corresponding to one isoform of canine IL-4 receptor α can be found in Genbank database (SEQ ID NO: 1). The present invention therefore undertook to determine the IL-4 receptor α chain cDNA and to definitively determine its encoded polypeptide sequence.

Although IL-4 and IL-13 are critical cytokines for the development of Th2 immune responses that are required for protection against extracellular pathogens (e.g., tissue or lumen dwelling parasites), both cytokines have been implicated in the pathogenesis of a variety of allergic diseases in humans and animals, including asthma and atopic dermatitis. Asthma is a common respiratory disease in humans. The disease is characterized by lung inflammation, hyper-responsiveness of bronchial airways to external stimuli, and structural modifications of the bronchial wall tissues. The pathophysiology of allergic asthma has been reviewed by Vatrella et al., [*Journal of Asthma and Allergy* 7:123-130 (2014)]. Asthma is sustained by CD4$^+$ Th2 cells which produce large amounts of IL-4 and IL-13 and orchestrate the immune inflammatory response in the allergic airways. Recent progress in understanding the asthmatic response highlights the important roles played by both IL-4 and IL-13 in the disease pathogenesis. For example, both cytokines stimulate immunoglobulin isotype switch in B cells from IgM to IgE, and this allergen-specific IgE contribute to mast cell degranulation and release of inflammatory mediators in the airways. In addition, both IL-4 and IL-13 increase bronchial smooth muscle contraction and stimulate airway recruitment of eosinophils which can also degranulate in response to crosslinking of allergen-bound IgE to its receptor on eosinophils. In addition, IL-13 also stimulates mucus secretion and promotes airway remodeling by stimulating goblet cell hyperplasia, deposition of collagen, and proliferation of airway smooth muscle cells. Thus it is now clear that IL-4 and IL-13 are intimately involved in the pathological changes that lead to expression of asthmatic episodes including bronchial constriction and increased airway hyperactivity.

Atopic dermatitis (AD) is a relapsing pruritic inflammatory skin disease that is characterized by immune system dysregulation and epidermal barrier abnormalities. The pathological and immunological attributes of AD have been the subject of extensive investigations [reviewed in Rahman et al. *Inflammation & Allergy-drug target* 10:486-496 (2011) and Harskamp et al., *Seminar in Cutaneous Medicine and Surgery* 32:132-139 (2013)]. AD is the most common skin disease in man affecting 2-10% of the adult population in the United States and about 25% of children worldwide. In man, AD skin lesions are characterized by infiltrations with Th2 cells, eosinophils, mast cells and dendritic cells. In the acute phase of AD, these lesions display a predominant expression of Th2-type cytokines including IL-4 and IL-13. AD is also characterized by elevated circulating levels of IgE and is positively correlated with IL-4 and IL-13 expression in CD4+ Th2 cells in the skin. Although AD has been classified as a Th2 disease, other T cell subsets such as Th1, Th22, and Th17 might also contribute to disease pathogenesis. Despite the increasing incidence of AD worldwide, treatment options available to patients whose symptoms are not adequately controlled by topical agents are limited to oral corticosteroids, oral cyclosporine, and narrow band UVB phototherapy. These therapies are not always effective and their use is associated with a variety of safety effects. Recently, human monoclonal antibodies specific to human IL-4Rα have been generated from transgenic mice that had been manipulated to have a humanized immune system and some of these antibodies have been tested extensively for their therapeutic utilities in man for treatment of atopic dermatitis [see e.g., US 20150017176 A1].

Atopic dermatitis is also a common disease in companion animals, especially dogs, where its prevalence has been estimated to be approximately 10-15% of the canine population. The pathogenesis of AD in dogs and cats [reviewed in Nuttall et al., *Veterinary Records* 172(8):201-207 (2013)] bears significant similarities to that of AD in man, including skin infiltration by a variety of immune cells and CD4 Th2 polarized cytokine milieu including preponderance of IL-4 and IL-13 cytokines. As in humans, current therapies for atopic dermatitis in dogs and cats rely on palliative therapy such as shampoos and moisturizers or symptomatic therapy via the use of oral or systemic corticosteroids and oral cyclosporine. As with human AD, these therapies do not address the underlying mechanism of disease and have significant safety and efficacy issues. Thus, there is an unmet medical need for a safe and effective treatment option for AD in companion animals. Such treatment should preferably interfere with the underlying mechanism of disease.

The citation of any reference herein should not be construed as an admission that such reference is available as "prior art" to the instant application.

SUMMARY OF THE INVENTION

The present invention relates to caninized human[1] anti-human IL-4R alpha antibodies that have a high binding affinity to canine IL-4Rα, as well as having the ability to block the binding of canine IL-4Rα to canine IL-4 and/or IL-13. The present invention also relates to use of such antibodies in the treatment of disease and/or conditions such as atopic dermatitis.

[1] i.e., generated from transgenic mice that had been manipulated to have a humanized immune system.

Accordingly, the present invention provides an isolated caninized antibody or antigen binding fragment thereof that specifically binds interleukin-4 receptor alpha (IL-4Rα) comprising a canine IgG heavy chain and a canine kappa or lambda light chain. In particular embodiments of this type, the canine kappa or lambda light chain that comprises three light chain complementary determining regions (CDRs): CDR light 1 (CDRL1), CDR light 2 (CDRL2), and CDR light 3 (CDRL3); and the canine IgG heavy chain comprises three heavy chain CDRs: CDR heavy 1 (CDRH1), CDR heavy 2 (CDRH2) and CDR heavy 3 (CDRH3) obtained from a mammalian IL-4Rα antibody. Particular embodiments of the caninized antibodies and fragments thereof of the present invention bind canine IL-4Rα and/or block the binding of canine IL-4Rα to canine Interleukin-4 (IL-4).

In certain embodiments, the canine light chain is a kappa chain. In particular embodiments of this type, the CDRL1 comprises the amino acid sequence of SEQ ID NO: 43. In related embodiments the CDRL1 comprises a conservatively modified variant of SEQ ID NO: 43. In other embodiments, the CDRL2 comprises the amino acid sequence comprising SEQ ID NO: 44. In related embodiments the CDRL2 comprises a conservatively modified variant of SEQ ID NO: 44. In still other embodiments the CDRL3 comprises the amino acid sequence of SEQ ID NO: 45. In related embodiments the CDRL3 comprises a conservatively modified variant of SEQ ID NO: 45. In yet other embodiments, the CDRH1 of the canine IgG heavy chain comprises the amino acid sequence of SEQ ID NO: 46. In related embodiments the CDRH1 comprises a conservatively modified variant of of SEQ ID NO: 46. In still other embodiments the CDRH2 comprises the amino acid sequence of SEQ ID NO: 47. In related embodiments the CDRH2 comprises a conservatively modified variant of SEQ ID NO: 47. In yet other embodiments the CDRH3 comprises the amino acid sequence of SEQ ID NO: 48. In related embodiments the CDRH3 comprises a conservatively modified variant of SEQ ID NO: 48.

In specific embodiments the CDRL1 comprises the amino acid sequence of SEQ ID NO: 43 or a conservatively modified variant of SEQ ID NO: 43, the CDRL2 comprises the amino acid sequence comprising SEQ ID NO: 44 or a conservatively modified variant of SEQ ID NO: 44, and the CDRL3 comprises the amino acid sequence of SEQ ID NO: 45 or a conservatively modified variant of SEQ ID NO: 45.

In other specific embodiments the CDRH1 comprises the amino acid sequence of SEQ ID NO: 46 or a conservatively modified variant of SEQ ID NO: 46, the CDRH2 comprises the amino acid sequence comprising SEQ ID NO: 47 or a conservatively modified variant of SEQ ID NO: 47, and the CDRH3 comprises the amino acid sequence of SEQ ID NO: 48 or a conservatively modified variant of SEQ ID NO: 48.

In a more specific embodiment the CDRL1 comprises the amino acid sequence of SEQ ID NO: 43 or a conservatively modified variant of SEQ ID NO: 43, the CDRL2 comprises the amino acid sequence comprising SEQ ID NO: 44 or a conservatively modified variant of SEQ ID NO: 44, and the CDRL3 comprises the amino acid sequence of SEQ ID NO: 45 or a conservatively modified variant of SEQ ID NO: 45, and the CDRH1 comprises the amino acid sequence of SEQ ID NO: 46 or a conservatively modified variant of SEQ ID NO: 46, the CDRH2 comprises the amino acid sequence comprising SEQ ID NO: 47 or a conservatively modified variant of SEQ ID NO: 47, and the CDRH3 comprises the amino acid sequence of SEQ ID NO: 48 or a conservatively modified variant of SEQ ID NO: 48.

In an even more specific embodiment the CDRL1 comprises the amino acid sequence of SEQ ID NO: 43, the CDRL2 comprises the amino acid sequence comprising SEQ ID NO: 44, the CDRL3 comprises the amino acid sequence of SEQ ID NO: 45, the CDRH1 comprises the amino acid sequence of SEQ ID NO: 46, the CDRH2 comprises the amino acid sequence comprising SEQ ID NO: 47, and the CDRH3 comprises the amino acid sequence of SEQ ID NO: 48.

In certain other embodiments, the canine light chain is a kappa chain in which the CDRL1 comprises the amino acid sequence of SEQ ID NO: 49. In related embodiments, the CDRL1 comprises a conservatively modified variant of SEQ ID NO: 49. In other embodiments, the CDRL2 comprises the amino acid sequence comprising SEQ ID NO: 50. In related embodiments, the CDRL2 comprises a conservatively modified variant of SEQ ID NO: 50. In still other embodiments the CDRL3 comprises the amino acid sequence of SEQ ID NO: 51. In related embodiments the CDRL3 comprises a conservatively modified variant of SEQ ID NO: 51. In yet other embodiments, the CDRH1 of the canine IgG heavy comprises the amino acid sequence of SEQ ID NO: 52. In related embodiments the CDRH1 comprises a conservatively modified variant of of SEQ ID NO: 52. In still other embodiments the CDRH2 comprises the amino acid sequence of SEQ ID NO: 53. In related embodiments the CDRH2 comprises a conservatively modified variant of SEQ ID NO: 53. In yet other embodiments the CDRH3 comprises the amino acid sequence of SEQ ID NO: 54. In related embodiments the CDRH3 comprises a conservatively modified variant of SEQ ID NO: 54.

In specific embodiments the CDRL1 comprises the amino acid sequence of SEQ ID NO: 49 or a conservatively modified variant of SEQ ID NO: 49, the CDRL2 comprises the amino acid sequence comprising SEQ ID NO: 50 or a conservatively modified variant of SEQ ID NO: 50, and the CDRL3 comprises the amino acid sequence of SEQ ID NO: 51 or a conservatively modified variant of SEQ ID NO: 51.

In other specific embodiments the CDRH1 comprises the amino acid sequence of SEQ ID NO: 52 or a conservatively modified variant of SEQ ID NO: 52, the CDRH2 comprises the amino acid sequence comprising SEQ ID NO: 53 or a conservatively modified variant of SEQ ID NO: 53, and the CDRH3 comprises the amino acid sequence of SEQ ID NO: 54 or a conservatively modified variant of SEQ ID NO: 54.

In a more specific embodiment the CDRL1 comprises the amino acid sequence of SEQ ID NO: 49 or a conservatively modified variant of SEQ ID NO: 49, the CDRL2 comprises the amino acid sequence comprising SEQ ID NO: 50 or a conservatively modified variant of SEQ ID NO: 50, and the CDRL3 comprises the amino acid sequence of SEQ ID NO: 51 or a conservatively modified variant of SEQ ID NO: 51, and the CDRH1 comprises the amino acid sequence of SEQ ID NO: 52 or a conservatively modified variant of SEQ ID NO: 52, the CDRH2 comprises the amino acid sequence comprising SEQ ID NO: 53 or a conservatively modified variant of SEQ ID NO: 53, and the CDRH3 comprises the amino acid sequence of SEQ ID NO: 54 or a conservatively modified variant of SEQ ID NO: 54.

In an even more specific embodiment the CDRL1 comprises the amino acid sequence of SEQ ID NO: 49, the CDRL2 comprises the amino acid sequence comprising SEQ ID NO: 50, the CDRL3 comprises the amino acid sequence of SEQ ID NO: 51, the CDRH1 comprises the amino acid sequence of SEQ ID NO: 53, the CDRH2 comprises the amino acid sequence comprising SEQ ID NO: 53, and the CDRH3 comprises the amino acid sequence of SEQ ID NO: 54.

In other embodiments, the canine light chain is a kappa chain in which the CDRL1 comprises the amino acid sequence of SEQ ID NO: 55. In related embodiments the CDRL1 comprises a conservatively modified variant of SEQ ID NO: 55. In other embodiments, the CDRL2 comprises the amino acid sequence comprising SEQ ID NO: 56. In related embodiments the CDRL2 comprises a conservatively modified variant of SEQ ID NO: 56. In still other embodiments the CDRL3 comprises the amino acid sequence of SEQ ID NO: 57. In related embodiments the CDRL3 comprises a conservatively modified variant of SEQ ID NO: 57. In yet other embodiments, the CDRH1 of the canine IgG heavy comprises the amino acid sequence of SEQ ID NO: 58. In related embodiments the CDRH1 comprises a conservatively modified variant of SEQ ID NO: 58. In still other embodiments the CDRH2 comprises the amino acid sequence of SEQ ID NO: 59. In related embodiments the CDRH2 comprises a conservatively modified variant of SEQ ID NO: 59. In yet other embodiments the CDRH3 comprises the amino acid sequence of SEQ ID NO: 60. In related embodiments the CDRH3 comprises a conservatively modified variant of SEQ ID NO: 60.

In specific embodiments the CDRL1 comprises the amino acid sequence of SEQ ID NO: 55 or a conservatively modified variant of SEQ ID NO: 55, the CDRL2 comprises the amino acid sequence comprising SEQ ID NO: 56 or a conservatively modified variant of SEQ ID NO: 56, and the CDRL3 comprises the amino acid sequence of SEQ ID NO: 57 or a conservatively modified variant of SEQ ID NO: 57.

In other specific embodiments the CDRH1 comprises the amino acid sequence of SEQ ID NO: 58 or a conservatively modified variant of SEQ ID NO: 58, the CDRH2 comprises the amino acid sequence comprising SEQ ID NO: 59 or a conservatively modified variant of SEQ ID NO: 59, and the CDRH3 comprises the amino acid sequence of SEQ ID NO: 60 or a conservatively modified variant of SEQ ID NO: 60.

In a more specific embodiment the CDRL1 comprises the amino acid sequence of SEQ ID NO: 55 or a conservatively modified variant of SEQ ID NO: 55, the CDRL2 comprises the amino acid sequence comprising SEQ ID NO: 56 or a conservatively modified variant of SEQ ID NO: 56, and the CDRL3 comprises the amino acid sequence of SEQ ID NO: 57 or a conservatively modified variant of SEQ ID NO: 57, and the CDRH1 comprises the amino acid sequence of SEQ ID NO: 58 or a conservatively modified variant of SEQ ID NO: 58, the CDRH2 comprises the amino acid sequence comprising SEQ ID NO: 59 or a conservatively modified variant of SEQ ID NO: 59, and the CDRH3 comprises the amino acid sequence of SEQ ID NO: 60 or a conservatively modified variant of SEQ ID NO: 60.

In an even more specific embodiment the CDRL1 comprises the amino acid sequence of SEQ ID NO: 55, the CDRL2 comprises the amino acid sequence comprising SEQ ID NO: 56, the CDRL3 comprises the amino acid sequence of SEQ ID NO: 57, the CDRH1 comprises the amino acid sequence of SEQ ID NO: 58, the CDRH2 comprises the amino acid sequence comprising SEQ ID NO: 59, and the CDRH3 comprises the amino acid sequence of SEQ ID NO: 60.

In certain embodiments of the present invention, the IgG heavy chain comprises the amino acid sequence of SEQ ID NO: 28. In a particular embodiment of this type, the IgG heavy chain is encoded by the nucleic acid comprising the nucleotide sequence of SEQ ID NO: 27. In related embodiments the IgG heavy chain comprises a conservatively modified variant of SEQ ID NO: 28. In other embodiments the IgG heavy chain comprises the amino acid sequence of SEQ ID NO: 30. In a particular embodiment of this type, the IgG heavy chain is encoded by the nucleic acid comprising the nucleotide sequence of SEQ ID NO: 29. In related embodiments the IgG heavy chain comprises a conservatively modified variant of SEQ ID NO: 30. In still other embodiments the IgG heavy chain comprises the amino acid sequence of SEQ ID NO: 32. In a particular embodiment of this type, the IgG heavy chain is encoded by the nucleic acid comprising the nucleotide sequence of SEQ ID NO: 31. In related embodiments the IgG heavy chain comprises a conservatively modified variant of SEQ ID NO: 32.

In certain embodiments the kappa light chain comprises the amino acid sequence of SEQ ID NO: 34. In a particular embodiment of this type, the kappa light chain is encoded by the nucleic acid comprising the nucleotide sequence of SEQ ID NO: 33. In related embodiments, the kappa light chain comprises a conservatively modified variant of SEQ ID NO: 34. In certain embodiments the kappa light chain comprises the amino acid sequence of SEQ ID NO: 36. In a particular embodiment of this type, the kappa light chain is encoded by the nucleic acid comprising the nucleotide sequence of SEQ ID NO: 35. In related embodiments, the kappa light chain comprises a conservatively modified variant of SEQ ID NO: 36. In other embodiments the kappa light chain comprises the amino acid sequence of SEQ ID NO: 38. In a particular embodiment of this type, the kappa light chain is encoded by the nucleic acid comprising the nucleotide sequence of SEQ ID NO: 37. In related embodiments, the kappa light chain comprises a conservatively modified variant of SEQ ID NO: 38.

In more particular embodiments, an isolated caninized antibody comprises a IgG heavy chain comprising the amino acid sequence of SEQ ID NO: 28 and a kappa light chain comprising the amino acid sequence of SEQ ID NO: 34, SEQ ID NO:36, or SEQ ID NO: 38. In related embodiments the isolated caninized antibody comprises a IgG heavy chain comprising a conservatively modified variant of the amino acid sequence of SEQ ID NO: 28 and a kappa light chain comprising a conservatively modified variant of the amino acid sequence of SEQ ID NO: 34, SEQ ID NO:36, or SEQ ID NO: 38. In still other related embodiments the isolated caninized antibody comprises a IgG heavy chain comprising the amino acid sequence of SEQ ID NO: 28 and a conservatively modified variant of a kappa light chain comprising the amino acid sequence of SEQ ID NO: 34, SEQ ID NO:36, or SEQ ID NO: 38. In yet other related embodiments the isolated caninized antibody comprises a IgG heavy chain comprising a conservatively modified variant comprising the amino acid sequence of SEQ ID NO: 28 and a kappa light chain comprising the amino acid sequence of SEQ ID NO: 34, SEQ ID NO:36, or SEQ ID NO: 38.

In other particular embodiments, an isolated caninized antibody comprises a IgG heavy chain comprising the amino acid sequence of SEQ ID NO: 30 and a kappa light chain comprising the amino acid sequence of SEQ ID NO: 34, SEQ ID NO:36, or SEQ ID NO: 38. In related embodiments the isolated caninized antibody comprises a conservatively modified variant of a IgG heavy chain comprising SEQ ID NO: 30 and a conservatively modified variant of a kappa light chain comprising the amino acid sequence of SEQ ID NO: 34, SEQ ID NO:36, or SEQ ID NO: 38. In still other related embodiments the isolated caninized antibody comprises a IgG heavy chain comprising the amino acid sequence of SEQ ID NO: 30 and a conservatively modified variant of a kappa light chain comprising the amino acid sequence of SEQ ID NO: 34, SEQ ID NO:36, or SEQ ID NO: 38. In yet other related embodiments the isolated caninized antibody comprises a conservatively modified variant of a IgG heavy chain comprising the amino acid sequence of SEQ ID NO: 30 and a kappa light chain comprising the amino acid sequence of SEQ ID NO: 34, SEQ ID NO:36, or SEQ ID NO: 38.

In alternative particular embodiments, an isolated caninized antibody comprises a IgG heavy chain comprising the amino acid sequence of SEQ ID NO: 32 and a kappa light chain comprising the amino acid sequence of SEQ ID NO: 34, SEQ ID NO:36, or SEQ ID NO: 38. In related embodiments the isolated caninized antibody comprises a conservatively modified variant of a IgG heavy chain comprising the amino acid sequence of SEQ ID NO: 32 and a conservatively modified variant of a kappa light chain comprising the amino acid sequence of SEQ ID NO: 34, SEQ ID NO:36, or SEQ ID NO: 38. In still other related embodiment the isolated caninized antibody comprises a IgG heavy chain comprising the amino acid sequence of SEQ ID NO: 28 and a conservatively modified variant of a kappa light chain comprising the amino acid sequence of SEQ ID NO: 34, SEQ ID NO:36, or SEQ ID NO: 38. In yet other related embodiments the isolated caninized antibody comprises a conservatively modified variant of a IgG heavy chain comprising the amino acid sequence of SEQ ID NO: 28 and a kappa light chain comprising the amino acid sequence of SEQ ID NO: 34, SEQ ID NO:36, or SEQ ID NO: 38.

The present invention also provides chimeric heavy chain and light chain human-canine antibodies. In certain embodiments, the chimeric human-canine heavy chain comprises the amino acid sequence of SEQ ID NO: 16. In a specific embodiment of this type, the chimeric human-canine heavy chain is encoded by the nucleic acid comprising the nucleotide sequence of SEQ ID NO: 15. In certain antibodies the chimeric human-canine kappa chain comprises the amino acid sequence of SEQ ID NO: 18. In a specific embodiment of this type, the chimeric human-canine kappa chain is encoded by the nucleic acid comprising the nucleotide sequence of SEQ ID NO: 17.

In other embodiments, the chimeric human-canine heavy chain comprises the amino acid sequence of SEQ ID NO: 20. In a specific embodiment of this type, the chimeric human-canine heavy chain is encoded by the nucleic acid comprising the nucleotide sequence of SEQ ID NO: 19. In certain antibodies the chimeric human-canine kappa chain comprises the amino acid sequence of SEQ ID NO: 22. In a specific embodiment of this type, the chimeric human-canine kappa chain is encoded by the nucleic acid comprising the nucleotide sequence of SEQ ID NO: 21.

In still other embodiments, the chimeric human-canine heavy chain comprises the amino acid sequence of SEQ ID NO: 24. In a specific embodiment of this type, the chimeric human-canine heavy chain is encoded by the nucleic acid comprising the nucleotide sequence of SEQ ID NO: 23. In certain antibodies the chimeric human-canine kappa chain comprises the amino acid sequence of SEQ ID NO: 26. In a specific embodiment of this type, the chimeric human-canine kappa chain is encoded by the nucleic acid comprising the nucleotide sequence of SEQ ID NO: 25.

The present invention includes antibodies as detailed above, and/or antigen binding fragments thereof that bind canine IL-4Rα with specificity, and that when they are bound to canine IL-4Rα, the antibody binds to at least one amino acid residue within SEQ ID NO: 39 and/or SEQ ID NO: 40 and/or SEQ ID NO: 41 and/or SEQ ID NO: 42. In more specific embodiments the antibody binds to at least one amino acid residue within SEQ ID NO: 41 and/or SEQ ID NO: 42. In even more specific embodiments the antibody binds to at least one or more amino acid residues of SEQ ID NO: 4 selected from the group consisting of $T_{27}$, $Y_{37}$, $S_{164}$, $T_{165}$, $K_{167}$. In particular embodiments of such types, the antibodies and/or antigen binding fragments thereof bind canine IL-4Rα and block the binding of canine IL-4Rα to canine IL-4.

The present invention further provides antigenic peptides (including isolated antigenic peptides) that consist of 80 or fewer amino acid residues that comprise the amino acid sequence of SEQ ID NO: 39 and/or SEQ ID NO: 40. In related embodiments, the antigenic peptides (including isolated peptides) consist of 60 or fewer amino acid residues that comprise the amino acid sequence of SEQ ID NO: 39 and/or SEQ ID NO: 40. In other embodiments, the antigenic peptides consist of 6 to 32 amino acid residues from the amino acid sequence of SEQ ID NO: 39 and/or SEQ ID NO: 40. In still other embodiments, the antigenic peptides consist of 12 to 24 amino acid residues from the amino acid sequence of SEQ ID NO: 39 and/or SEQ ID NO: 40. In particular embodiments the antigenic peptides consist of 6 to 40 amino acid residues and comprise the amino acid sequence of SEQ ID NO: 42. In other particular embodiments the antigenic peptides consist of 6 to 11 amino acid residues from the amino acid sequence of SEQ ID NO: 42. In particular embodiments the antigenic peptides consist of 6 to 40 amino acid residues and comprise the amino acid sequence of SEQ ID NO: 42. In another particular embodiment the antigenic peptides consist of 6 to 11 amino acid residues and comprise the amino acid sequence of SEQ ID NO: 42.

The present invention further provides fusion proteins that comprise any of the aforesaid antigenic peptides. In a particular embodiment, the fusion protein comprises such an antigenic peptide and an Fc region of a non-canine mammalian IgG antibody. In a more particular embodiment the fusion protein comprises an Fc region of a non-canine mammalian IgG antibody. In certain embodiments the non-canine mammalian IgG antibody is a murine IgG. In alternative embodiments the non-canine mammalian IgG antibody is a human IgG. In other embodiments the non-canine mammalian IgG antibody is an equine IgG. In still other embodiments the non-canine mammalian IgG antibody is a porcine IgG. In yet other embodiments the non-canine mammalian IgG antibody is a bovine IgG.

In particular embodiments the non-canine mammalian IgG antibody is an IgG1. In other embodiments the non-canine mammalian IgG antibody is an IgG2a. In still other embodiments the non-canine mammalian IgG antibody is an IgG3. In yet other embodiments the non-canine mammalian IgG antibody is an IgG4.

In other embodiments the fusion protein comprises any of the aforesaid antigenic peptides and maltose-binding protein. In yet other embodiments, the fusion protein comprises any of the aforesaid antigenic peptides and beta-galactosidase. In still other embodiments the fusion protein comprises any of the aforesaid antigenic peptides and glutathione S-transferase. In yet other embodiments, the fusion protein comprises any of the aforesaid antigenic peptides and thioredoxin. In still other embodiments the fusion protein comprises any of the aforesaid antigenic peptides and Gro EL. In yet other embodiments the fusion protein comprises any of the aforesaid antigenic peptides and NusA.

The present invention further provides nucleic acids (including isolated nucleic acids) that encode the antigenic peptides and the corresponding fusion proteins of the present invention. The present invention also provides expression vectors that comprise these nucleic acids.

The present invention further provides nucleic acids that encode any one of the light chains of the caninized antibody of the present invention or antigen binding fragment thereof. In particular embodiments of this type the nucleic acids are isolated nucleic acids. Similarly, the present invention further provides nucleic acids that encode any one of the heavy chains of the caninized antibody of the present invention or antigen binding fragment thereof. In particular embodiments of this type the nucleic acids are isolated nucleic acids. The present invention further provides expression vectors that comprise one or more of the nucleic acids (isolated or otherwise) of the present invention. The present invention also provides host cells that comprise one or more expression vectors of the present invention.

In particular embodiments, the antibody is a recombinant antibody or an antigen binding fragment thereof. In related embodiments, the variable heavy chain domain and variable light chain domain are connected by a flexible linker to form a single-chain antibody.

In particular embodiments, the antibody or antigen binding fragment is a Fab fragment.

In other embodiments, the antibody or antigen binding fragment is a Fab' fragment. In yet other embodiments, the antibody or antigen binding fragment is a (Fab')$_2$ fragment. In still other embodiments, the antibody or antigen binding fragment is a diabody. In particular embodiments, the antibody or antigen binding fragment is a domain antibody. In particular embodiments, the antibody or antigen binding fragment is a camelized single domain antibody.

In particular embodiments, the caninized human anti-human IL-4Rα antibody or antigen binding fragment modulates the development of the Th2 immune response of the canine subject being treated and thereby, ameliorates the symptoms of atopic dermatitis.

The present invention further provides isolated nucleic acids that encode the caninized human anti-human IL-4Rα antibodies or antigen binding fragments as disclosed herein. In related embodiments such antibodies or antigen binding fragments can be used for the preparation of a medicament to treat atopic dermatitis in a canine subject. Alternatively, or in conjunction, the present invention provides for the use of any of the antibodies or antibody fragments of the present invention for diagnostic use. In yet additional embodiments, a kit is provided comprising any of the caninized antibodies or antigen binding fragments disclosed herein.

In yet additional embodiments, an expression vector is provided comprising an isolated nucleic acid encoding any of the caninized human anti-human IL-4Rα antibodies or antigen binding fragments of the invention. The invention also relates to a host cell comprising any of the expression vectors described herein. In particular embodiments, these nucleic acids, expression vectors or polypeptides of the invention are useful in methods of making an antibody.

The present invention further includes pharmaceutical compositions comprising an antibody or antigen binding fragment thereof together with a pharmaceutically acceptable carrier or diluent. In addition, the present invention provides methods of modulating the development of the canine Th2 immune response, comprising administering to a subject in need thereof a therapeutically effective amount of such pharmaceutical compositions. In certain embodiments the method is used for the treatment of atopic dermatitis.

These and other aspects of the present invention will be better appreciated by reference to the following Brief Description of the Drawings and the Detailed Description.

DETAILED DESCRIPTION

Figure 1A:
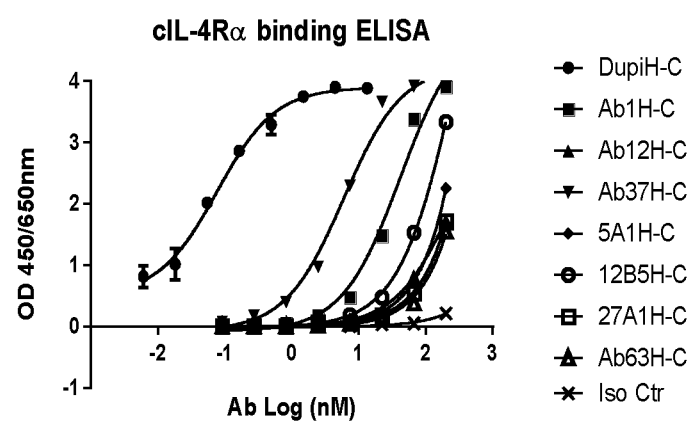
FIG. 1A depicts the binding affinity of human-canine chimera antibodies with cIL-4Rα determined by ELISA. The human portion of the human-canine chimeria was obtained from the following humanized antibodies: Ab1 (M1), Ab 12 (M12), and Ab 37 (M37) [U.S. Pat. No. 8,877,189]; 5A1, 12B5, 27A1, and Ab 63 (63) [U.S. Pat. No. 7,186,809]; and Dupi H-C [US 20150017176]. The Iso control (Iso Ctr) is a caninized murine antibody raised against a canine antigen that is unrelated to cIL-4Rα.

There is only 66% amino acid identity between the canine IL-4 receptor alpha protein and the human IL-4 receptor alpha protein. Moreover, even comparing just the extracellular domains of these receptors, the amino acid identity is only 68%. Despite this fact, several humanized antibodies against human ECD of IL-4Rα were screened for their reactivity with canine IL-4Rα. Notably, it was surprisingly found that one of these humanized antibodies that had been previously identified for being specific for the extracellular domain of the human IL-4Rα protein, also binds to canine IL-4Rα chain with a high affinity. Even more surprisingly, it was found that this antibody could block the binding of canine IL-4 to its canine IL-4Rα chain. Accordingly, the caninization of this antibody, as disclosed below, has a therapeutic utility for dogs.

Abbreviations

Throughout the detailed description and examples of the invention the following abbreviations will be used:
ADCC Antibody-dependent cellular cytotoxicity
CDC Complement-dependent cytotoxicity
CDR Complementarity determining region in the immunoglobulin variable regions, defined using the Kabat numbering system
CHO Chinese hamster ovary
EC50 concentration resulting in 50% efficacy or binding
ELISA Enzyme-linked immunosorbant assay
FR Antibody framework region: the immunoglobulin variable regions excluding the CDR regions.
HRP Horseradish peroxidase
IFN interferon
IC50 concentration resulting in 50% inhibition
IgG Immunoglobulin G
Kabat An immunoglobulin alignment and numbering system pioneered by Elvin A. Kabat [*Sequences of Proteins of Immunological Interest,* 5th Ed. Public Health Service, National Institutes of Health, Bethesda, Md. (1991)]
mAb Monoclonal antibody (also Mab or MAb)
MES 2-(N-morpholino)ethanesulfonic acid
MTT (3-(4,5-dimethylthiazol-2-yl)-2,5-diphenyltetrazolium bromide)
MOA Mechanism of action
NHS Normal human serum
PCR Polymerase chain reaction
PK Pharmacokinetics
SEB *Staphylococcus* Enterotoxin B
TT Tetanus toxoid
V region The segment of IgG chains which is variable in sequence between different antibodies. It extends to Kabat residue 109 in the light chain and 113 in the heavy chain.
VH Immunoglobulin heavy chain variable region
VK Immunoglobulin kappa light chain variable region

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Activation" as it applies to cells or to receptors refers to the activation or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies.

"Activation" can refer to cell activation as regulated by internal mechanisms as well as by external or environmental factors.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems.

"Administration" and "treatment," as it applies to an animal, e.g., a canine subject, cell, tissue, organ, or biological fluid, refers to contact of an exogenous pharmaceutical, therapeutic, diagnostic agent, or composition to the animal e.g., a canine subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell.

The term "subject" includes any organism, preferably an animal, more preferably a mammal (e.g., canine, feline, or other non-human mammal) and most preferably a canine.

As used herein, a "substitution of an amino acid residue" with another amino acid residue in an amino acid sequence of an antibody for example, is equivalent to "replacing an amino acid residue" with another amino acid residue and denotes that a particular amino acid residue at a specific position in the amino acid sequence has been replaced by (or substituted for) by a different amino acid residue. Such substitutions can be particularly designed i.e., purposefully replacing an alanine with a serine at a specific position in the amino acid sequence by e.g., recombinant DNA technology. Alternatively, a particular amino acid residue or string of amino acid residues of an antibody can be replaced by one or more amino acid residues through more natural selection processes e.g., based on the ability of the antibody produced by a cell to bind to a given region on that antigen, e.g., one containing an epitope or a portion thereof, and/or for the antibody to comprise a particular CDR that retains the same canonical structure as the CDR it is replacing. Such substitutions/replacements can lead to "variant" CDRs and/or variant antibodies.

"Treat" or "treating" means to administer a therapeutic agent, such as a composition containing any of the antibodies or antigen binding fragments of the present invention, internally or externally to a canine subject or patient having one or more disease symptoms, or being suspected of having a disease, for which the agent has therapeutic activity.

Typically, the agent is administered in an amount effective to alleviate and/or ameliorate one or more disease symptoms in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient (e.g., canine), and the ability of the pharmaceutical composition to elicit a desired response in the subject. Whether a disease symptom has been alleviated or ameliorated can be assessed by any clinical measurement typically used by veterinarians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the $\text{chi}^2$-test, the U-test according to Mann and Whitney, the Kruskal-Wallis test (H-test), Jonckheere-Terpstra-test and the Wilcoxon-test.

"Treatment," as it applies to a human, veterinary (e.g., canine) or research subject, refers to therapeutic treatment, as well as research and diagnostic applications. "Treatment" as it applies to a human, veterinary (e.g., canine), or research subject, or cell, tissue, or organ, encompasses contact of the antibodies or antigen binding fragments of the present invention to a canine or other animal subject, a cell, tissue, physiological compartment, or physiological fluid.

As used herein, the term "canine" includes all domestic dogs, *Canis lupus familiaris* or *Canis familiaris*, unless otherwise indicated.

As used herein, the term "feline" refers to any member of the Felidae family. Members of this family include wild, zoo, and domestic members, such as any member of the subfamilies Felinae, e.g., cats, lions, tigers, pumas, jaguars, leopards, snow leopards, panthers, North American mountain lions, cheetahs, lynx, bobcats, caracals or any cross breeds thereof. Cats also include domestic cats, pure-bred and/or mongrel companion cats, show cats, laboratory cats, cloned cats, and wild or feral cats.

As used herein the term "canine frame" refers to the amino acid sequence of the heavy chain and light chain of a canine antibody other than the hypervariable region residues defined herein as CDR residues. With regard to a caninized antibody, in the majority of embodiments the amino acid sequences of the native canine CDRs are replaced with the corresponding foreign CDRs (e.g., those from a human anti-human IL-4Rα antibody) in both chains. Optionally the heavy and/or light chains of the canine antibody may be modified to contain some foreign non-CDR residues, e.g., so as to preserve the conformation of the foreign CDRs within the canine antibody, and/or to modify the Fc function, as discussed below. Accordingly, a caninized antibody that comprises a canine IgG heavy chain comprising CDRs from an antibody from another species (e.g., CDRs from a human antibody) and a canine kappa light chain comprising CDRs of an antibody from that other species indicates that the caninized antibody comprises a canine IgG heavy chain (or a modified canine IgG, e.g., as disclosed herein), which comprises the specified CDRs of the antibody from that other species in place of its CDRs and a canine kappa light chain (or a modified canine kappa light chain), which comprises the specified CDRs of the antibody from that other species in place of its CDRs.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the mammalian body (e.g., canine body) of cancerous cells, cells or tissues infected with pathogens, or invading pathogens.

Caninized Anti-Human IL-4Rα Antibodies

The present invention provides isolated caninized human anti-human IL-4Rα antibodies or antigen binding fragments thereof that bind canine IL-4Rα and uses of such antibodies or fragments.

As used herein, a caninized human anti-human IL-4Rα antibody refers to a caninized antibody that specifically binds to mammalian IL-4Rα.

An antibody that specifically binds to mammalian IL-4Rα, and in particular canine IL-4Rα, is an antibody that exhibits preferential binding to mammalian IL-4Rα as compared to other antigens, but this specificity does not require absolute binding specificity. A caninized human anti-human IL-4Rα antibody is considered "specific" for canine IL-4Rα (or binding with specificity) if its binding is determinative of the presence of canine IL-4Rα in a biological sample obtained from a canine, or if it is capable of altering the activity of canine IL-4Rα without unduly interfering with the activity of other canine proteins in a canine sample, e.g. without producing undesired results such as false positives in a diagnostic context or side effects in a therapeutic context. The degree of specificity necessary for a caninized human anti-human IL-4Rα antibody may depend on the intended use of the antibody, and at any rate is defined by its suitability for use for an intended purpose. The antibody, or binding compound derived from the antigen-binding site of an antibody, of the contemplated method binds to its antigen, or a variant or mutein thereof, with specificity, when it has an affinity that is at least two-fold greater, preferably at least ten-times greater, more preferably at least 20-times greater, and most preferably at least 100-times greater than the affinity with any other canine antigen.

As used herein, an antibody is said to bind specifically to a polypeptide comprising a given sequence (in this case canine IL-4Rα) if it binds to polypeptides comprising the sequence of canine IL-4Rα, but does not bind to other canine proteins lacking the amino acid sequence of canine IL-4Rα. For example, an antibody that specifically binds to a polypeptide comprising canine IL-4Rα may bind to a FLAG®-tagged form of canine IL-4Rα, but will not bind to other FLAG®-tagged canine proteins.

As used herein, unless otherwise indicated, "antibody fragment" or "antigen binding fragment" refers to antigen binding fragments of antibodies, i.e. antibody fragments that retain the ability to bind specifically to the antigen (e.g., canine IL-4Rα) bound by the full-length antibody, e.g. fragments that retain one or more CDR regions. Examples of antigen binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

Typically, a caninized antibody or antigen binding fragment thereof of the invention retains at least 10% of its canine IL-4Rα binding activity (when compared to the corresponding parental antibody) when that activity is expressed on a molar basis. Preferably, an antibody or antigen binding fragment of the invention retains at least 20%, 50%, 70%, 80%, 90%, 95% or 100% or more of the canine IL-4Rα binding affinity as the parental antibody. It is also intended that an an antibody or antigen binding fragment of the invention can include conservative or non-conservative amino acid substitutions (referred to as "conservative variants" or "function conserved variants" of the antibody) that do not substantially alter its biologic activity.

"Isolated antibody" refers to the purification status and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

The variable regions of each light/heavy chain pair form the antigen binding site of the antibody. Thus, in general, an intact antibody has two binding sites. Except in bifunctional or bispecific antibodies, the two binding sites are, in general, the same. Typically, the variable domains of both the heavy and light chains comprise three hypervariable regions, also called complementarity determining regions (CDRs), located within relatively conserved framework regions (FR). The CDRs are usually flanked by the framework regions, enabling binding to a specific epitope. In general, from N-terminal to C-terminal, both light and heavy chains variable domains comprise FR1, CDR1, FR2, CDR2, FR3, CDR3, and FR4. The assignment of amino acids to each domain is, generally, in accordance with the definitions of *Sequences of Proteins of Immunological Interest*, Kabat, et al.; National Institutes of Health, Bethesda, Md.; 5th ed.; NIH Publ. No. 91-3242 (1991); Kabat, *Adv. Prot. Chem.* 32:1-75 (1978); Kabat, et al., *J. Biol. Chem.* 252:6609-6616 (1977); Chothia, et al., *J. Mol. Biol.* 196:901-917 (1987) or Chothia, et al., *Nature* 342:878-883 (1989)].

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). [See Kabat et al. *Sequences of Proteins of Immunological Interest,* 5th Ed. Public Health Service, National Institutes of Health, Bethesda, Md. (1991), defining the CDR regions of an antibody by sequence; see also Chothia and Lesk, *J. Mol. Biol.* 196: 901-917 (1987) defining the CDR regions of an antibody by structure]. As used herein, the term "framework" or "FR" residues refers to those variable domain residues other than the hypervariable region residues defined herein as CDR residues.

There are four known IgG heavy chain subtypes of dog IgG and they are referred to as IgG-A, IgG-B, IgG-C, and IgG-D. The two known light chain subtypes are referred to as lambda and kappa. In addition to modulating the development of the canine Th2 immune response, a canine or caninized antibody against IL-4Rα optimally has two attributes:
 1. Lack of effector functions such as antibody-dependent cytotoxicity (ADCC) and complement-dependent cytotoxicity (CDC), and
 2. be readily purified on a large scale using industry standard technologies such as that based on protein A chromatography.

As used herein, the term "caninized antibody" refers to an antibody that comprises the three heavy chain CDRs and the three light chain CDRS from a human anti-human IL-4Rα antibody together with a canine frame or a modified canine frame. A modified canine frame comprises one or more amino acids changes as exemplified herein that further optimize the effectiveness of the caninized antibody, e.g., to increase its binding to canine IL-4Rα and/or its ability to block the binding of canine IL-4Rα to canine IL-4.

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared ×100. For example, if 6 of 10 of the positions in two sequences are matched or homologous when the sequences are optimally aligned then the two sequences are 60% homologous. Generally, the comparison is made when two sequences are aligned to give maximum percent homology.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. It also should be readily understood that when a nucleic acid sequence is provided herein, it may include a stop codon. However, as stop codons are interchangeable the inclusion of a specific stop codon in a sequence should not be viewed as a necessary portion of that sequence.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. [*Nucleic Acids Res.* 33:D256-D261 (2005)].

Properties of Anti-Canine IL-4Rα Antibodies

The present invention provides chimeric and caninized human anti-human IL-4Rα antibodies, methods of use of the antibodies or antigen binding fragments thereof in the treatment of disease e.g., the treatment of atopic dermatitis in canines. In canine, there are four IgG heavy chains referred to as A, B, C, and D. These heavy chains represent four different subclasses of dog IgG, which are referred to as IgGA, IgGB, IgGC and IgGD. Each of the two heavy chains consists of one variable domain (VH) and three constant domains referred to as CH-1, CH-2, and CH-3. The CH-1 domain is connected to the CH-2 domain via an amino acid sequence referred to as the "hinge" or alternatively as the "hinge region".

The DNA and amino acid sequences of these four heavy chains were first identified by Tang et al. [*Vet. Immunol. Immunopathol.* 80: 259-270 (2001)]. The amino acid and DNA sequences for these heavy chains are also available from the GenBank data bases. For example, the amino acid sequence of IgGA heavy chain has accession number AAL35301.1, IgGB has accession number AAL35302.1, IgGC has accession number AAL35303.1, and IgGD has accession number (AAL35304.1). Canine antibodies also contain two types of light chains, kappa and lambda. The DNA and amino acid sequence of these light chains can be obtained from GenBank Databases. For example the kappa light chain amino acid sequence has accession number ABY 57289.1 and the lambda light chain has accession number ABY 55569.1.

In the present invention, the amino acid sequence for each of the four canine IgG Fc fragments is based on the identified boundary of CH-1 and CH-2 domains as determined by Tang et al, supra. Caninized human anti-human IL-4Rα antibodies that bind canine IL-4Rα include, but are not limited to: antibodies that comprise canine IgG-A, IgG-B, and IgG-D heavy chains and/or canine kappa light chains together with human anti-human IL-4Rα CDRs. Accordingly, the present invention provides chimeric canine and human anti-human IL-4Rα antibodies (preferably isolated) and/or caninized human anti-human IL-4Rα antibodies or antigen binding fragments thereof that bind to canine IL-4Rα and block the binding of canine IL-4 and canine IL-13 to the type-I or type II IL-4 receptors.

The present invention further provides full length canine heavy chains that can be matched with corresponding light chains to make a caninized antibody. Accordingly, the present invention further provides caninized human anti-human IL-4Rα antibodies (including isolated caninized human anti-human IL-4Rα antibodies) and methods of use of the antibodies or antigen binding fragments thereof in the treatment of disease and/or conditions e.g., the treatment of atopic dematitis in canines.

The present invention also provides caninized human anti-human IL-4Rα antibodies that comprise a canine fragment crystallizable region (cFc region) in which the cFc has been genetically modified to augment, decrease, or eliminate one or more effector functions. In one aspect of the present invention, the genetically modified cFc decreases or eliminates one or more effector functions. In another aspect of the invention the genetically modified cFc augments one or more effector function. In certain embodiments, the genetically modified cFc region is a genetically modified canine IgGB Fc region. In another such embodiment, the genetically modified cFc region is a genetically modified canine IgGC Fc region. In a particular embodiment the effector function is antibody-dependent cytotoxicity (ADCC) that is augmented, decreased, or eliminated. In another embodiment the effector function is complement-dependent cytotoxicity (CDC) that is augmented, decreased, or eliminated. In yet another embodiment, the cFc region has been genetically modified to augment, decrease, or eliminate both the ADCC and the CDC.

In order to generate variants of canine IgG that lack effector functions, a number of mutant canine IgGB heavy chains were generated. These variants may include one or more of the following single or combined substitutions in the Fc portion of the heavy chain amino acid sequence: P4A, D31A, N63A, G64P, T65A, A93G, and P95A. Variant heavy chains (i.e., containing such amino acid substitutions) were cloned into expression plasmids and transfected into HEK 293 cells along with a plasmid containing the gene encoding a light chain. Intact antibodies expressed and purified from HEK 293 cells were evaluated for binding to Fc$_\gamma$RI and C1q to assess their potential for mediation of immune effector functions [see, WO 2015091910 A2 and U.S. patent application Ser. No. 15/105,211, the contents of both of which are hereby incorporated by reference in their entireties].

The present invention also employs modified canine IgGDs which in place of its natural IgGD hinge region they comprise a hinge region from:

```
IgGA:
                                      SEQ ID NO: 61
FNECRCTDTPPCPVPEP,;

IgGB:
                                      SEQ ID NO: 62
PKRENGRVPRPPDCPKCPAPEM,;
or

IgGC:
                                      SEQ ID NO: 63
AKECECKCNCNNCPCPGCGL,.
```

Alternatively, the IgGD hinge region can be genetically modified by replacing a serine residue with a proline residue, i.e., PKESTCKCIPPCPVPES, SEQ ID NO: 64 (with the proline residue (P) underlined and in bold substituting for the naturally occurring serine residue). Such modifications can lead to a canine IgGD lacking fab arm exchange. The modified canine IgGDs can be constructed using standard methods of recombinant DNA technology [e.g., Maniatis et al., *Molecular Cloning, A Laboratory Manual* (1982)]. In order to construct these variants, the nucleic acids encoding the amino acid sequence of canine IgGD can be modified so that it encodes the modified IgGDs. The modified nucleic acid sequences are then cloned into expression plasmids for protein expression.

The antibody or antigen binding fragment thereof that binds canine IL-4Rα can comprise one, two, three, four, five, or six of the complementarity determining regions (CDRs) of the human anti-human antibody as described herein. The one, two, three, four, five, or six CDRs may be independently selected from the CDR sequences of those provided below. In a further embodiment, the isolated antibody or antigen-binding fragment thereof that binds canine IL-4Rα comprises a canine antibody kappa light chain comprising a human light chain CDR-1, CDR-2, and/or CDR-3 and a canine antibody heavy chain IgG comprising a human heavy chain CDR-1, CDR-2, and/or CDR-3.

In other embodiments, the invention provides antibodies or antigen binding fragments thereof that specifically bind canine IL-4Rα and have canine antibody kappa light chains comprising CDRs comprising at least 80%, 85%, 90%, 95%, 98% or 99% sequence identity with the amino acid sequences of SEQ ID NOs: 43, 44, and/or 45 and canine antibody heavy chain IgG comprising CDRs comprising at least 80%, 85%, 90%, 95%, 98% or 99% sequence identity with the amino acid sequences of SEQ ID NOs: 46, 47, and/or 48, while still exhibiting the desired binding and functional properties. In still other embodiments, the invention provides antibodies or antigen binding fragments thereof that specifically bind canine IL-4Rα and have canine antibody kappa light chains comprising CDRs comprising at least 80%, 85%, 90%, 95%, 98% or 99% sequence identity with the amino acid sequences of SEQ ID NOs: 49, 50, and/or 51 and canine antibody heavy chain IgG comprising CDRs comprising at least 80%, 85%, 90%, 95%, 98% or 99% sequence identity with the amino acid sequences of SEQ ID NOs: 52, 53, and/or 54, while still exhibiting the desired binding and functional properties. In yet other embodiments, the invention provides antibodies or antigen binding fragments thereof that specifically bind canine IL-4Rα and have canine antibody kappa light chains comprising CDRs comprising at least 80%, 85%, 90%, 95%, 98% or 99% sequence identity with the amino acid sequences of SEQ ID NOs: 55, 56, and/or 57 and canine antibody heavy chain IgG comprising CDRs comprising at least 80%, 85%, 90%, 95%, 98% or 99% sequence identity with the amino acid sequences of SEQ ID NOs: 58, 59, and/or 60, while still exhibiting the desired binding and functional properties. In still another embodiment the antibody or antigen binding fragment of the present invention comprises a canine frame comprising a combination of IgG heavy chain sequence with a kappa light chain having one or more of the above-mentioned CDR amino acid sequences with 0, 1, 2, 3, 4, or 5 conservative (or alternatively) non-conservative amino acid substitutions, while still exhibiting the desired binding and functional properties.

Sequence identity refers to the degree to which the amino acids of two polypeptides are the same at equivalent positions when the two sequences are optimally aligned. As used herein one amino acid sequence is 100% "identical" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

Sequence similarity includes identical residues and non-identical, biochemically related amino acids. Biochemically related amino acids that share similar properties and may be interchangeable are discussed "Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity [see, e.g., Watson et al., *Molecular Biology of the Gene*, The Benjamin/Cummings Pub. Co., p. 224 (4th Ed.; 1987)]. In addition, substitutions of structurally or functionally similar amino acids are less likely to disrupt biological activity. Exemplary conservative substitutions are set forth in Table 1 directly below.

TABLE 1

Exemplary Conservative Amino Acid Substitutions

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |

TABLE 1-continued

Exemplary Conservative Amino Acid Substitutions

| Original residue | Conservative substitution |
|---|---|
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table 1.

Nucleic Acids

The present invention further comprises the nucleic acids encoding the immunoglobulin chains of caninized human anti-human IL-4Rα antibodies and antigen binding fragments thereof disclosed herein. For example, the present invention includes all of the novel nucleic acids listed in the Sequence Listing Table below, as well as nucleic acids encoding the peptides and proteins comprising the amino acid sequences provided therein.

Also included in the present invention are nucleic acids that encode immunoglobulin polypeptides comprising amino acid sequences that are at least about 70% identical, preferably at least about 80% identical, more preferably at least about 90% identical and most preferably at least about 95% identical (e.g., 95%, 96%, 97%, 98%, 99%, 100%) to the amino acid sequences of the antibodies provided herein when the comparison is performed by a BLAST algorithm wherein the parameters of the algorithm are selected to give the largest match between the respective sequences over the entire length of the respective reference sequences. The present invention further provides nucleic acids that encode immunoglobulin polypeptides comprising amino acid sequences that are at least about 70% similar, preferably at least about 80% similar, more preferably at least about 90% similar and most preferably at least about 95% similar (e.g., 95%, 96%, 97%, 98%, 99%, 100%) to any of the reference amino acid sequences when the comparison is performed with a BLAST algorithm, wherein the parameters of the algorithm are selected to give the largest match between the respective sequences over the entire length of the respective reference sequences, are also included in the present invention.

Sequence identity refers to the degree to which the amino acids of two polypeptides are the same at equivalent positions when the two sequences are optimally aligned. Sequence similarity includes identical residues and nonidentical, biochemically related amino acids. Biochemically related amino acids that share similar properties and may be interchangeable are discussed above.

The following references relate to BLAST algorithms often used for sequence analysis: BLAST ALGORITHMS: Altschul, S. F., et al., *J. Mol. Biol.* 215:403-410 (1990); Gish, W., et al., *Nature Genet.* 3:266-272 (1993); Madden, T. L., et al., *Meth. Enzymol.* 266:131-141(1996); Altschul, S. F., et al., *Nucleic Acids Res.* 25:3389-3402 (1997); Zhang, J., et al., *Genome Res.* 7:649-656 (1997); Wootton, J. C., et al., *Comput. Chem.* 17:149-163 (1993); Hancock, J. M. et al., *Comput. Appl. Biosci.* 10:67-70 (1994); ALIGNMENT SCORING SYSTEMS: Dayhoff, M. O., et al., "A model of evolutionary change in proteins." in *Atlas of Protein Sequence and Structure*, vol. 5, suppl. 3. M. O. Dayhoff (ed.), pp. 345-352, (1978); Natl. Biomed. Res. Found., Washington, D.C.; Schwartz, R. M., et al., "Matrices for detecting distant relationships." in Atlas of Protein Sequence and Structure, vol. 5, suppl. 3." (1978), M. O. Dayhoff (ed.), pp. 353-358 (1978), Natl. Biomed. Res. Found., Washington, D.C.; Altschul, S. F., *J. Mol. Biol.* 219:555-565 (1991); States, D. J., et al., *Methods* 3:66-70(1991); Henikoff, S., et al., *Proc. Natl. Acad. Sci. USA* 89:10915-10919 (1992); Altschul, S. F., et al., *J. Mol. Evol.* 36:290-300 (1993); ALIGNMENT STATISTICS: Karlin, S., et al., *Proc. Natl. Acad. Sci. USA* 87:2264-2268 (1990); Karlin, S., et al., *Proc. Natl. Acad. Sci. USA* 90:5873-5877 (1993); Dembo, A., et al., *Ann. Prob.* 22:2022-2039 (1994); and Altschul, S. F. "Evaluating the statistical significance of multiple distinct local alignments." in *Theoretical and Computational Methods in Genome Research* (S. Suhai, ed.), pp. 1-14, Plenum, N.Y. (1997).

This present invention also provides expression vectors comprising the isolated nucleic acids of the invention, wherein the nucleic acid is operably linked to control sequences that are recognized by a host cell when the host cell is transfected with the vector. Also provided are host cells comprising an expression vector of the present invention and methods for producing the antibody or antigen binding fragment thereof disclosed herein comprising culturing a host cell harboring an expression vector encoding the antibody or antigen binding fragment in culture medium, and isolating the antigen or antigen binding fragment thereof from the host cell or culture medium.

Epitope Binding and Binding Affinity

The chimeric (human/canine) and caninized human anti-human IL-4Rα antibodies or antigen binding fragments thereof of the present invention are capable of inhibiting the binding of canine IL-4Rα to canine IL-4 and/or bind to an epitope comprising one or more amino acid sequences of SEQ ID NOs: 39 and/or 40 and/or 41, and/or 42.

The caninized human anti-human IL-4Rα antibody can be produced recombinantly as described below in the examples. Mammalian cell lines available as hosts for expression of the antibodies or fragments disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, are comprised by the present invention, independent of the glycosylation pattern that the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo [See for example, Shinkawa et al., *J. Biol. Chem.* 278: 3466-3473 (2003); U.S. Pat. Nos. 6,946,292 and 7,214,775].

The present invention further includes antibody fragments of the caninized human anti-human IL-4Rα antibodies disclosed herein. The antibody fragments include F(ab)$_2$ fragments, which may be produced by enzymatic cleavage of an IgG by, for example, pepsin. Fab fragments may be produced by, for example, reduction of F(ab)$_2$ with dithiothreitol or mercaptoethylamine. A Fab fragment is a $V_L$-$C_L$ chain appended to a $V_H$-$C_{H1}$ chain by a disulfide bridge. A F(ab)$_2$ fragment is two Fab fragments which, in turn, are appended by two disulfide bridges. The Fab portion of an F(ab)$_2$ molecule includes a portion of the $F_c$ region between which disulfide bridges are located. An $F_V$ fragment is a $V_L$ or $V_H$ region.

In one embodiment, the antibody or antigen binding fragment comprises a heavy chain constant region, e.g., a canine constant region, such as IgG-A, IgG-B, IgG-C and IgG-D canine heavy chain constant region or a variant thereof. In another embodiment, the antibody or antigen binding fragment comprises a light chain constant region, e.g., a canine light chain constant region, such as lambda or kappa canine light chain region or variant thereof. By way of example, and not limitation the canine heavy chain constant region can be from IgG-D and the canine light chain constant region can be from kappa.

Antibody Engineering

The caninized human anti-human IL-4Rα antibodies of the present invention have been engineered to include modifications to framework residues within the variable domains of a parental (i.e., canine) monoclonal antibody, e.g. to improve the properties of the antibody.

Experimental and Diagnostic Uses

Caninized human anti-human IL-4Rα antibodies or antigen-binding fragments thereof of the present invention may also be useful in diagnostic assays for canine IL-4Rα protein, e.g., detecting its expression in specific cells, tissues, or serum. Such diagnostic methods may be useful in various disease diagnoses. For example, such a method comprises the following steps:
(a) coat a substrate (e.g., surface of a microtiter plate well, e.g., a plastic plate) with caninized human anti-human IL-4Rα antibody or an antigen-binding fragment thereof;
(b) apply a sample to be tested for the presence of canine IL-4Rα to the substrate;
(c) wash the plate, so that unbound material in the sample is removed;
(d) apply detectably labeled antibodies (e.g., enzyme-linked antibodies) which are also specific to the IL-4Rα antigen;
(e) wash the substrate, so that the unbound, labeled antibodies are removed;
(f) if the labeled antibodies are enzyme linked, apply a chemical which is converted by the enzyme into a fluorescent signal; and
(g) detect the presence of the labeled antibody.

In a further embodiment, the labeled antibody is labeled with peroxidase which reacts with ABTS [e.g., 2,2'-azino-bis(3-ethylbenzthiazoline-6-sulphonic acid)] or 3,3',5,5'-Tetramethylbenzidine to produce a color change which is detectable. Alternatively, the antibody is labeled with a detectable radioisotope (e.g., $^3$H) which can be detected with a scintillation counter in the presence of a scintillant. Caninized human anti-human IL-4Rα antibodies of the invention may be used in a Western blot or immuno protein blot procedure.

Such a procedure forms part of the present invention and includes for example:
(i) contacting a membrane or other solid substrate to be tested for the presence of bound canine IL-4Rα or a fragment thereof with a caninized human anti-human IL-4Rα antibody or antigen-binding fragment thereof of the present invention. Such a membrane may take the form of a nitrocellulose or vinyl-based [e.g., polyvinylidene fluoride (PVDF)] membrane to which the proteins to be tested for the presence of canine IL-4Rα in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contact of membrane with the caninized human anti-human IL-4Rα antibody or antigen-binding fragment thereof, the membrane is optionally blocked, e.g., with non-fat dry milk or the like so as to bind non-specific protein binding sites on the membrane.
(ii) washing the membrane one or more times to remove unbound caninized human anti-human IL-4Rα antibody or an antigen-binding fragment thereof and other unbound substances; and
(iii) detecting the bound caninized human anti-human IL-4Rα antibody or antigen-binding fragment thereof.

Detection of the bound antibody or antigen-binding fragment may be by binding the antibody or antigen-binding fragment with a secondary antibody (an anti-immunoglobulin antibody) which is detectably labeled and, then, detecting the presence of the secondary antibody.

The caninized human anti-human IL-4Rα antibodies and antigen-binding fragments thereof disclosed herein may also be used for immunohistochemistry. Such a method forms part of the present invention and comprises, e.g., (1) contacting a cell to be tested for the presence of canine IL-4Rα with a caninized human anti-human IL-4Rα antibody or antigen-binding fragment thereof of the present invention; and (2) detecting the antibody or fragment on or in the cell. If the antibody or antigen-binding fragment itself is detectably labeled, it can be detected directly. Alternatively, the antibody or antigen-binding fragment may be bound by a detectably labeled secondary antibody which is detected.

Imaging techniques include SPECT imaging (single photon emission computed tomography) or PET imaging (positron emission tomography). Labels include e.g., iodine-123 ($^{123}$I) and technetium-99m ($^{99m}$Tc), e.g., in conjunction with SPECT imaging or $^{11}$C, $^{13}$N, $^{15}$O or $^{18}$F, e.g., in conjunction with PET imaging or Indium-111 [See e.g., Gordon et al., *International Rev. Neurobiol.* 67:385-440 (2005)].

Pharmaceutical Compositions and Administration To prepare pharmaceutical or sterile compositions of the caninized human anti-human IL-4Rα antibody or antigen binding fragment thereof is admixed with a pharmaceutically acceptable carrier or excipient. [See, e.g., *Remington's Pharmaceutical Sciences* and *U.S. Pharmacopeia: National Formulary*, Mack Publishing Company, Easton, Pa. (1984)].

Formulations of therapeutic and diagnostic agents may be prepared by mixing with acceptable carriers, excipients, or stabilizers in the form of, e.g., lyophilized powders, slurries, aqueous solutions or suspensions [see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.]. In one embodiment, anti-IL-4Rα antibodies of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in canines. The dosage of such compounds lies preferably within a range of circulating concentrations that include the $ED_{50}$ with little or no toxicity. The dosage may vary within this range depending upon the dosage form employed and the route of administration.

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial. In particular embodiments, the caninized human anti-human IL-4Rα antibody or antigen binding fragment thereof can be administered by an invasive route such as by injection. In further embodiments of the invention, a caninized human anti-human IL-4Rα antibody or antigen binding fragment thereof, or pharmaceutical composition thereof, is administered intravenously, subcutaneously, intramuscularly, intraarterially, intratumorally, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector. The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternatively, one may administer the caninized human anti-human IL-4Rα antibody in a local rather than systemic manner, for example, via injection of the antibody directly into a joint or lesion, often in a depot or sustained release formulation. Furthermore, one may administer the caninized human anti-human IL-4Rα antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available [see, e.g., Wawrzynczak *Antibody Therapy*, Bios Scientific Pub. Ltd, Oxfordshire, U K (1996); Kresina (ed.) *Monoclonal Antibodies, Cytokines and Arthritis,* Marcel Dekker, New York, N.Y. (1991); Bach (ed.) *Monoclonal Antibodies and Peptide Therapy in Autoimmune Diseases*, Marcel Dekker, New York, N.Y. (1993); Baert, et al. *New Engl. J. Med.* 348:601-608 (2003); Milgrom et al. *New Engl. J. Med.* 341:1966-1973 (1999); Slamon et al. *New Engl. J. Med.* 344:783-792 (2001); Beniaminovitz et al. *New Engl. J. Med.* 342:613-619 (2000); Ghosh et al. *New Engl. J. Med.* 348:24-32 (2003); Lipsky et al. *New Engl. J. Med.* 343:1594-1602 (2000)].

Determination of the appropriate dose is made by the veterinarian, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Antibodies or antigen binding fragments thereof disclosed herein may be provided by continuous infusion, or by doses administered, e.g., daily, 1-7 times per week, weekly, biweekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more [see, e.g., Yang, et al. *New Engl. J. Med.* 349:427-434 (2003); Herold, et al. *New Engl. J. Med.* 346:1692-1698 (2002); Liu, et al. *J. Neurol. Neurosurg. Psych.* 67:451-456 (1999); Portielji, et al. *Cancer Immunol. Immunother.* 52:133-144 (2003)]. Doses may also be provided to achieve a pre-determined target concentration of the caninized human anti-human IL-4Rα antibody in the subject's serum, such as 0.1, 0.3, 1, 3, 10, 30, 100, 300 µg/ml or more. In other embodiments, a caninized human anti-human IL-4Rα antibody of the present invention is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of the caninized human anti-human IL-4Rα antibody or antigen binding fragment thereof of the present invention that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the binding compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Other Combination Therapies

As previously described, the caninized human anti-human IL-4Rα antibody or antigen binding fragment thereof may be coadministered with one or other more therapeutic agents (such as a pharmaceutical that is used to treat atopic dermatitis). The antibody may be linked to the agent (as an immunocomplex) or can be administered separately from the agent. In the latter case (separate administration), the antibody can be administered before, after or concurrently with the agent or can be co-administered with other known therapies.

Kits

Further provided are kits comprising one or more components that include, but are not limited to, an antibody or antigen binding fragment, as discussed herein, which specifically binds IL-4Rα (e.g., a caninized human anti-human IL-4Rα antibody or antigen binding fragment thereof of the present invention) in association with one or more additional components including, but not limited to a pharmaceutically acceptable carrier and/or a pharmaceutical that is used to treat atopic dermatitis, as discussed herein. The binding composition and/or the pharmaceutical that is used to treat atopic dermatitis can be formulated as a pure composition or in combination with a pharmaceutically acceptable carrier, in a pharmaceutical composition.

In one embodiment, the kit includes a binding composition of the invention the caninized human anti-human IL-4Rα antibody comprising a heavy chain amino acid sequence of SEQ ID NO: 28, 30, and/or 32 together with the light chain amino acid sequence of SEQ ID NO: 34, 36, and/or 38, or a pharmaceutical composition thereof in one container (e.g., in a sterile glass or plastic vial) and a pharmaceutical composition thereof and/or the pharmaceutical that is used to treat atopic dermatitis in another container (e.g., in a sterile glass or plastic vial).

In another embodiment, the kit comprises a combination of the invention, including a binding composition component, e.g., the caninized human anti-human IL-4Rα antibody comprising a heavy chain amino acid sequence of SEQ ID NO: 28, 30, and/or 32 together with a light chain amino acid sequence of SEQ ID NO: 34, 36, and/or 38, along with a pharmaceutically acceptable carrier, optionally in combination with one or more therapeutic agent component formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above. The kit can also include a package insert including information concerning the pharmaceutical compositions and dosage forms in the kit. Generally, such information aids pet owners and veterinarians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and/or patent information.

As a matter of convenience, an antibody or specific binding agent disclosed herein can be provided in a kit, i.e., a packaged combination of reagents in predetermined amounts with instructions for performing the diagnostic or detection assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

EXAMPLES

Example 1

Identification and Cloning of Canine IL-4 Receptor Alpha Chain

The cDNA encoding a predicted full length canine IL-4 receptor alpha chain (SEQ ID NO: 1) was identified through a search of the Genbank database (accession #XM_547077.4). This predicted cDNA encodes an 823 amino acids (SEQ ID NO: 2) including a 25 amino acid leader sequence and is identified as accession #XP_547077.3. The mature predicted canine IL-4 receptor α chain protein (SEQ ID NO: 4) shares 65% identity with human IL-4 receptor α chain (accession #NP_000409.1) and 70% identity with swine IL-4 receptor α chain (accession #NP_999505.1). The mature predicted canine IL-4 receptor α chain protein is encoded by the nucleotide sequence identified as SEQ ID NO: 3. Comparison of the predicted mature IL-4 receptor α chain with the known sequences of human IL-4 receptor α chain identified the extracellular domain (ECD) of the mature canine IL-4 receptor α chain protein and is designated as SEQ ID NO: 6. The DNA sequence encoding the ECD of the mature canine IL-4 receptor α chain is identified as SEQ ID NO: 5.

```
Canine IL-4 receptor α chain full length DNA with signal sequence
(SEQ ID NO: 1):
atgggcagactgtgcagcggcctgaccttccccgtgagctgcctggtgctggtgtgggtggccagcagcggcagcg tgaaggtgctgcacgagcccagctgcttcagcgactacatcagcaccagcgtgtgccagtggaagatggaccaccc caccaactgcagcgccgagctgagactgagctaccagctggacttcatgggcagcgagaaccacacctgcgtgccc gagaacagagaggacagcgtgtgcgtgtgcagcatgcccatcgacgacgccgtggaggccgacgtgtaccagctgg acctgtgggccggccagcagctgctgtggagcggcagcttccagcccagcaagcacgtgaagcccagaaccccgg caacctgaccgtgcaccccaacatcagccacacctggctgctgatgtggaccaaccctaccccaccgagaaccac ctgcacagcgagctgacctacatggtgaacgtgagcaacgacaacgaccccgaggacttcaaggtgtacaacgtga cctacatgggccccaccctgagactggccgccagcaccctgaagagcggcgccagctacagcgcagagtgagagc ctgggcccagacctacaacagcacctggagcgactggagcccagcaccacctggctgaactactacgagccctgg gagcagcacctgccctgggcgtgagcatcagctgcctggtgatcctggccatctgcctgagctgctacttcagca tcatcaagatcaagaagggctggtgggaccagatccccaaccccgccacagcccctggtggccatcgtgatcca ggacagccaggtgagcctgtggggcaagagaagcagaggccaggagcccgccaagtgcccccactggaagacctgc ctgaccaagctgctgccctgcctgctggagcacggcctgggcagagaggaggagagccccaagaccgccaagaacg gccccctgcagggccccggcaagcccgcctggtgccccgtggaggtgagcaagaccatcctgtggcccgagagcat cagcgtggtgcagtgcgtggagctgagcgaggccccgtggacaacgaggaggaggaggaggtggaggaggacaag agaagcctgtgccccagcctggagggcagcggcggcagcttccaggagggcagagagggcatcgtggccagactga ccgagagcctgttcctggacctgctgggcggcgagaacggcggcttctgccccagggcctggaggagagctgcct gccccccccagcggcagcgtgggcgcccagatgccctgggcccagttccccagagccggccccagagccgccccc gagggccccgagcagcccagaagaccccgagagcgccctgcaggccagccccacccagagcgccggcagcagcgcct tccccgagcccccccccgtggtgaccgacaacccgcctacagaagcttcggcagcttcctgggccagagcagcga cccggcgacggcgacagcgaccccgagctggccgacagaccccggcgaggccgaccccggcatcccagcgcccc cagcccccgagccccgcgcccctgcagcccgagcccgagagctgggagcagatcctgagacagagcgtgctgc agcacagagccgccccgcccgccccggcccgggccgggcgcagcggctacagagagttcacctgcgccgtgaagcaggg
```

-continued

```
cagcgcccccgacgccggcggccccggcttcggccccagcggcgaggccggctacaaggccttctgcagcctgctg cccggcggcgccacctgccccggcaccagcggcggcgaggccggcagcggcgagggcggctacaagcccttccaga gcctgaccccggctgcccggcgcccccaccccgtgcccgtgcccctgttcaccttcggcctggacaccgagcc ccccggcagcccccaggacagcctgggcgccggcagcagccccgagcacctgggcgtggagcccgccggcaaggag gaggacagcagaaagaccctgctggcccccgagcaggccaccgaccccctgagagacgacctggccagcagcatcg tgtacagcgccctgacctgccacctgtgcggccacctgaagcagtggcacgaccaggaggagagaggcaaggccca catcgtgcccagccctgctgcggctgctgctgcggcgacagaagcagcctgctgctgagcccctgagagccccc aacgtgctgcccggcggcgtgctgctggaggccagcctgagccccgccagcctggtgcccagcggcgtgagcaagg agggcaagagcagccccttcagccagcccgccagcagcagcgcccagagcagcagccagacccccaagaagctggc cgtgctgagcaccgagcccacctgcatgagcgccagc
```

Canine IL-4 receptor α full length protein with signal sequence in bold font
(SEQ ID NO: 2).

MGRLCSGLTFPVSCLVLVWVASSGSVKVLHEPSCFSDYISTSVCQWKMDHPTNCSAELRLSYQLDFMGSENHTCVP

ENREDSVCVCSMPIDDAVEADVYQLDLWAGQQLLWSGSFQPSKHVKPRTPGNLTVHPNISHTWLLMWTNPYPTENH

LHSELTYMVNVSNDNDPEDFKVYNVTYMGPTLRLAASTLKSGASYSARVRAWAQTYNSTWSDWSPSTTWLNYYEPW

EQHLPLGVSISCLVILAICLSCYFSIIKIKKGWWDQIPNPAHSPLVAIVIQDSQVSLWGKRSRGQEPAKCPHWKTC

LTKLLPCLLEHGLGREEESPKTAKNGPLQGPGKPAWCPVEVSKTILWPESISVVQCVELSEAPVDNEEEEEVEEDK

RSLCPSLEGSGGSFQEGREGIVARLTESLFLDLLGGENGGFCPQGLEESCLPPPSGSVGAQMPWAQFPRAGPRAAP

EGPEQPRRPESALQASPTQSAGSSAFPEPPPVVTDNPAYRSFGSFLGQSSDPGDGDSDPELADRPGEADPGIPSAP

QPPEPPAALQPEPESWEQILRQSVLQHRAAPAPGPGPGSGYREFTCAVKQGSAPDAGGPGFGPSGEAGYKAFCSLL

PGGATCPGTSGGEAGSGEGGYKPFQSLTPGCPGAPTPVPVPLFTFGLDTEPPGSPQDSLGAGSSPEHLGVEPAGKE

EDSRKTLLAPEQATDPLRDDLASSIVYSALTCHLCGHLKQWHDQEERGKAHIVPSPCCGCCCGDRSSLLLSPLRAP

NVLPGGVLLEASLSPASLVPSGVSKEGKSSPFSQPASSSAQSSSQTPKKLAVLSTEPTCMSAS

Canine IL-4 receptor mature full length protein without signal sequence
(SEQ ID NO: 4)

VKVLHEPSCFSDYISTSVCQWKMDHPTNCSAELRLSYQLDFMGSENHTCVPENREDSVCVCSMPIDDAVEADVYQL

DLWAGQQLLWSGSFQPSKHVKPRTPGNLTVHPNISHTWLLMWTNPYPTENHLHSELTYMVNVSNDNDPEDFKVYNV

TYMGPTLRLAASTLKSGASYSARVRAWAQTYNSTWSDWSPSTTWLNYYEPWEQHLPLGVSISCLVILAICLSCYFS

IIKIKKGWWDQIPNPAHSPLVAIVIQDSQVSLWGKRSRGQEPAKCPHWKTCLTKLLPCLLEHGLGREEESPKTAKN

GPLQGPGKPAWCPVEVSKTILWPESISVVQCVELSEAPVDNEEEEEVEEDKRSLCPSLEGSGGSFQEGREGIVARL

TESLFLDLLGGENGGFCPQGLEESCLPPPSGSVGAQMPWAQFPRAGPRAAPEGPEQPRRPESALQASPTQSAGSSA

FPEPPPVVTDNPAYRSFGSFLGQSSDPGDGDSDPELADRPGEADPGIPSAPQPPEPPAALQPEPESWEQILRQSVL

QHRAAPAPGPGPGSGYREFTCAVKQGSAPDAGGPGFGPSGEAGYKAFCSLLPGGATCPGTSGGEAGSGEGGYKPFQ

SLTPGCPGAPTPVPVPLFTFGLDTEPPGSPQDSLGAGSSPEHLGVEPAGKEEDSRKTLLAPEQATDPLRDDLASSI

VYSALTCHLCGHLKQWHDQEERGKAHIVPSPCCGCCCGDRSSLLLSPLRAPNVLPGGVLLEASLSPASLVPSGVSK

EGKSSPFSQPASSSAQSSSQTPKKLAVLSTEPTCMSAS

Canine IL-4 receptor mature full length DNA without signal sequence
(SEQ ID NO: 3)

```
gtgaaggtgctgcacgagcccagctgcttcagcgactacatcagcaccagcgtgtgccagtggaagatggaccacc ccaccaactgcagcgccgagctgagactgagctaccagctggacttcatgggcagcgagaaccacacctgcgtgcc cgagaacagagaggacagcgtgtgcgtgtgcagcatgcccatcgacgacgccgtggaggccgacgtgtaccagctg gacctgtgggccggccagcagctgctgtggagcggcagcttccagcccagcaagcacgtgaagcccagaaccccg gcaacctgaccgtgcacccaacatcagccacacctggctgctgatgtggaccaaccctacccaccgagaacca cctgcacagcgagctgacctacatggtgaacgtgagcaacgacaacgaccccgaggacttcaaggtgtacaacgtg
```

-continued

```
acctacatgggccccaccctgagactggccgccagcaccctgaagagcggcgccagctacagcgccagagtgagag cctgggcccagacctacaacagcacctggagcgactggagcccagcaccacctggctgaactactacgagccctg ggagcagcacctgcccctgggcgtgagcatcagctgcctggtgatcctggccatctgcctgagctgctacttcagc atcatcaagatcaagaagggctggtgggaccagatccccaacccgcccacagcccctggtggccatcgtgatcc aggacagccaggtgagcctgtggggcaagagaagcagaggccaggagcccgccaagtgcccccactggaagacctg cctgaccaagctgctgccctgcctgctggagcacggcctgggcagagaggaggagagccccaagaccgccaagaac ggcccctgcagggccccggcaagcccgcctggtgccccgtggaggtgagcaagaccatcctgtggcccgagagca tcagcgtggtgcagtgcgtggagctgagcgaggcccccgtggacaacgaggaggaggaggaggtggaggaggacaa gagaagcctgtgccccagcctggagggcagcggcggcagcttcaggagggcagagagggcatcgtggccagactg accgagagcctgttcctggacctgctgggcggcgagaacggcggcttctgccccagggcctggaggagagctgcc tgccccccccagcggcagcgtgggcgcccagatgccctgggcccagttccccagagccggccccagagccgcccc cgagggccccgagcagcccagaagacccgagagcgccctgcaggccagccccacccagagcgccggcagcagcgcc ttccccgagcccccccccgtggtgaccgacaaccccgcctacagaagcttcggcagcttcctgggccagagcagcg accccggcgacggcgacagcgaccccgagctggccgacagaccccggcgaggccgaccccggcatccccagcgcccc ccagcccccgagcccccgccgccctgcagcccgagcccgagagctgggagcagatcctgagacagagcgtgctg cagcacagagccgccccgcccccggccccggccccggcagcggctacagagagttcacctgcgccgtgaagcagg gcagcgcccccgacgccggcggccccggcttcggcccagcggcgaggccggctacaaggccttctgcagcctgct gcccggcggcgccacctgccccggcaccagcggcggcgaggccggcagcggcgagggcggctacaagcccttccag agcctgaccccggctgccccggcgccccacccccgtgccgtgccctgttcaccttcggcctggacaccgagc cccccggcagccccaggacagcctgggcgccggcagcagccccgagcacctgggcgtggagcccgccggcaagga ggaggacagcagaaagaccctgctggcccccgagcaggccaccgaccccctgagagacgacctggccagcagcatc gtgtacagcgccctgacctgccacctgtgcggccacctgaagcagtggcacgaccaggaggagagaggcaaggccc acatcgtgcccagcccctgctgcggctgctgctgcggcgacagaagcagcctgctgctgagcccctgagagcccc caacgtgctgcccggcggcgtgctgctggaggccagcctgagccccgccagcctggtgcccagcggcgtgagcaag gagggcaagagcagccccttcagccagcccgccagcagcagcgcccagagcagcagccagaccccaagaagctgg ccgtgctgagcaccgagcccacctgcatgagcgccagc
```

Canine IL-4 receptor α chain extracellular protein domain without the signal sequence (SEQ ID NO: 6):
VKVLHEPSCFSDYISTSVCQWKMDHPTNCSAELRLSYQLDFMGSENHTCVPENREDSVCVCSMPIDDAVEADVYQL

DLWAGQQLLWSGSF

Canine IL-4 receptor α chain extracellular domain with a c-terminal 8 HIS Tag (SEQ ID NO: 8):
VKVLHEPSCFSDYISTSVCQWKMDHPTNCSAELRLSYQLDFMGSENHTCVPENREDSVCVCSMPIDDAVEADVYQL

DLWAGQQLLWSGSFQPSKHVKPRTPGNLTVHPNISHTWLLMWTNPYPTENHLHSELTYMVNVSNDNDPEDFKVYNV

TYMGPTLRLAASTLKSGASYSARVRAWAQTYNSTWSDWSPSTTWLNYYEPWEQHLPHHHHHHHH

Canine IL-4 receptor α chain extracellular DNA domain with a c-terminal 8 HIS Tag (SEQ ID NO: 7):
gtgaaggtgctgcacgagcccagctgcttcagcgactacatcagcaccagcgtgtgccagtggaagatggaccacc ccaccaactgcagcgccgagctgagactgagctaccagctggacttcatgggcagcgagaaccacacctgcgtgcc cgagaacagagaggacagcgtgtgcgtgtgcagcatgcccatcgacgacgccgtggaggccgacgtgtaccagctg gacctgtgggccggccagcagctgctgtggagcggcagcttccagcccagcaagcacgtgaagcccagaaccccg gcaacctgaccgtgcaccccaacatcagccacacctggctgctgatgtggaccaaccctaccccaccgagaacca cctgcacagcgagctgacctacatggtgaacgtgagcaacgacaacgaccccgaggacttcaaggtgtacaacgtg acctacatgggccccacctgagactggccgccagcaccctgaagagcggcgccagctacagcgccagagtgagag cctgggcccagacctacaacagcacctggagcgactggagccccagcaccacctggctgaactactacgagccctg ggagcagcacctgccccaccaccaccaccaccaccac Canine IL-4 receptor α chain extracellular domain plus human IgG1 Fc (SEQ ID NO: 10):
VKVLHEPSCFSDYISTSVCQWKMDHPTNCSAELRLSYQLDFMGSENHTCVPENREDSVCVCSMPIDDAVEADVYQL

DLWAGQQLLWSGSFQPSKHVKPRTPGNLTVHPNISHTWLLMWTNPYPTENHLHSELTYMVNVSNDNDPEDFKVYNV

TYMGPTLRLAASTLKSGASYSARVRAWAQTYNSTWSDWSPSTTWLNYYEPWEQHLEPKSCDKTHTCPPCPAPELLG

GPSVFLFPPKPKDTLMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQKSLSLSPGK

Canine IL-4 receptor α chain extracellular DNA domain plus human IgG1 Fc (SEQ ID NO: 9):
gtgaaggtgctgcacgagcccagctgcttcagcgactacatcagcaccagcgtgtgccagtggaagatggaccacc ccaccaactgcagcgccgagctgagactgagctaccagctggacttcatgggcagcgagaaccacacctgcgtgcc cgagaacagagaggacagcgtgtgcgtgtgcagcatgcccatcgacgacgccgtggaggccgacgtgtaccagctg gacctgtgggccggccagcagctgctgtggagcggcagcttccagcccagcaagcacgtgaagcccagaaccccg gcaacctgaccgtgcaccccaacatcagccacacctggctgctgatgtggaccaaccctaccccaccgagaacca cctgcacagcgagctgacctacatggtgaacgtgagcaacgacaacgaccccgaggacttcaaggtgtacaacgtg acctacatgggccccacctgagactggccgccagcaccctgaagagcggcgccagctacagcgccagagtgagag cctgggcccagacctacaacagcacctggagcgactggagccccagcaccacctggctgaactactacgagccctg ggagcagcacctggagcccaagagctgcgacaagacccacacctgcccccctgccccgccccgagctgctgggc ggccccagcgtgttcctgttcccccccaagcccaaggacaccctgatgatcagcagaaccccgaggtgacctgcg tggtggtggacgtgagccacgaggaccccgaggtgaagttcaactggtacgtggacggcgtggaggtgcacaacgc caagaccaagcccagagaggagcagtacaacagcacctacagagtggtgagcgtgctgaccgtgctgcaccaggac tggctgaacggcaaggagtacaagtgcaaggtgagcaacaaggccctgcccgcccccatcgagaagaccatcagca aggccaagggccagcccagagagccccaggtgtacaccctgcccccagcagagacgagctgaccaagaaccaggt gagcctgacctgcctggtgaagggcttctaccccagcgacatcgccgtggagtgggagagcaacggccagcccgag aacaactacaagaccacccccccgtgctggacagcgacggcagcttcttcctgtacagcaagctgaccgtggaca agagcagatggcagcagggcaacgtgttcagctgcagcgtgatgcacgaggccctgcacaaccactacacccagaa gagcctgagcctgagccccggcaag

Example 2

Chimeric and Caninized Human Anti-Human IL-4Rα Monoclonal Antibodies

In an effort to develop a treatment for atopic dermatitis in canines, an investigation was undertaken to learn whether any of the known humanized antibodies to human IL-4 receptor alpha [see e.g., U.S. Pat. Nos. 8,877,189, 7,186,809, and US 2015/0017176 A1], might also bind to canine IL-4Rα. It was found that several of these humanized monoclonal antibodies to the human IL-4 receptor alpha also bind to canine IL-4Rα.

Accordingly, chimeric human-canine antibodies against the IL-4 receptor alpha were constructed using the CDR sequences previously disclosed [see, Table 2 below] and then tested against canine IL-4Rα. Briefly, the VH and VL of each of a selected group of antibodies were genetically combined (fused) with the canine IgGB heavy chain constant regions (CH1-CH3) and light chain (kappa) constant region, respectively [see below for greater detail]. The human-canine (H-C) chimeras were transiently expressed in HEK293 cells and then purified using a Protein A column. The binding activities of the individual chimeric antibodies were tested on ELISA plates coded with canine IL-4Rα (cIL-4Rα). As the ELISA results in FIG. 1A show, whereas most of the human-canine chimeric antibodies could bind with some affinity for canine IL-4Rα, surprisingly, one particular chimeric antibody, Dupi H-C, demonstrated a significantly stonger affinity for canine IL-4Rα than any of the others.

Figure 1B:
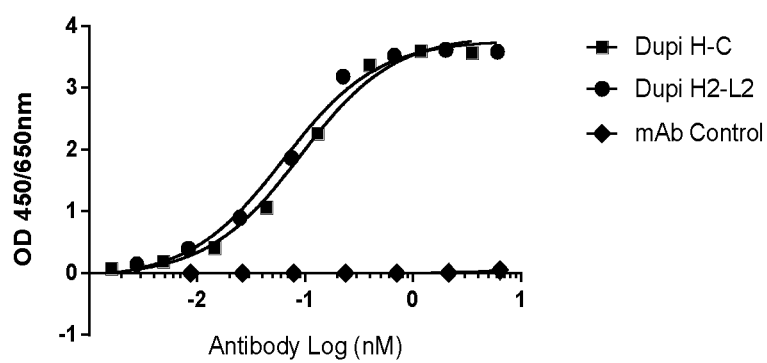
FIG. 1B shows the dose-dependent binding reactivity of chimeric human-canine antibody (Dupi H-C) and caninized monoclonal antibody (Dupi H2-L2) against canine IL-4 receptor alpha chain determined by ELISA. A monoclonal antibody raised against a canine antigen that is unrelated to cIL-4Rα was used as the control (mAb Control).

Afterwards a caninized antibody was constructed using the same CDRs as that of the Dupi H-C [see below for greater detail]. The binding activity of the chimeric (Dupi H-C) and caninized antibody (Dupi H2-L2) to canine IL-4 receptor alpha was compared by ELISA. As depicted in FIG. 1B, both the chimeric antibody and the caninized antibody show a strong affinity for canine IL-4Rα. In direct contrast, a control caninized monoclonal antibody (with CDRs obtained from a murine antibody raised against a non-related canine antigen) did not bind at all.

TABLE 2

PRIOR ART CDR SEQUENCES

| mAB | CDR | SEQUENCE | SEQ ID | CDR | SEQUENCE | SEQ ID |
|---|---|---|---|---|---|---|
| Dupi | L1 | RSSQSLLYSIGYNYLD | 43 | H1 | DYAMT | 46 |
|  | L2 | LGSNRAS | 44 | H2 | SISGSGGNTYYADSVKG | 47 |
|  | L3 | MQALQTPYT | 45 | H3 | DRLSITIRPRYYGLDV | 48 |
| M37 | L1 | SGGGSSIGQSYVS | 49 | H1 | SYYMH | 52 |
|  | L2 | DNNKRPS | 50 | H2 | IINPRGGSTSYAQKFQG | 53 |
|  | L3 | GTWDTSPVWEWP | 51 | H3 | GKYWMYD | 54 |
| 12B5 | L1 | RASQSVSSSYLA | 55 | H1 | RNAMF | 58 |
|  | L2 | GASSRAT | 56 | H2 | LIGTGGATNYADSVKG | 59 |
|  | L3 | QQYGSSPPWT | 57 | H3 | GRYYFDY | 60 |
| M1 | L1 | SGGSSNIGNSYVS | 65 | H1 | SYYMH | 68 |
|  | L2 | DNNKRPS | 66 | H2 | IINPSGGSTSYAQKFQG | 69 |
|  | L3 | GTWDTSLSANYV | 67 | H3 | GKWWLDY | 70 |

TABLE 2-continued

PRIOR ART CDR SEQUENCES

| mAB | CDR | SEQUENCE | SEQ ID | CDR | SEQUENCE | SEQ ID |
|---|---|---|---|---|---|---|
| M12 | L1 | SGGSSNIGNSYVS | 71 | H1 | SYYMH | 74 |
|  | L2 | DNNKRPS | 72 | H2 | IINPSGGSTSYAQKFQG | 75 |
|  | L3 | GTWDTSTTMYPL | 73 | H3 | GKWWFYD | 76 |
| 5A1 | L1 | RASQSVSSYLA | 77 | H1 | NFVMH | 80 |
|  | L2 | HASNRAT | 78 | H2 | AIGTGGGTYYADSVKG | 81 |
|  | L3 | QQRSNWPLT | 79 | H3 | DRPMVRGVIIDYFDY | 82 |
| 27A1 | L1 | RASQSVSSSYLA | 83 | H1 | RYGMH | 86 |
|  | L2 | GASSRAT | 84 | H2 | IIWFEGNNQYYADSVKG | 87 |
|  | L3 | QQYGSSPPWT | 85 | H3 | GKYYFDY | 88 |
| 63 | L1 | RASQGISTWLA | 89 | H1 | SYAMS | 92 |
|  | L2 | VASSLQS | 90 | H2 | SITGSGGSTYYADSVKG | 93 |
|  | L3 | QQANSFPFT | 91 | H3 | DNRGFFHY | 94 |

For the caninization or chimerization process, a IgG heavy chain had to be selected. There are four known IgG heavy chain subtypes of dog IgG, referred to as IgG-A, IgG-B, IgG-C, and IgG-D respectively, to choose from. The two known light chain subtypes are referred to as lambda and kappa. However, besides modulating the development of the canine Th2 immune response, a canine or caninized antibody against IL-4Rα optimally has two attributes:

1. lack of effector functions such as antibody-dependent cytotoxicity (ADCC) and complement-dependent cytotoxicity (CDC), and
2. be readily purified on a large scale using industry standard technologies such as that based on protein A chromatography.

None of the naturally occurring canine IgG isotypes satisfy both criteria [but see, WO 2015091910 A2; U.S. patent application Ser. No. 15/105,211, the contents of both of which are hereby incorporated by reference]. For example, IgG-B can be purified using protein A, but has a high level of ADCC activity. IgG-C also has considerable ADCC activity. On the other hand, IgG-A binds weakly to protein A, but displays undesirable ADCC activity. Moreover, neither IgG-C nor IgG-D can be purified on protein A columns, although IgG-D displays no ADCC activity. The present invention overcomes this difficulty by providing mutant canine IgG-B antibodies specific to IL-4Rα; such antibodies lack effector functions such as ADCC and can be readily be purified using industry standard protein A chromatography.

The IgG-B variants with reduced effector functions described encompass a first IgG-B variant in which an aspartic acid (D 277) and an asparagine (N 325) residue is each mutated to an alanine residue [cIgGB(−) ADCC], a second variant in which the hinge region of IgG-B is replaced by the hinge region of IgG-D [cIgGB(+) D-hinge], and a third variant in which the hinge region of IgG-B is replaced with the hinge region of IgG-A [cIgGB(+) A-hinge]. Additionally, the second and third variants also include replacement of the same aspartic acid and asparagine residues of the first variant with an alanine residue. The numbering of the aspartic acid and asparagine residues mutated in this invention is based on the numbering scheme described for canine IgG heavy chains in Tang et al., [*Vet Immunol and Immunopathol,* 80:259-270 (2001)].

```
Canine IgGB wt
                                    SEQ ID NO: 11
SASTTAPSVFPLAPSCGSTSGSTVALACLVSGYFPEPVTVSWNSGSLTSG

VHTFPSVLQSSGLYSLSSMVTVPSSRWPSETFTCNVAHPASKTKVDKPVP

KRENGRVPRPPDCPKCPAPEMLGGPSVFIFPPKPKDTLLIARTPEVTCVV

VDLDPEDPEVQISWFVDGKQMQTAKTQPREEQFNGTYRVVSVLPIGHQDW

LKGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKLS

VDKSRWQRGDTFICAVMHEALHNHYTQESLSHSPGK

Canine IgGB(+)A-hinge
                                    SEQ ID NO: 12
SASTTAPSVFPLAPSCGSTSGSTVALACLVSGYFPEPVTVSWNSGSLTSG

VHTFPSVLQSSGLYSLSSMVTVPSSRWPSETFTCNVAHPASKTKVDKPVF

NECRCTDTPPCPAPEMLGGPSVFIFPPKPKATLLIARTPEVTCVVVDLDP

EDPEVQISWFVDGKQMQTAKTQPREEQFAGTYRVVSVLPIGHQDWLKGKQ

FTCKVNNKALPSPIERTISKARGQAHQPSVYVLPPSREELSKNTVSLTCL

IKDFFPPDIDVEWQSNGQQEPESKYRTTPPQLDEDGSYFLYSKLSVDKSR

WQRGDTFICAVMHEALHNHYTQESLSHSPGK

Canine IgGB(+)D-hinge
                                    SEQ ID NO: 13
SASTTAPSVFPLAPSCGSTSGSTVALACLVSGYFPEPVTVSWNSGSLTSG

VHTFPSVLQSSGLYSLSSMVTVPSSRWPSETFTCNVAHPASKTKVDKPVP

KESTCKCISPCPAPEMLGGPSVFIFPPKPKATLLIARTPEVTCVVVDLDP

EDPEVQISWFVDGKQMQTAKTQPREEQFAGTYRVVSVLPIGHQDWLKGKQ

FTCKVNNKALPSPIERTISKARGQAHQPSVYVLPPSREELSKNTVSLTCL

IKDFFPPDIDVEWQSNGQQEPESKYRTTPPQLDEDGSYFLYSKLSVDKSR

WQRGDTFICAVMHEALHNHYTQESLSHSPGK

Canine IgGB(-)ADCC
                                    SEQ ID NO: 14
SASTTAPSVFPLAPSCGSTSGSTVALACLVSGYFPEPVTVSWNSGSLTSG

VHTFPSVLQSSGLYSLSSMVTVPSSRWPSETFTCNVAHPASKTKVDKPVP

KRENGRVPRPPDCPKCPAPEMLGGPSVFIFPPKPKATLLIARTPEVTCVV

VDLDPEDPEVQISWFVDGKQMQTAKTQPREEQFAGTYRVVSVLPIGHQDW

LKGKQFTCKVNNKALPSPIERTISKARGQAHQPSVYVLPPSREELSKNTV

SLTCLIKDFFPPDIDVEWQSNGQQEPESKYRTTPPQLDEDGSYFLYSKLS

VDKSRWQRGDTFICAVMHEALHNHYTQESLSHSPGK
```

Construction of Chimeric Anti-IL-4 Receptor Alpha Antibodies:

Once a modified canine constant heavy chain (CH1-CH3) was selected, a DNA sequence encoding the amino acid sequence of a heavy chain variable region of an anti-human IL-4 receptor alpha mAb [US 2015/0017176 A1] was fused to a DNA sequence of a modified canine constant heavy chain to produce a chimeric human-canine heavy chain DNA sequence, SEQ ID NO: 15. The encoded chimeric human-canine heavy chain comprises the amino acid sequence of SEQ ID NO: 16. Similarly, a DNA sequence encoding the amino acid sequence of a light chain variable region of an anti-human IL-4 receptor alpha mAb [US 2015/0017176 A1] was fused to a DNA sequence encoding the amino acid sequence of the constant canine kappa light chain to produce a chimeric human-canine light chain DNA sequence, SEQ ID NO: 17. The protein encoded by the chimeric human-canine light chain DNA sequence comprises the amino acid sequence of SEQ ID NO: 18.

Analogous chimeric constructs were made with a DNA sequence encoding the amino acid sequence of a heavy chain variable region of an anti-human IL-4 receptor alpha mAb [U.S. Pat. No. 8,877,189 B2] fused to a DNA sequence of a modified canine constant heavy chain: with the resulting chimeric human-canine heavy chain comprising the amino acid sequence of SEQ ID NO: 20, which is encoded by a nucleic acid comprising the nucleotide sequence of SEQ ID NO: 19; and the chimeric human-canine light chain comprising the amino acid sequence of SEQ ID NO: 22, which is encoded by a nucleic acid comprising the nucleotide sequence of SEQ ID NO: 21.

Similarly, chimeric constructs were made with a DNA sequence encoding the amino acid sequence of a heavy chain variable region of an anti-human IL-4 receptor alpha mAb [U.S. Pat. No. 7,186,809 B2] fused to a DNA sequence of a modified canine constant heavy chain: with the chimeric human-canine heavy chain encoded by a nucleic acid comprising the nucleotide sequence of SEQ ID NO: 23, and the corresponding chimeric antibody comprising the amino acid sequence of SEQ ID NO: 24; and the chimeric human-canine light chain encoded by a nucleic acid comprising the nucleotide sequence of SEQ ID NO: 25, and the corresponding chimeric antibody comprising the amino acid sequence of SEQ ID NO: 26.

The resulting chimeric human-canine heavy and light chains were cloned into separate expression plasmids using standard molecular biology techniques. Both plasmids were transfected into HEK 293 cells and the expressed antibody was purified from HEK 293 cell supernatant using protein A.

Construction of Chimeric Human-Canine Anti-IL4 Receptor Alpha Antibodies:

Without being bound by any specific approach, the process of producing variants of caninized anti-IL-4Rα mAbs with various contents of canine and human sequences involved the general following scheme:

i) Determine the DNA sequence of VH and VL chains of human mabs.

ii) Identify the H and L chain CDRs of human mabs.

iii) Identify a suitable H and L chain of canine IgG.

iv) Write down the DNA sequence of canine IgG H and L chains.

v) Replace the DNA sequence encoding endogenous canine H and L chain CDRs with DNA sequences encoding the respective human CDRs. Optionally, also replace some canine frame residues with selected residues from the corresponding human frame regions.

vi) Synthesize the DNA from step (v) and clone it into a suitable expression plasmid.

vii) Transfect plasmids into HEK 293 cells.

viii) Purify expressed antibody from HEK 293 supernatant.

ix) Test the purified antibody for binding to canine IL-4Rα.

The above outlined steps resulted in a set of variant antibodies with various contents of canine and human sequences.

Confirmation of Anti-Human IL-4 Receptor Alpha Monoclonal Antibody Reactivity Against Canine IL-4 Receptor Alpha:

The chimeric human-canine antibody encoded by SEQ ID NO: 16 and SEQ ID NO: 18 was tested for reactivity with the canine IL-4 receptor alpha as follows:
1. Coat 200 ng/well IL-4 receptor alpha in an immunoplate and incubate the plate at 4° C. overnight.
2. Wash the plate 3 times by PBS with 0.05% Tween 20 (PBST).
3. Block the plate by 0.5% BSA in PBS for 45-60 min at room temperature.
4. Wash the plate 3 times with PBST.
5. Three-fold dilute the chimeric antibody in each column or row of a dilution plate starting at 0.3 µg/mL.
6. Transfer the diluted chimeric antibody into each column or row of the immunoplate, and incubate the plate for 45-60 min at room temperature.
7. Wash the plate 3 times by PBST.
8. Add 1:4000 diluted horseradish peroxidase labeled anti-canine IgG into each well of the plate, and incubate the plate for 45-60 min at room temperature.
9. Wash the plate 3 times by PBST.
10. Add TMB substrate into each well of the plate, and incubate the plate for 10 to 15 min at room temperature to develop color.
11. Add 100 µL 1.5 M phosphoric acid into each well to stop the reaction.
12. Read the plate at 450 nm with 540 nm reference wavelength.

The human-canine chimeric IL-4Rα (Dupi mAb) antibody was assayed for reactivity with canine IL-4Rα by ELISA as described above. As shown in FIGS. 1A and 1B, the chimeric human-canine chimeric IL-4Rα antibody binds tightly to canine IL-4Rα in a dose-dependent manner.

```
Chimeric human-canine heavy chain DNA sequence (Dupi)
                                            [SEQ ID NO: 15]
GAGGTGCAGCTGGTGGAGTCCGGAGGAGGACTGGAGCAGCCCGGAGGAAGCCTGAGACTGAGC

TGCGCTGGCAGCGGCTTCACCTTCAGGGACTACGCCATGACCTGGGTGAGACAGGCCCCTGGC

AAGGGACTGGAGTGGGTGAGCAGCATCAGCGGCTCCGGCGGCAACACCTACTACGCCGACAGC

GTGAAGGGCAGGTTCACCATCAGCAGGGACAACAGCAAGAACACCCTGTACCTGCAGATGAAC

AGCCTGAGGGCCGAGGACACCGCCGTGTACTACTGCGCCAAGGACCGTTTATCTATCACCATC

AGGCCCAGGTACTACGGACTGGACGTGTGGGGCCAGGGCACCACAGTGACCGTGAGCAGCGCT

TCCACAACCGCGCCATCAGTCTTTCCGTTGGCCCCATCATGCGGGTCGACGAGCGGATCGACT

GTGGCCCTGGCGTGCTTGGTGTCGGGATACTTTCCCGAACCCGTCACGGTCAGCTGGAACTCC

GGATCGCTTACGAGCGGTGTGCATACGTTCCCCTCGGTCTTGCAATCATCAGGGCTCTACTCG

CTGTCGAGCATGGTAACGGTGCCCTCATCGAGGTGGCCCTCCGAAACGTTCACATGTAACGTA

GCACATCCAGCCTCCAAAACCAAGGTGGATAAACCCGTGCCGAAAAGAGAGAATGGGCGGGTG

CCTCGACCCCCTGATTGCCCCAAGTGTCCGGCTCCGGAAATGCTCGGTGGACCCTCAGTGTTT

ATCTTCCCTCCGAAGCCCAAGGACACTCTGCTGATCGCGCGCACTCCAGAAGTAACATGTGTA

GTGGTGGCACTTGATCCCGAGGACCCCGAAGTCCAGATCTCCTGGTTTGTAGATGGGAAACAG

ATGCAGACCGCAAAAACTCAACCCAGAGAGGAGCAGTTCGCAGGAACATACCGAGTGGTATCC

GTCCTTCCGATTGGCCACCAGGACTGGTTGAAAGGGAAGCAGTTTACGTGTAAAGTCAACAAT

AAGGCGTTGCCTAGCCCTATTGAGCGGACGATTTCGAAAGCTAGGGGACAGGCCCACCAGCCA

TCGGTCTATGTCCTTCCGCCTTCCCGCGAGGAGCTCTCGAAGAATACAGTGAGCCTTACATGC

CTCATTAAGGATTTCTTCCCGCCTGATATCGACGTAGAGTGGCAATCAAACGGTCAACAGGAG

CCGGAATCCAAGTATAGAACCACTCCGCCCCAGCTTGACGAGGACGGATCATACTTTTTGTAT

TCAAAACTGTCGGTGGATAAGAGCCGGTGGCAGAGAGGTGACACCTTCATCTGTGCGGTGATG

CACGAAGCACTCCATAATCACTACACCCAAGAGAGCCTCTCGCATTCCCCCGGAAAG

Chimeric human-canine heavy chain amino acid sequence (Dupi)
                                            [SEQ ID NO: 16]
EVQLVESGGGLEQPGGSLRLSCAGSGFTFRDYAMTWVRQAPGKGLEWVSSISGSGGNTYYADS

VKGRFTISRDNSKNTLYLQMNSLRAEDTAVYYCAKDRLSITIRPRYYGLDVWGQGTTVTVSSA

STTAPSVFPLAPSCGSTSGSTVALACLVSGYFPEPVTVSWNSGSLTSGVHTFPSVLQSSGLYS

LSSMVTVPSSRWPSETFTCNVAHPASKTKVDKPVPKRENGRVPRPPDCPKCPAPEMLGGPSVF

IFPPKPKDTLLIARTPEVTCVVVALDPEDPEVQISWFVDGKQMQTAKTQPREEQFAGTYRVVS
```

-continued

VLPIGHQDWLKGKQFTCKVNNKALPSPIERTISKARGQAHQPSVYVLPPSREELSKNTVSLTC

LIKDFFPPDIDVEWQSNGQQEPESKYRTTPPQLDEDGSYFLYSKLSVDKSRWQRGDTFICAVM

HEALHNHYTQESLSHSPGK
The human heavy chain variable region is in bold.

Chimeric human-canine light chain DNA sequence (Dupi)
[SEQ ID NO: 17]
GACATCGTGATGACCCAGAGCCCCCTGAGCCTGCCTGTGACACCTGGCGAGCCTGCCAGCATC

AGCTGCAGGTCCAGCCAGAGCCTGCTGTACAGCATCGGCTACAACTACCTGGACTGGTACCTG

CAGAAGAGCGGCCAGAGCCCCCAGCTGCTGATCTACCTGGGCAGCAATAGAGCCAGCGGCGTG

CCCGATAGATTTAGCGGCAGCGGCAGCGGCACAGACTTCACCCTGAAGATCAGCAGGGTGGAG

GCCGAGGACGTGGGCTTCTACTACTGCATGCAGGCCCTGCAGACCCCCTACACCTTCGGCCAG

GGCACCAAGCTGGAAATCAAGAGGAACGACGCTCAGCCAGCCGTGTACCTCTTCCAGCCTTCG

CCGGACCAGCTTCATACGGGGTCAGCGTCGGTGGTGTGCCTGTTGAACTCGTTTTACCCCAAG

GACATTAACGTGAAGTGGAAGGTAGACGGGGTAATTCAAGACACTGGCATTCAAGAGTCCGTC

ACGGAACAAGACTCAAAAGACTCAACGTATTCACTGTCGTCAACCTTGACGATGTCAAGCACC

GAGTATCTTAGCCATGAGCTGTATTCGTGCGAGATCACCCACAAGTCCCTCCCCTCCACTCTT

ATCAAATCCTTTCAGCGGTCGGAATGTCAGCGGGTCGAT

Chimeric human-canine light chain amino acid sequence Dupi)
[SEQ ID NO: 18]
DIVMTQSPLSLPVTPGEPASISC<u>RSSQSLLYSIGYNYLD</u>WYLQKSGQSPQLLIY<u>LGSNRASGV</u>

PDRFSGSGSGTDFTLKISRVEAEDVGFYYC<u>MQALQTPYT</u>FGQGTKLEIKRNDAQPAVYLFQPS

PDQLHTGSASVVCLLNSFYPKDINVKWKVDGVIQDTGIQESVTEQDSKDSTYSLSSTLTMSST

EYLSHELYSCEITHKSLPSTLIKSFQRSECQRVD
The human light chain variable region is in bold.

Chimeric canine heavy chain DNA sequence (M37):
[SEQ ID NO: 19]
CAGGTGCAGCTGGTGCAGAGCGGCGCCGAAGTGAAGAAGCCTGGCGCCAGCGTGAAGGTGAGC

TGCAAGGCCAGCGGCTACGCCTTCACCAGCTACTACATGCACTGGGCCAGACAGGCCCCTGGA

CAGGGACTGGAGTGGATGGGCATCATCAACCCTAGGGGCGGCAGCACCAGCTACGCCCAGAAG

TTCCAGGGCAGGGTGGCCATGACCAGGGACACCAGCACCAGCACCGTGTACATGGAACTGAGC

AGCCTGAGACCCGAGGACACCGCCGTGTACTACTGCGCCAGGGGCAAGTACTGGATGTACGAC

TGGGGCAAGGGCACCCTCGTGACCGTGAGCAGCGCTTCCACAACCGCGCCATCAGTCTTTCCG

TTGGCCCCATCATGCGGGTCGACGAGCGGATCGACTGTGGCCCTGGCGTGCTTGGTGTCGGA

TACTTTCCCGAACCCGTCACGGTCAGCTGGAACTCCGGATCGCTTACGAGCGGTGTGCATACG

TTCCCCTCGGTCTTGCAATCATCAGGGCTCTACTCGCTGTCGAGCATGGTAACGGTGCCCTCA

TCGAGGTGGCCCTCCGAAACGTTCACATGTAACGTAGCACATCCAGCCTCCAAAACCAAGGTG

GATAAACCCGTGCCGAAAAGAGAGAATGGGCGGGTGCCTCGACCCCCTGATTGCCCCAAGTGT

CCGGCTCCGGAAATGCTCGGTGGACCCTCAGTGTTTATCTTCCCTCCGAAGCCCAAGGACACT

CTGCTGATCGCGCGCACTCCAGAAGTAACATGTGTAGTGGTGGCACTTGATCCCGAGGACCCC

GAAGTCCAGATCTCCTGGTTTGTAGATGGGAACAGATGCAGACCGCAAAAACTCAACCCAGA

GAGGAGCAGTTCGCAGGAACATACCGAGTGGTATCCGTCCTTCCGATTGGCCACCAGGACTGG

TTGAAAGGGAAGCAGTTTACGTGTAAAGTCAACAATAAGGCGTTGCCTAGCCCTATTGAGCGG

ACGATTTCGAAAGCTAGGGGACAGGCCCACCAGCCATCGGTCTATGTCCTTCCGCCTTCCCGC

GAGGAGCTCTCGAAGAATACAGTGAGCCTTACATGCCTCATTAAGGATTTCTTCCCGCCTGAT

ATCGACGTAGAGTGGCAATCAAACGGTCAACAGGAGCCGGAATCCAAGTATAGAACCACTCCG

-continued

CCCCAGCTTGACGAGGACGGATCATACTTTTTGTATTCAAAACTGTCGGTGGATAAGAGCCGG

TGGCAGAGAGGTGACACCTTCATCTGTGCGGTGATGCACGAAGCACTCCATAATCACTACACC

CAAGAGAGCCTCTCGCATTCCCCCGGAAAG
The human heavy chain variable region is in bold.

Chimeric canine heavy chain amino acid sequence (M37):
[SEQ ID NO: 20]
QVQLVQSGAEVKKPGASVKVSCKASGYAF<u>TSYYMH</u>WARQAPGQGLEWMGI<u>INPRGGSTSYAQK</u>

<u>FQ</u>GRVAMTRDTSTSTVYMELSSLRPEDTAVYYCAR<u>GKYWMYD</u>WGKGTLVTVSSASTTAPSVFP

LAPSCGSTSGSTVALACLVSGYFPEPVTVSWNSGSLTSGVHTFPSVLQSSGLYSLSSMVTVPS

SRWPSETFTCNVAHPASKTKVDKPVPKRENGRVPRPPDCPKCPAPEMLGGPSVFIFPPKPKDT

LLIARTPEVTCVVVALDPEDPEVQISWFVDGKQMQTAKTQPREEQFAGTYRVVSVLPIGHQDW

LKGKQFTCKVNNKALPSPIERTISKARGQAHQPSVYVLPPSREELSKNTVSLTCLIKDFFPPD

IDVEWQSNGQQEPESKYRTTPPQLDEDGSYFLYSKLSVDKSRWQRGDTFICAVMHEALHNHYT

QESLSHSPGK
The human heavy chain variable region is in bold.

Chimeric canine light chain DNA sequence (M37):
[SEQ ID NO: 21]
CAGAGCGTGCTGACCCAGCCTCCTAGCGTGAGCGCCGCTCCCGGCCAGAAAGTGACCATCAGC

TGCAGCGGCGGCGGAAGCAGCATCGGCAACAGCTACGTGTCCTGGTACCAGCAGCTGCCCGGA

ACCGCCCCTAAGCTGCTGATCTACGACAACAACAAGAGGCCCTCCGGCGTGCCCGACAGATTT

AGCGGCAGCAAGAGCGGCACCAGCGCCACACTGGCCATCACAGGCCTGCAGACCGGCGATGAG

GCCGACTACTACTGCGGCACCTGGGACACAAGCCCTGTGTGGGAATGGCCCTTCGGCACCGGC

ACCAAGCTGACCGTGCTGAGGAACGACGCTCAGCCAGCCGTGTACCTCTTCCAGCCTTCGCCG

GACCAGCTTCATACGGGGTCAGCGTCGGTGGTGTGCCTGTTGAACTCGTTTTACCCCAAGGAC

ATTAACGTGAAGTGGAAGGTAGACGGGGTAATTCAAGACACTGGCATTCAAGAGTCCGTCACG

GAACAAGACTCAAAAGACTCAACGTATTCACTGTCGTCAACCTTGACGATGTCAAGCACCGAG

TATCTTAGCCATGAGCTGTATTCGTGCGAGATCACCCACAAGTCCCTCCCCTCCACTCTTATC

AAATCCTTTCAGCGGTCGGAATGTCAGCGGGTCGAT
The human light chain variable region is in bold.

Chimeric canine light chain amino acid sequence (M37):
[SEQ ID NO: 22]
QSVLTQPPSVSAAPGQKVTISC<u>SGGGSSIGNSYVS</u>WYQQLPGTAPKLLIY<u>DNNKRPSGVPDRF</u>

SGSKSGTSATLAITGLQTGDEADYYC<u>GTWDTSPVWEWP</u>FGTGTKLTVLRNDAQPAVYLFQPSP

DQLHTGSASVVCLLNSFYPKDINVKWKVDGVIQDTGIQESVTEQDSKDSTYSLSSTLTMSSTE

YLSHELYSCEITHKSLPSTLIKSFQRSECQRVD
The human light chain variable region is in bold.

Chimeric canine heavy chain DNA sequence (12B5):
[SEQ ID NO: 23]
GAGGTGCAGCTGGTGCAGAGCGGAGGCGGACTGGTGCATCCCGGAGGAAGCCTGAGACTGTCC

TGCGCCGGCAGCGGCTTCACCTTCAGCAGGAACGCCATGTTCTGGGTGAGACAGGCCCCCGGC

AAGGGACTGGAATGGGTGAGCCTGATCGGAACCGGAGGCGCCACCAACTACGCCGACAGCGTG

AAGGGCAGGTTCACCATCAGCAGGGACAACGCCAAGAACAGCCTGTACCTGCAGATGAACAGC

CTGAGGGCCGAGGACATGGCCGTGTACTACTGCGCCAGGGGCAGGTACTACTTCGACTATTGG

GGCCAGGGCACCCTCGTGACCGTGTCCAGCGCTTCCACAACCGCGCCATCAGTCTTTCCGTTG

GCCCCATCATGCGGGTCGACGAGCGGATCGACTGTGGCCCTGGCGTGCTTGGTGTCGGGATAC

TTTCCCGAACCCGTCACGGTCAGCTGGAACTCCGGATCGCTTACGAGCGGTGTGCATACGTTC

-continued

```
CCCTCGGTCTTGCAATCATCAGGGCTCTACTCGCTGTCGAGCATGGTAACGGTGCCCTCATCG

AGGTGGCCCTCCGAAACGTTCACATGTAACGTAGCACATCCAGCCTCCAAAACCAAGGTGGAT

AAACCCGTGCCGAAAAGAGAGAATGGGCGGGTGCCTCGACCCCCTGATTGCCCCAAGTGTCCG

GCTCCGGAAATGCTCGGTGGACCCTCAGTGTTTATCTTCCCTCCGAAGCCCAAGGACACTCTG

CTGATCGCGCGCACTCCAGAAGTAACATGTGTAGTGGTGGCACTTGATCCCGAGGACCCCGAA

GTCCAGATCTCCTGGTTTGTAGATGGGAAACAGATGCAGACCGCAAAAACTCAACCCAGAGAG

GAGCAGTTCGCAGGAACATACCGAGTGGTATCCGTCCTTCCGATTGGCCACCAGGACTGGTTG

AAAGGGAAGCAGTTTACGTGTAAAGTCAACAATAAGGCGTTGCCTAGCCCTATTGAGCGGACG

A11TCGAAAGCTAGGGGACAGGCCCACCAGCCATCGGTCTATGTCCTTCCGCCTTCCCGCGAG

GAGCTCTCGAAGAATACAGTGAGCCTTACATGCCTCATTAAGGATTTCTTCCCGCCTGATATC

GACGTAGAGTGGCAATCAAACGGTCAACAGGAGCCGGAATCCAAGTATAGAACCACTCCGCCC

CAGCTTGACGAGGACGGATCATACTTTTTGTATTCAAAACTGTCGGTGGATAAGAGCCGGTGG

CAGAGAGGTGACACCTTCATCTGTGCGGTGATGCACGAAGCACTCCATAATCACTACACCCAA

GAGAGCCTCTCGCATTCCCCCGGAAAG
```
The human heavy chain variable region is in bold.

Chimeric canine heavy chain amino acid sequence (12B5):
[SEQ ID NO: 24]

EVQLVQSGGGLVHPGGSLRLSCAGSGFTFS<u>RNAMF</u>WVRQAPGKGLEWVS<u>LIGTGGATNYADSV</u>

<u>KG</u>RFTISRDNAKNSLYLQMNSLRAEDMAVYYCAR<u>GRYYFDY</u>WGQGTLVTVSSASTTAPSVFPL

APSCGSTSGSTVALACLVSGYFPEPVTVSWNSGSLTSGVHTFPSVLQSSGLYSLSSMVTVPSS

RWPSETFTCNVAHPASKTKVDKPVPKRENGRVPRPPDCPKCPAPEMLGGPSVFIFPPKPKDTL

LIARTPEVTCVVVALDPEDPEVQISWFVDGKQMQTAKTQPREEQFAGTYRVVSVLPIGHQDWL

KGKQFTCKVNNKALPSPIERTISKARGQAHQPSVYVLPPSREELSKNTVSLTCLIKDFFPPDI

DVEWQSNGQQEPESKYRTTPPQLDEDGSYFLYSKLSVDKSRWQRGDTFICAVMHEALHNHYTQ

ESLSHSPGK

The human heavy chain variable region is in bold.

Chimeric canine light chain DNA sequence (12B5):
[SEQ ID NO: 25]

GAGATCGTGCTGACCCAGAGCCCTGGCACACTGAGCCTGAGCCCCGGAGAGAGGGCTACCCTG

AGCTGCAGGGCCAGCCAGAGCGTGAGCAGCAGCTACCTGGCCTGGTACCAGCAGAAACCCGGC

CAGGCCCCCAGACTGCTGATCTTTGGCGCCAGCAGCAGAGCCACCGGCATCCCCGATAGATTT

AGCGGCAGCGGCAGCGGCACCGACTTTACCCTGACCATCAGCAGGCTGGAGCCCGAGGACTTC

GCCGTGTACTACTGCCAGCAGTACGGCAGCAGCCCTCCTTGGACCTTCGGCCAGGGCACCAAG

GTGGAGATCAAGAGGAACGACGCTCAGCCAGCCGTGTACCTCTTCCAGCCTTCGCCGGACCAG

CTTCATACGGGGTCAGCGTCGGTGGTGTGCCTGTTGAACTCGTTTTACCCCAAGGACATTAAC

GTGAAGTGGAAGGTAGACGGGGTAATTCAAGACACTGGCATTCAAGAGTCCGTCACGGAACAA

GACTCAAAAGACTCAACGTATTCACTGTCGTCAACCTTGACGATGTCAAGCACCGAGTATCTT

AGCCATGAGCTGTATTCGTGCGAGATCACCCACAAGTCCCTCCCCTCCACTCTTATCAAATCC

TTTCAGCGGTCGGAATGTCAGCGGGTCGAT

The human light chain variable region is in bold.

Chimeric canine light chain amino acid sequence (12B5):
[SEQ ID NO: 26]

EIVLTQSPGTLSLSPGERATLSC<u>RASQSVSSSYLA</u>WYQQKPGQAPRLLIF<u>GASSRATG</u>IPDRF

SGSGSGTDFTLTISRLEPEDFAVYYC<u>QQYGSSPPWT</u>FGQGTKVEIKRNDAQPAVYLFQPSPDQ

```
LHTGSASVVCLLNSFYPKDINVKWKVDGVIQDTGIQESVTEQDSKDSTYSLSSTLTMSSTEYL

SHELYSCEITHKSLPSTLIKSFQRSECQRVD
The human light chain variable region is in bold
```

Example 3

Caninized Human Anti-Human IL-4Rα Monoclonal Antibodies

Without being bound by any specific approach, the overall process of producing caninized heavy and light chains that can be mixed in different combinations to produce caninized anti-canine IL-4Rα mAbs can be accomplished with the following protocol:

i) Identify the CDRs of Heavy (H) and Light (L) chains of a known anti-human IL-4Rα monal clonal antibody (mAb). Back translate the amino acid sequences of the CDRs into a suitable DNA sequence.

ii) Identify a suitable DNA sequence for the H and L chain of canine IgG (e.g., a heavy chain of IgG-B and light kappa chain).

iii) Identify the DNA sequences encoding the endogenous CDRs of canine IgG H and L chains DNA of the above sequence.

iv) Replace the DNA sequence encoding endogenous canine H and L chain CDRs with DNA sequences encoding the desired anti-IL-4Rα CDRs. Optionally also replace the DNA encoding some canine framework amino acid residues with DNA encoding selected amino acid residues from the desired anti-IL-4Rα mAb framework regions.

v) Synthesize the DNA from step (iv) and clone it into a suitable expression plasmid.

vi) Transfect the plasmids containing the desired caninized H and L chains into HEK 293 cells.

vii) Purify the expressed caninized antibody from the HEK 293 supernatant.

viii) Test purified caninized antibody for binding to canine IL-4Rα.

Three (3) caninized H and three (3) caninized L chain nucleotide and amino acid sequences were thus obtained and are provided below. The present invention provides caninized antibodies formed by the combination of one of the three caninized heavy chains with one of the three caninized light chains. In particular embodiments of this type, the resulting antibody is selected for the tightest binding with IL-4Rα.

The Fc portion of the above caninized antibodies is based on a modified sequences of canine IgG-B in order to remove ADCC and CDC effector functions as indicated above, as well as in U.S. provisional application 62/310,250, filed Mar. 18, 2016, the contents of which are hereby incorporated by reference [see also, WO 2015091910 A2 and U.S. patent application Ser. No. 15/105,211, the contents of both of which are hereby incorporated by reference]. In addition, the Fc's of these caninized antibodies may be replaced with modified Fc from other canine IgG isotypes as disclosed above and in U.S. provisional application 62/310,250, U.S. patent application Ser. No. 15/105,211, and in WO 2015091910 A2.

DNA and Protein Sequences for Caninized Anti-Canine IL-4 Receptor mAbs:

```
Caninized Dupi heavy chain (H1) nucleotide sequence
                                                SEQ ID NO: 27
GAGGTGCAGCTGGTGGAGAGCGGCGGAGACCTGGTGAAGCCTGGAGGCAGCCTGAGACTGAGCTGCGTG

GCCAGCGGCTTCACCTTCAGGGACTACGCCATGACCTGGGTGAGGCAGGCTCCTGGAAAGGGCCTGCAGT

GGGTGGCCTCCATTAGCGGCAGCGGCGGCAACACATACTACGCCGACAGCGTGAAGGGCAGGTTCACCA

TCAGCAGGGACAACGCCAAGAACACCCTGTACCTGCAGATGAACAGCCTGAGGGCCGAGGACACCGCCG

TGTACTACTGCACCAGGGACAGGCTGTCCATCACCATCAGGCCCAGGTACTACGGCCTGGATGTGTGGGG

CCAGGGCACACTGGTGACCGTGAGCAGCGCTTCCACAACCGCGCCATCAGTCTTTCCGTTGGCCCCATCAT

GCGGGTCGACGAGCGGATCGACTGTGGCCCTGGCGTGCTTGGTGTCGGGATACTTTCCCGAACCCGTCAC

GGTCAGCTGGAACTCCGGATCGCTTACGAGCGGTGTGCATACGTTCCCCTCGGTCTTGCAATCATCAGGGC

TCTACTCGCTGTCGAGCATGGTAACGGTGCCCTCATCGAGGTGGCCCTCCGAAACGTTCACATGTAACGTA

GCACATCCAGCCTCCAAAACCAAGGTGGATAAACCCGTGCCGAAAAGAGAGAATGGGCGGGTGCCTCGA

CCCCCTGATTGCCCCAAGTGTCCGGCTCCGGAAATGCTCGGTGGACCCTCAGTGTTTATCTTCCCTCCGAA

GCCCAAGGACACTCTGCTGATCGCGCGCACTCCAGAAGTAACATGTGTAGTGGTGGCACTTGATCCCGAG

GACCCCGAAGTCCAGATCTCCTGGTTTGTAGATGGGAAACAGATGCAGACCGCAAAAACTCAACCCAGAG

AGGAGCAGTTCGCAGGAACATACCGAGTGGTATCCGTCCTTCCGATTGGCCACCAGGACTGGTTGAAAGG

GAAGCAGTTTACGTGTAAAGTCAACAATAAGGCGTTGCCTAGCCCTATTGAGCGGACGATTTCGAAAGCT

AGGGGACAGGCCCACCAGCCATCGGTCTATGTCCTTCCGCCTTCCCGCGAGGAGCTCTCGAAGAATACAG

TGAGCCTTACATGCCTCATTAAGGATTTCTTCCCGCCTGATATCGACGTAGAGTGGCAATCAAACGGTCAA
```

-continued

CAGGAGCCGGAATCCAAGTATAGAACCACTCCGCCCCAGCTTGACGAGGACGGATCATACTTTTTGTATT

CAAAACTGTCGGTGGATAAGAGCCGGTGGCAGAGAGGTGACACCTTCATCTGTGCGGTGATGCACGAAGC

ACTCCATAATCACTACACCCAAGAGAGCCTCTCGCATTCCCCCGGAAAG

Caninized Dupi heavy chain (H1) amino acid sequence

SEQ ID NO: 28

EVQLVESGGDLVKPGGSLRLSCVASGFTFR<u>DYAMT</u>WVRQAPGKGLQWVA<u>SISGSGGNTYYADSVKG</u>RFTISR

DNAKNTLYLQMNSLRAEDTAVYYCTR<u>DRLSITIRPRYYGLDV</u>WGQGTLVTVSSASTTAPSVFPLAPSCGSTSG

STVALACLVSGYFPEPVTVSWNSGSLTSGVHTFPSVLQSSGLYSLSSMVTVPSSRWPSETFTCNVAHPASKTKV

DKPVPKRENGRVPRPPDCPKCPAPEMLGGPSVFIFPPKPKDTLLIARTPEVTCVVVALDPEDPEVQISWFVDGK

QMQTAKTQPREEQFAGTYRVVSVLPIGHQDWLKGKQFTCKVNNKALPSPIERTISKARGQAHQPSVYVLPPSR

EELSKNTVSLTCLIKDFFPPDIDVEWQSNGQQEPESKYRTTPPQLDEDGSYFLYSKLSVDKSRWQRGDTFICAV

MHEALHNHYTQESLSHSPGK

Caninized Dupi heavy chain (H2) nucleotide sequence

SEQ ID NO: 29

GAGGTGCAGCTGGTGGAGAGCGGCGGCGATCTGGTGAAGCCTGGAGGCAGCCTGAGACTGAGCTGCGCC

GGAAGCGGCTTCACCTTCAGGGACTACGCCATGACCTGGGTGAGACAGGCCCCTGGAAAGGGCCTGCAGT

GGGTGAGCAGCATCTCCGGCAGCGGCGGCAACACCTACTACGCCGACAGCGTGAAGGGCAGGTTCACCA

TCAGCAGGGACAACGCCAAGAACACCCTGTACCTGCAGATGAACAGCCTGAGGGCCGAGGACACCGCCG

TGTACTACTGCGCCAAGGACAGACTGAGCATCACCATCAGGCCCAGGTACTACGGCCTGGACGTGTGGGG

ACAGGGCACACTGGTGACCGTGAGCAGCGCTTCCACAACCGCGCCATCAGTCTTTCCGTTGGCCCCATCA

TGCGGGTCGACGAGCGGATCGACTGTGGCCCTGGCGTGCTTGGTGTCGGGATACTTTCCCGAACCCGTCA

CGGTCAGCTGGAACTCCGGATCGCTTACGAGCGGTGTGCATACGTTCCCCTCGGTCTTGCAATCATCAGGG

CTCTACTCGCTGTCGAGCATGGTAACGGTGCCCTCATCGAGGTGGCCCTCCGAAACGTTCACATGTAACGT

AGCACATCCAGCCTCCAAAACCAAGGTGGATAAACCCGTGCCGAAAAGAGAGAATGGGCGGGTGCCTCG

ACCCCCTGATTGCCCCAAGTGTCCGGCTCCGGAAATGCTCGGTGGACCCTCAGTGTTTATCTTCCCTCCGA

AGCCCAAGGACACTCTGCTGATCGCGCGCACTCCAGAAGTAACATGTGTAGTGGTGGCACTTGATCCCGA

GGACCCCGAAGTCCAGATCTCCTGGTTTGTAGATGGGAAACAGATGCAGACCGCAAAAACTCAACCCAGA

GAGGAGCAGTTCGCAGGAACATACCGAGTGGTATCCGTCCTTCCGATTGGCCACCAGGACTGGTTGAAAG

GGAAGCAGTTTACGTGTAAAGTCAACAATAAGGCGTTGCCTAGCCCTATTGAGCGGACGATTTCGAAAGC

TAGGGGACAGGCCCACCAGCCATCGGTCTATGTCCTTCCGCCTTCCCGCGAGGAGCTCTCGAAGAATACA

GTGAGCCTTACATGCCTCATTAAGGATTTCTTCCCGCCTGATATCGACGTAGAGTGGCAATCAAACGGTCA

ACAGGAGCCGGAATCCAAGTATAGAACCACTCCGCCCCAGCTTGACGAGGACGGATCATACTTTTTGTAT

TCAAAACTGTCGGTGGATAAGAGCCGGTGGCAGAGAGGTGACACCTTCATCTGTGCGGTGATGCACGAAG

CACTCCATAATCACTACACCCAAGAGAGCCTCTCGCATTCCCCCGGAAAG

Caninized Dupi heavy chain (H2) amino acid sequence

SEQ ID NO: 30

EVQLVESGGDLVKPGGSLRLSCAGSGFTFR<u>DYAMT</u>WVRQAPGKGLQWVS<u>SISGSGGNTYYADSVKG</u>RFTISR

DNAKNTLYLQMNSLRAEDTAVYYCAK<u>DRLSITIRPRYYGLDV</u>WGQGTLVTVSSASTTAPSVFPLAPSCGSTSG

STVALACLVSGYFPEPVTVSWNSGSLTSGVHTFPSVLQSSGLYSLSSMVTVPSSRWPSETFTCNVAHPASKTKV

DKPVPKRENGRVPRPPDCPKCPAPEMLGGPSVFIFPPKPKDTLLIARTPEVTCVVVALDPEDPEVQISWFVDGK

QMQTAKTQPREEQFAGTYRVVSVLPIGHQDWLKGKQFTCKVNNKALPSPIERTISKARGQAHQPSVYVLPPSR

EELSKNTVSLTCLIKDFFPPDIDVEWQSNGQQEPESKYRTTPPQLDEDGSYFLYSKLSVDKSRWQRGDTFICAV

MHEALHNHYTQESLSHSPGK

-continued

Caninized Dupi heavy chain (H3) nucleotide sequence
SEQ ID NO: 31
GAGGTGCAGCTGGTGGAGAGCGGCGGCGATCTGGTGAAGCCTGGCGGAAGCCTGAGACTGAGCTGTGCC

GGCAGCGGCTTCACCTTCAGGGACTACGCCATGACCTGGGTGAGACAGGCCCCTGGCAAAGGCCTGGAGT

GGGTGAGCAGCATCAGCGGCAGCGGCGGCAACACCTACTACGCCGACAGCGTGAAGGGCAGGTTCACCA

TCTCCAGGGACAACAGCAAGAACACCCTGTACCTGCAGATGAACAGCCTGAGGGCCGAGGATACCGCCG

TGTACTACTGCGCCAAGGACAGACTGAGCATCACCATCAGGCCCAGGTACTACGGACTGGATGTGTGGGG

CCAGGGCACCCTCGTGACCGTGTCCAGCGCTTCCACAACCGCGCCATCAGTCTTTCCGTTGGCCCCATCAT

GCGGGTCGACGAGCGGATCGACTGTGCCCTGGCGTGCTTGGTGTCGGGATACTTTCCCGAACCCGTCAC

GGTCAGCTGGAACTCCGGATCGCTTACGAGCGGTGTGCATACGTTCCCCTCGGTCTTGCAATCATCAGGGC

TCTACTCGCTGTCGAGCATGGTAACGGTGCCCTCATCGAGGTGGCCCTCCGAAACGTTCACATGTAACGTA

GCACATCCAGCCTCCAAAACCAAGGTGGATAAACCCGTGCCGAAAAGAGAGAATGGGCGGGTGCCTCGA

CCCCCTGATTGCCCCAAGTGTCCGGCTCCGGAAATGCTCGGTGGACCCTCAGTGTTTATCTTCCCTCCGAA

GCCCAAGGACACTCTGCTGATCGCGCGCACTCCAGAAGTAACATGTGTAGTGGTGGCACTTGATCCCGAG

GACCCCGAAGTCCAGATCTCCTGGTTTGTAGATGGGAAACAGATGCAGACCGCAAAAACTCAACCCAGAG

AGGAGCAGTTCGCAGGAACATACCGAGTGGTATCCGTCCTTCCGATTGGCCACCAGGACTGGTTGAAAGG

GAAGCAGTTTACGTGTAAAGTCAACAATAAGGCGTTGCCTAGCCCTATTGAGCGGACGATTTCGAAAGCT

AGGGGACAGGCCCACCAGCCATCGGTCTATGTCCTTCCGCCTTCCCGCGAGGAGCTCTCGAAGAATACAG

TGAGCCTTACATGCCTCATTAAGGATTTCTTCCCGCCTGATATCGACGTAGAGTGGCAATCAAACGGTCAA

CAGGAGCCGGAATCCAAGTATAGAACCACTCCGCCCCAGCTTGACGAGGACGGATCATACTTTTTGTATT

CAAAACTGTCGGTGGATAAGAGCCGGTGGCAGAGAGGTGACACCTTCATCTGTGCGGTGATGCACGAAGC

ACTCCATAATCACTACACCCAAGAGAGCCTCTCGCATTCCCCCGGAAAG

Caninized Dupi heavy chain (H3) amino acid sequence
SEQ ID NO: 32
EVQLVESGGDLVKPGGSLRLSCAGSGFTFR<u>DYAMT</u>WVRQAPGKGLEWVS<u>SISGSGGNTYYADSVKG</u>RFTISR DNSKNTLYLQMNSLRAEDTAVYYCAK<u>DRLSITIRPRYYGLDV</u>WGQGTLVTVSSASTTAPSVFPLAPSCGSTSG

STVALACLVSGYFPEPVTVSWNSGSLTSGVHTFPSVLQSSGLYSLSSMVTVPSSRWPSETFTCNVAHPASKTKV

DKPVPKRENGRVPRPPDCPKCPAPEMLGGPSVFIFPPKPKDTLLIARTPEVTCVVVALDPEDPEVQISWFVDGK

QMQTAKTQPREEQFAGTYRVVSVLPIGHQDWLKGKQFTCKVNNKALPSPIERTISKARGQAHQPSVYVLPPSR

EELSKNTVSLTCLIKDFFPPDIDVEWQSNGQQEPESKYRTTPPQLDEDGSYFLYSKLSVDKSRWQRGDTFICAV

MHEALHNHYTQESLSHSPGK

CANINIZED DUPI light chain (L1) nucleotide sequence
SEQ ID NO: 33
GACATTGTGATGACCCAGACCCCTCTGAGCCTGTCCGTGAGCCCTGGCGAGCCTGCTAGCATCAGCTGCA

GGAGCAGCCAGAGCCTGCTGTACAGCATCGGCTACAACTACCTGGACTGGTTCAGGCAGAAGCCCGGCCA

GAGCCCTCAGAGGCTGATCTACCTGGGAAGCAACAGGGCCAGCGGCGTGCCTGACAGGTTTAGCGGCAG

CGGCAGCGGCACCGATTTCACCCTGAGGATCAGCAGAGTGGAGGCCGATGACGCCGGCGTGTACTACTGC

ATGCAGGCCCTGCAGACCCCCTACACCTTCGGCCAGGGCACCAAGGTGGAGATCAAGAGGAACGACGCT

CAGCCAGCCGTGTACCTCTTCCAGCCTTCGCCGGACCAGCTTCATACGGGGTCAGCGTCGGTGGTGTGCCT

GTTGAACTCGTTTTACCCCAAGGACATTAACGTGAAGTGGAAGGTAGACGGGGTAATTCAAGACACTGGC

ATTCAAGAGTCCGTCACGGAACAAGACTCAAAAGACTCAACGTATTCACTGTCGTCAACCTTGACGATGT

CAAGCACCGAGTATCTTAGCCATGAGCTGTATTCGTGCGAGATCACCCACAAGTCCCTCCCCTCCACTCTT

ATCAAATCCTTTCAGCGGTCGGAATGTCAGCGGGTCGAT

CANINIZED DUPI light chain (L1) amino acid sequence
SEQ ID NO: 34
DIVMTQTPLSLSVSPGEPASISCRSSQSLLYSIGYNYLDWFRQKPGQSPQRLIYLGSNRASGVPDRFSGSGSGTDF

TLRISRVEADDAGVYYCMQALQTPYTFGQGTKVEIKRNDAQPAVYLFQPSPDQLHTGSASVVCLLNSFYPKDI

NVKWKVDGVIQDTGIQESVTEQDSKDSTYSLSSTLTMSSTEYLSHELYSCEITHKSLPSTLIKSFQRSECQRVD

CANINIZED DUPI light chain (L2) nucleotide sequence
SEQ ID NO: 35
GACATCGTGATGACCCAGACCCCTCTGAGCCTGAGCGTGAGCCCTGGAGAGCCCGCCAGCATCTCCTGCA

GAAGCAGCCAGAGCCTGCTGTACAGCATCGGCTACAACTACCTGGACTGGTACCTGCAGAAGCCCGGCCA

GAGCCCTCAGCTGCTGATCTACCTGGGCAGCAACAGAGCCAGCGGCGTGCCTGACAGATTTAGCGGCAGC

GGCAGCGGCACAGACTTCACCCTGAGGATCAGCAGAGTGGAGGCCGACGATGCCGGCGTGTACTACTGC

ATGCAGGCCCTGCAGACCCCCTACACCTTCGGCCAGGGCACCAAGGTGGAGATCAAGAGGAACGACGCT

CAGCCAGCCGTGTACCTCTTCCAGCCTTCGCCGGACCAGCTTCATACGGGGTCAGCGTCGGTGGTGTGCCT

GTTGAACTCGTTTTACCCCAAGGACATTAACGTGAAGTGGAAGGTAGACGGGGTAATTCAAGACACTGGC

ATTCAAGAGTCCGTCACGGAACAAGACTCAAAAGACTCAACGTATTCACTGTCGTCAACCTTGACGATGT

CAAGCACCGAGTATCTTAGCCATGAGCTGTATTCGTGCGAGATCACCCACAAGTCCCTCCCCTCCACTCTT

ATCAAATCCTTTCAGCGGTCGGAATGTCAGCGGGTCGAT

CANINIZED DUPI light chain (L2) amino acid sequence
SEQ ID NO: 36
DIVMTQTPLSLSVSPGEPASISCRSSQSLLYSIGYNYLDWYLQKPGQSPQLLIYLGSNRASGVPDRFSGSGSGTDF

TLRISRVEADDAGVYYCMQALQTPYTFGQGTKVEIKRNDAQPAVYLFQPSPDQLHTGSASVVCLLNSFYPKDI

NVKWKVDGVIQDTGIQESVTEQDSKDSTYSLSSTLTMSSTEYLSHELYSCEITHKSLPSTLIKSFQRSECQRVD

CANINIZED DUPI light chain (L3) nucleotide sequence
SEQ ID NO: 37
GACATCGTGATGACCCAGACACCCCTGAGCCTGAGCGTGAGCCCTGGCGAACCTGCCAGCATCAGCTGCA

GGAGCTCCCAGAGCCTGCTGTACAGCATCGGCTACAACTACCTCGACTGGTACCTGCAGAAGCCCGGCCA

GAGCCCTCAGCTGCTGATCTACCTGGGCTCCAACAGAGCCAGCGGCGTGCCTGACAGATTTAGCGGCAGC

GGCAGCGGAACCGACTTCACCCTGAGGATCAGCAGAGTGGAGGCCGACGACGCCGGCTTCTACTACTGCA

TGCAGGCCCTGCAGACCCCCTACACCTTCGGCCAGGGCACCAAGCTGGAGATCAAGAGGAACGACGCTC

AGCCAGCCGTGTACCTCTTCCAGCCTTCGCCGGACCAGCTTCATACGGGGTCAGCGTCGGTGGTGTGCCTG

TTGAACTCGTTTTACCCCAAGGACATTAACGTGAAGTGGAAGGTAGACGGGGTAATTCAAGACACTGGCA

TTCAAGAGTCCGTCACGGAACAAGACTCAAAAGACTCAACGTATTCACTGTCGTCAACCTTGACGATGTC

AAGCACCGAGTATCTTAGCCATGAGCTGTATTCGTGCGAGATCACCCACAAGTCCCTCCCCTCCACTCTTA

TCAAATCCTTTCAGCGGTCGGAATGTCAGCGGGTCGAT

CANINIZED DUPI light chain (L3) amino acid sequence
SEQ ID NO: 38
DIVMTQTPLSLSVSPGEPASISCRSSQSLLYSIGYNYLDWYLQKPGQSPQLLIYLGSNRASGVPDRFSGSGSGTDF

TLRISRVEADDAGFYYCMQALQTPYTFGQGTKLEIKRNDAQPAVYLFQPSPDQLHTGSASVVCLLNSFYPKDI

NVKWKVDGVIQDTGIQESVTEQDSKDSTYSLSSTLTMSSTEYLSHELYSCEITHKSLPSTLIKSFQRSECQRVD

Example 4

Blocking Activity of Caninized Antibodies Against Canine IL-4 Receptor Alpha Testing for blocking activity of caninized antibodies against canine IL-4 receptor alpha was performed with a cell line, CHO-DG44 stable cell line expressing canine IL-4 receptor alpha.

Construction of CHO Cell Line Expressing Canine IL-4 Receptor Alpha Chain and its Use in Ligand Blockade Assays:

A nucleic acid encoding a full length canine IL-4 receptor alpha chain having the nucleotide sequence of SEQ ID NO: 1 was synthesized and sub-cloned into a mammalian expression vectors. The resulting plasmid was transfected into CHO DG44 cells. At 48 hours post-transfection, the cells were diluted into 96-well plates to generate single cell clones. About 130 clones were obtained after a 4-week incubation. All of the clones were screened for expression of the cloned Interleukin-4 receptor alpha [cIL-4Rα] by FACS using an anti-cIL-4Rα monoclonal antibody (6B2). Three clones were selected for stability evaluation, which was monitored for 20 passages by FACS.

A ligand blockade assay was set up to assess the ability of the monoclonal antibodies specific for the canine IL-4 receptor alpha to block the binding of canine IL-4 to canine IL-4R alpha expressed on the surface of CHO cells:

Reagent and Equipments:
  Cell growth medium: CD OptiCHO medium+8 mM L-Glutamine+0.018% F-68
  FACS Buffer: BD Pharmingen Stain Buffer (BD cat #: 554657)
  R-phycoerythin conjugated Streptavidin (Life Technologies: SB66)
  Canine IL-4 (R&D system, cat #754-CL/CF)
  Lightning-Link Biotin Conjugation Kit Type A (Novus: 704-0010) used to biotinylate canine IL-4 as per manufacturer's recommendation
  Flow cytometer: BD FACSCanto II
  Cell line: The CHO-DG44 stable cell line expressing canine IL-4 receptor alpha.

Procedure:
1. The CHO-DG44-canIL-4Rα cells were grown to 2-4× $10^6$ cells/mL with more than 96% viability.
2. The cells were spun down, the supernatant discarded, and the cells were suspended in FACS buffer to $2\times10^7$ cells/mL.
3. The cells were distributed into a U-shape 96-well plate, 50 μl each well.
4. The anti-canine IL-4Rα (Dupi H2-L2) mAbs in FACS buffer was diluted three-fold on a 96-well plate from top down to bottom well, starting at 50 μg/mL.
5. 50 μl of each diluted Ab was transferred into the cell plate and then incubated on ice for 30 min.
6. The cells were washed twice with FACS buffer.
7. The cells were resuspended into 100 μl of biotinylated canine IL-4 at 0.32 μg/mL in FACS buffer and incubated on ice for 30 min.
8. The cells were washed twice with 250 μL FACS buffer.
9. The cells were resuspended into 100 μl of R-phycoerythin conjugated Streptavidin (1:100 dilution) in FACS buffer and incubated on ice for 30 min.
10. The cells were washed twice with 250 μL FACS buffer.
11. The cells were brought up to 300 μl in FACS buffer.
12. 10,000 cells were read for each sample by BD FACSCanto II.
13. The resulting readout were analyzed by FlowJo to get the Mean Fluorescent Intensity (MFI).

Figure 2:
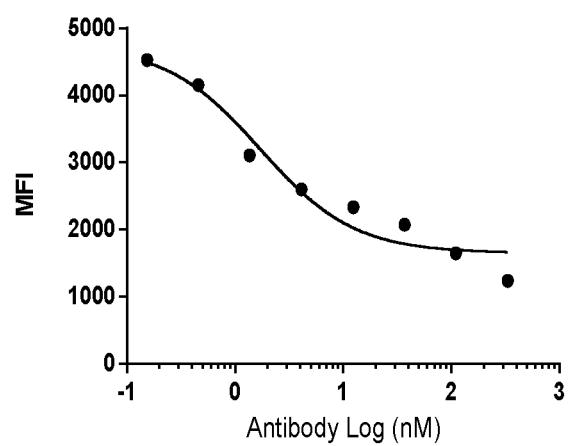
FIG. 2 provides the results of a FACS assay for testing the blocking activity of caninized Dupi monoclonal antibody against the interaction of canine IL-4 with the canine IL-4 receptor alpha expressed on CHO cells.

FIG. 2 depicts the results for a FACS assay for testing the blocking activity of caninized Dupi mAb against the interaction of canine IL-4 with IL-4 receptor alpha expressed on CHO cells. These results demonstrate a dose-dependent blocking activity of caninized Dupi H2-L2 antibody on the interaction of canine IL-4 with the IL-4 receptor alpha expressed on CHO cells.

Example 5

Testing the Neutralizing Activity of Caninized Dupi Antibodies Against Canine IL-4Rα

Construction of BaF3 cell line expressing IL-4 receptor alpha BaF3 is a murine progenitor B cell line and its cell proliferation is dependent on murine IL-3. It has been demonstrated that BaF3 cells expressing human IL-4 receptor alpha chain can proliferate with stimulation of IL-4. This protocol is for creating a BaF3 stable cell line expressing canine IL-4 receptor alpha chain, with the resulting cell line proliferating upon stimulation by canine IL-4.

The BaF3 Growth Medium is RPMI 1640 with 10% FBS, 4 mM L-glutamine, 50 μM 2-Mercaptoethanol, 0.5 ng/mL mouse IL-3, and Pen/Strep.

Selection Medium: The Growth Medium with IL-3 Substituted by Canine IL-4.

1. A vial of BaF3 cells are thawed at 37° C. and the thawed cells are transferred into 30 mL of growth medium and incubated at 37° C., with 8% $CO_2$ in a shaker at 125 rpm.
2. The cells are passaged 3 times before transfection. For transfection the resulting cells must be ≥96% viable.
3. $1\times10^7$ viable cells are spun down and resuspended with 700 μL RPMI 1640.
4. The cells are transfer into a 4 mm gap cuvette on ice, and then 40 μg pTT5-cIL-4Rα plasmid DNA is added in 1004 RPMI 1640 into the cuvette and gently mixed.
5. The cells are transfected by electroporation at 200 v, 1000 μF, and then transferred into selection medium that contains 25 ng/mL cIL-4.
6. The pooled cells are then incubated at 37° C. with 8% $CO_2$ in a shaker at 125 rpm to recover the cells that can grow under cIL-4.
7. The pool cells are passaged continually in the medium with cIL-4 to stabilize the cell line for 7 passages.
8. Single cell clones are selected by limiting dilution analysis.

Figure 3:
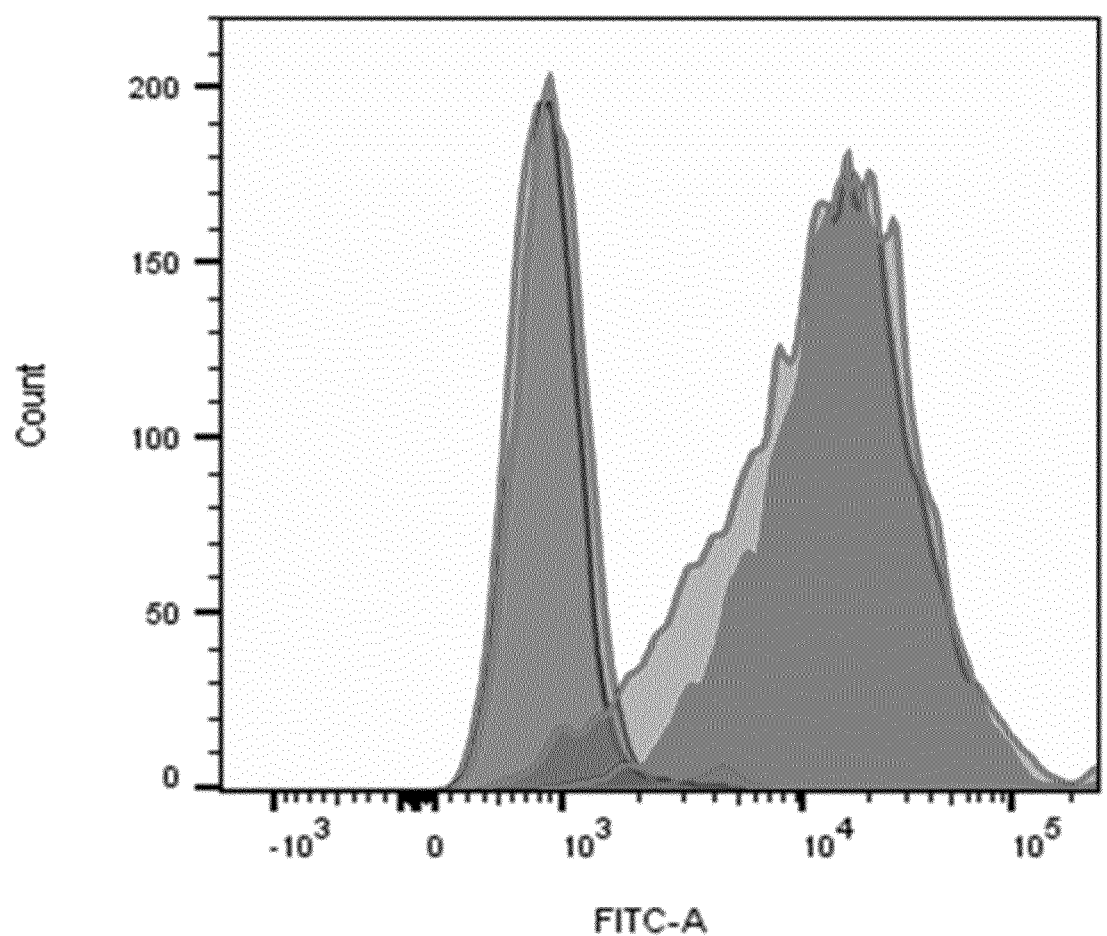
FIG. 3 provides the results of a FACS assay for testing binding activity of caninized Dupi H2-L2 monoclonal antibody against the canine IL-4 receptor alpha expressed on BaF3 cells.

FIG. 3 depicts the results of the FACS assay testing the binding activity of caninized Dupi H2-L2 antibody to the canine IL-4 receptor alpha expressed on the BaF3 cells prepared as indicated above.

FACS Assay for Determining the Expression of Canine IL-4 Receptor Alpha by BaF3 Cells and Confirming the Binding Activity of the Caninized Dupi Antibody to that Receptor on the Cells.

1. Grow the above cells in the selection medium with canine IL-4 in 37° C., 8% $CO_2$ shaker with 125 rpm.
2. Passage the cells 2-3 times in the growth medium with mouse IL-3 before the setup of the assay, and make sure the cell viability is ≥95%.
3. Spin down the cells, discard the supernatant, wash the cells twice with 250 μL of FACS buffer and resuspend the cells into FACS buffer to $1\times10^7$ viable cells/mL.
4. Add selected antibodies to three individual 100 μL aliquots of the cells to 5 μg/mL, respectively: to separate cell aliquots add the caninized DupiH2L2; a caninized murine antibody raised against canine IL-4Rα, as a positive control; and a caninized murine antibody raised against an unrelated antigen as a negative control. In addition, a fourth cell aliquot has no antibody added.
5. Incubate the cells on ice for 30 min. with gentle shaking, and then wash the cells twice with 250 μL of FACS buffer.
6. Resuspend the cells into 100 μl of rabbit anti-dog IgG FITC and incubate on ice for 30 min with gentle shaking.
7. Wash the cells with 2×250 μL of FACS buffer.
8. Bring up the cells to 300 μl of FACS buffer.
9. Read 20,000 cells for each sample by BD FACSCanto II.

The resulting FACS assay depicted in FIG. 3 shows four independent peaks, the first two peaks corresponding to: (a) the BaF3 cells alone, and (b) the BaF3 cells that had been incubated with a caninized murine antibody that had been raised against a non-related antigen (a negative control). In both cases the peaks are relatively narrow and the amount of dye (FITC-A) is equal to the background value (centered at just below $10^3$). This is consistent with the absence of bound canine antibody. The other two peaks in FIG. 3 correspond to: (c) the BaF3 cells that had been incubated with a caninized murine antibody raised against canine IL-4Rα (a positive control), and (d) the BaF3 cells that had been incubated with Dupi H2L2. In both of these cases the peaks are broad and the amount of dye (FITC-A) is substantially greater than the background value (centered at just above $10^4$). This increase in FITC-A is due to the BaF3 cells expressing canine IL-4Rα and the caninized Dupi H2L2 and the positive control binding to the expressed IL-4Rα, respectively. In short, FIG. 3 demonstrates that the BaF3 cells transfected by pTT5-cIL-4Rα plasmid can express canine IL-4 receptor alpha, and that the caninized Dupi antibody can bind to that expressed canine IL-4Rα.

MTT Cell Proliferation Assay for Testing Neutralizing Activity of Caninized Dupi Antibodies Against Canine IL-4 Receptor Alpha:

Cell line: The BaF3 stable cell line expressing canine IL-4 receptor alpha chain as described above.

1. The cells are grown in the selection medium with canine IL-4 at 37° C. with 8% $CO_2$ in a shaker at 125 rpm.
2. The cells are passaged 2-3 times in the growth medium with mouse IL-3 before the setup of the assay. For the assay the resulting cells must be ≥96% viable.
3. The cells are spun down at 1250 rpm for 3 minutes, and resuspended in starvation medium (basic medium without serum, IL-3 and IL-4) to $4 \times 10^6$ viable cells/mL.
4. The cells are dispensed into a 96 well plate, 50 µL/well (about $0.2 \times 10^6$ viable cells/well to avoid an edge effect, leaving the first and last column and row for 200 µL medium per well.)
5. Antibody with a starting concentration of 1 mg/mL is two-fold diluted in the starvation medium in the 96 well plate.
6. 50 µL of the diluted antibody is transferred into each well of the cell plate, and gently mixed.
7. For 1-2 hours the plate is incubated at 37° C. with 8% $CO_2$ in a shaker at 125 rpm.
8. 110 ng/mL of canine IL-4 solution in the starvation medium is prepared and then dispensed into the cell plates with 10 µL per well.
9. For 48 hours the plate is incubated at 37° C. with 8% $CO_2$ in a shaker at 125 rpm.
10. 15 µL of the MTT-based dye solution is added into each well, and for 2-4 hours the plate is incubated at 37° C. with 8% $CO_2$ in a shaker at 125 rpm 2-4 hrs to develop color.
11. 100 µL of stop solution is added into each well and the plate is incubated at room temperature for 1 hour (the plate can be stored at 4° C. overnight).
12. The plate is read at 570 nm with a 650 nm reference.

Figure 4:
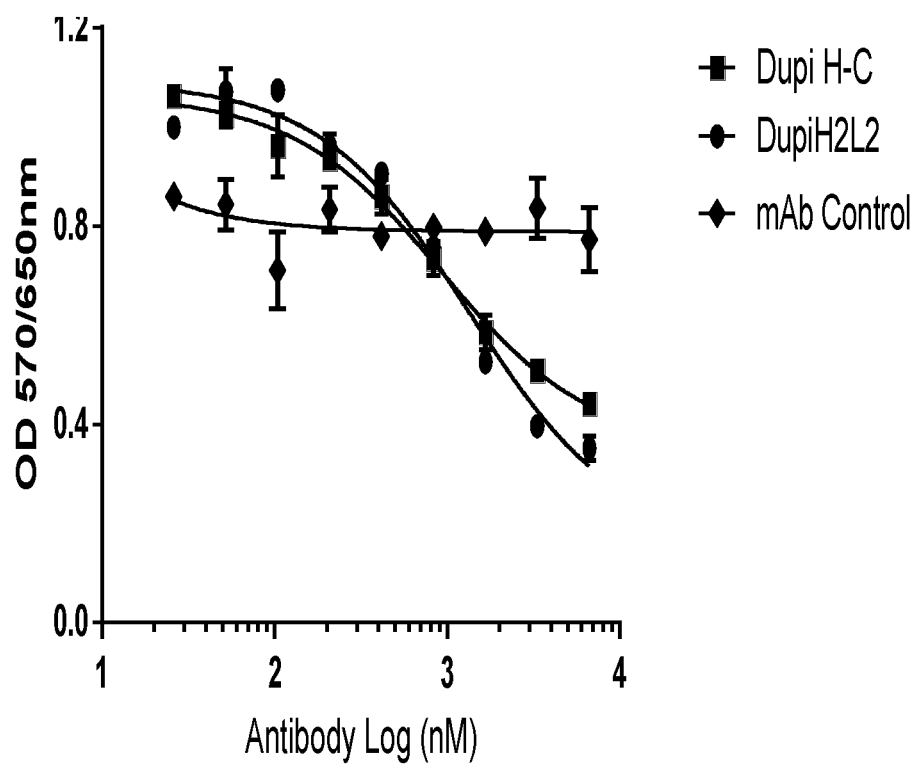
FIG. 4 provides the results of a MTT [3-(4,5-dimethyl-thiazol-2-yl)-2,5-diphenyltetrazolium bromide] cell-based assay for testing cell viability as a function of the neutralizing activity of chimeric human-canine monoclonal antibody (Dupi H-C) and caninized monoclonal antibody (Dupi H2-L2) versus a control non-neutralizing antibody on BaF3 cell proliferation.

FIG. 4 depicts the MTT cell-based assay for testing the neutralizing activity of the chimeric human-canine monoclonal antibody (Dupi H-C) and caninized monoclonal antibody (Dupi H2-L2) versus a control non-neutralizing antibody on BaF3 cell proliferation. A dose-dependent neutralizing activity of both the Dupi H-C and the Dupi H2-L2 resulted in an observed decrease in BaF3 cell proliferation, whereas the control non-neutralizing antibody did not have this effect on cell proliferation.

Example 6

Mapping of Canine IL-4Rα Epitopes

Introduction

The interaction of antibodies with their cognate protein antigens is mediated through the binding of specific amino acids (paratopes) of the antibodies with specific amino acids (epitopes) of their target antigens. An epitope is an antigenic determinant that causes a specific reaction by an immunoglobulin. It consists of a group of amino acids on the surface of the antigen.

A protein of interest may contain several epitopes that are recognized by different antibodies. The epitopes recognized by antibodies are classified as linear or conformational epitopes. Linear epitopes are formed by a stretch of continuous sequence of amino acids in a protein, while conformational epitopes are composed of amino acids that are discontinuous (e.g., far apart) in the primary amino acid sequence, but are brought together upon three-dimensional protein folding.

Epitope mapping refers to the process of identifying the amino acid sequences (i.e., epitopes) that are recognized by antibodies on their target antigens. Identification of epitopes recognized by monoclonal antibodies (mAbs) on target antigens has important applications. For example, it can aid in the development of new therapeutics, diagnostics, and vaccines. Epitope mapping can also aid in the selection of optimized therapeutic mAbs (e.g., to treat atopic dermatitis) and help elucidate their mechanisms of action.

Figure 5:
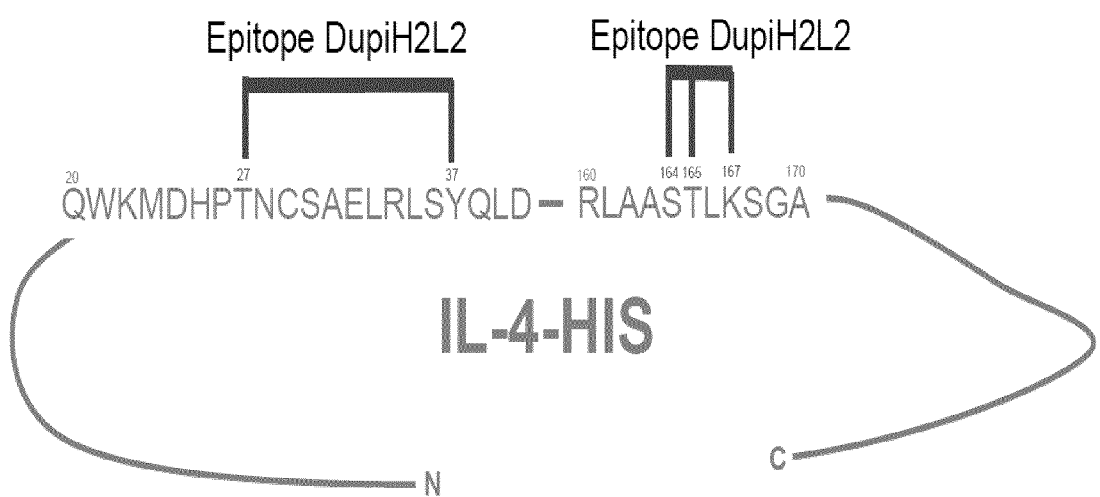
FIG. 5 depicts the peptide epitopes and specific amino acid residue contacts for the interaction between canine IL-4 receptor alpha chain and the caninized Dupi H2-L2 monoclonal antibody. Region 1 of the epitope was identified as being within the amino acid sequence of SEQ ID NO: 39, whereas Region 2 of the epitope was identified as being within the amino acid sequence of SEQ ID NO: 40.

Mapping of IL-4 Receptor Alpha Epitopes Using Mass Spectroscopy:

Epitope mapping of a discontinuous epitope is technically challenging and requires specialized techniques such as x-ray co-crystallography of a monoclonal antibody together with its target protein, Hydrogen-Deuterium (H/D) exchange, and/or Mass Spectroscopy coupled with enzymatic digestion. In order to identify the epitope(s) recognized by the anti-canine IL-4Rα mAb cDupi H2-L2, a method based on chemical cross-linking, High-Mass MALDI mass spectrometry and nLC-Orbitrap mass spectrometry was used (CovalX® Instrument Incorporated). As depicted in FIG. 5 the application of this technology to epitope mapping of canine IL-4Rα led to localization of the epitope(s) to two regions in the extracellular domain (ECD) of canine IL-4Rα chain represented by SEQ ID NO: 39 (amino acid sequence: QWKMDHPTNCSAELRLSYQLD; Region 1) and SEQ ID No: 40 (amino acid sequence: RLAASTLKSGA; Region 2) with the contact amino acid residues in bold. The results also show that these two regions include the amino acids of IL-4Rα chain which are in contact with the cDupi H2-L2 antibody, and in particular, the threonine residue at amino acid position 27, the tyrosine residue at amino acid position 37, the serine residue at amino acid position 164, the threonine residue at amino acid position 165, and the lysine residue at amino acid position 167 of the amino acid sequence of SEQ ID NO: 4. The results indicate that the epitope is within the amino acid sequence of TNCSAELRLSY (SEQ ID NO: 41; Sub-Region 1) and/or the amino acid sequence of STLK (SEQ ID NO: 42; Sub-Region 2).

Moreover, though certainly not predictable, the amino acid residues in the canine IL-4Rα chain sequence that were determined to be in contact with the caninized antibody (Dupi H2-L2) were found to be identical to the corresponding amino acid residues of the human IL-4Rα sequence. Although the epitope of the human IL-4Rα chain has not been disclosed, on the basis of the present findings that the contact amino acid residues in the canine IL-4Rα chain are identical to those in the corresponding human IL-4Rα sequence, along with the cross-reactivity reported herein, suggest that the epitope presently identified for this antibody in the canine IL-4Rα sequence is also likely to be the epitope in the human IL-4Rα sequence.

| SEQUENCE LISTING TABLE | | | |
|---|---|---|---|
| ID | N.A. | A.A. | Description |
| 1 | ✓ | | Canine IL-4Rα Full Length |
| 2 | | ✓ | Canine IL-4Rα Full Length |
| 3 | ✓ | | Canine IL-4Rα mature |
| 4 | | ✓ | Canine IL-4Rα mature |
| 5 | ✓ | | Canine IL-4Rα ECD (w/o sig. seq.) |
| 6 | | ✓ | Canine IL-4Rα ECD (w/o sig. seq.) |
| 7 | ✓ | | Canine IL-4Rα extcell. dom. + His tag |
| 8 | | ✓ | Canine IL-4Rα extcell. dom. + His tag |
| 9 | ✓ | | Canine IL-4Rα extcell. dom. + hIgG1 Fc |
| 10 | | ✓ | Canine IL-4Rα extcell. dom. + hIgG1 Fc |
| 11 | ✓ | | cIgGB wt |
| 12 | ✓ | | cIgGB(+)A-hinge |
| 13 | ✓ | | cIgGB(+)D-hinge |
| 14 | ✓ | | cIgGB(−)ADCC |
| 15 | ✓ | | Chimeric Dupi Heavy anti-IL-4Rα Ab |
| 16 | | ✓ | Chimeric Dupi Heavy anti-IL-4Rα Ab |
| 17 | ✓ | | Chimeric Dupi Kappa anti-IL-4Rα Ab |
| 18 | | ✓ | Chimeric Dupi Kappa anti-IL-4Rα Ab |
| 19 | ✓ | | Chimeric M37 Heavy anti-IL-4Rα Ab |
| 20 | | ✓ | Chimeric M37 Heavy anti-IL-4Rα Ab |
| 21 | ✓ | | Chimeric M37 Kappa anti-IL-4Rα Ab |
| 22 | | ✓ | Chimeric M37 Kappa anti-IL-4Rα Ab |
| 23 | ✓ | | Chimeric 12B5 Heavy anti-IL-4Rα Ab |
| 24 | | ✓ | Chimeric 12B5 Heavy anti-IL-4Rα Ab |
| 25 | ✓ | | Chimeric 12B5 Kappa anti-IL-4Rα Ab |
| 26 | | ✓ | Chimeric 12B5 Kappa anti-IL-4Rα Ab |
| 27 | ✓ | | Caninized Dupi H1 Heavy anti-IL-4Rα Ab |
| 28 | | ✓ | Caninized Dupi H1 Heavy anti-IL-4Rα Ab |
| 29 | ✓ | | Caninized Dupi H2 Heavy anti-IL-4Rα Ab |
| 30 | | ✓ | Caninized Dupi H2 Heavy anti-IL-4Rα Ab |
| 31 | ✓ | | Caninized Dupi H3 Heavy anti-IL-4Rα Ab |
| 32 | | ✓ | Caninized Dupi H3 Heavy anti-IL-4Rα Ab |
| 33 | ✓ | | Caninized Dupi L1 Kappa anti-IL-4Rα Ab |
| 34 | | ✓ | Caninized Dupi L1 Kappa anti-IL-4Rα Ab |
| 35 | ✓ | | Caninized Dupi L2 Kappa anti-IL-4Rα Ab |
| 36 | | ✓ | Caninized Dupi L2 Kappa anti-IL-4Rα Ab |
| 37 | ✓ | | Caninized Dupi L3 Kappa anti-IL-4Rα Ab |
| 38 | | ✓ | Caninized Dupi L3 Kappa anti-IL-4Rα Ab |
| 39 | | ✓ | Region 1 Epitope |
| 40 | | ✓ | Region 2 Epitope |
| 41 | | ✓ | Sub-Region 1 Epitope |
| 42 | | ✓ | Sub-Region 2 Epitope |
| 61 | | ✓ | IgGA Hinge Region |
| 62 | | ✓ | IgGB Hinge Region |
| 63 | | ✓ | IgGC Hinge Region |
| 64 | | ✓ | IgGD Modified Hinge Region |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

We claim:

1. An isolated caninized antibody or antigen binding fragment thereof that specifically binds interleukin-4 receptor alpha (IL-4Rα) comprising a canine IgG heavy chain and a canine kappa light chain; wherein the canine kappa light chain comprises three light chain complementary determining regions (CDRs): CDR light 1 (CDRL1), CDR light 2 (CDRL2), and CDR light 3 (CDRL3); and the canine IgG heavy chain comprises three heavy chain CDRs: CDR heavy 1 (CDRH1), CDR heavy 2 (CDRH2) and CDR heavy 3 (CDRH3):
   (a) wherein CDRL1 comprises the amino acid sequence of SEQ ID NO: 43;
   (b) wherein CDRL2 comprises the amino acid sequence comprising SEQ ID NO: 44;
   (c) wherein CDRL3 comprises the amino acid sequence of SEQ ID NO: 45;
   (d) wherein CDRH1 comprises the amino acid sequence of SEQ ID NO: 46;
   (e) wherein CDRH2 comprises the amino acid sequence of SEQ ID NO: 47; and
   (f) wherein CDRH3 comprises the amino acid sequence of SEQ ID NO: 48.

2. The isolated caninized antibody of claim 1, wherein the IgG heavy chain comprises an amino acid sequence selected from the group consisting of SEQ ID NO: 28, SEQ ID NO: 30, and SEQ ID NO: 32.

3. The isolated caninized antibody of claim 2, wherein the kappa light chain comprises an amino acid sequence selected from the group consisting of SEQ ID NO: 34, SEQ ID NO: 36, and SEQ ID NO: 38.

4. The isolated caninized antibody of claim 1, or antigen binding fragment thereof, wherein said caninized antibody or antigen binding fragment thereof binds to canine IL-4Rα at one or more amino acid residue from the amino acid sequence selected from the group consisting of SEQ ID NO: 39, SEQ ID NO: 40, SEQ ID NO: 41, SEQ ID NO: 42 and any combination thereof.

5. The isolated caninized antibody of claim 4, wherein when bound to canine IL-4Rα said antibody binds to one or more amino acid residues of SEQ ID NO: 4 selected from the group consisting of $T_{27}$, $Y_{37}$, $S_{164}$, $T_{165}$, $K_{167}$, and any combination thereof.

6. The isolated caninized antibody of claim 1, or antigen binding fragment thereof which binds canine IL-4Rα and blocks the binding of canine IL-4Rα with canine Interleukin-4 (IL-4).

7. A pharmaceutical composition comprising the antibody of claim 1, and a pharmaceutically acceptable carrier or diluent.

8. The isolated caninized antibody of claim 5, wherein when bound to canine IL-4Rα said antibody binds to the tyrosine residue at amino acid position 37, ($Y_{37}$).

9. The isolated caninized antibody of claim 4, or antigen binding fragment thereof, wherein said caninized antibody or antigen binding fragment thereof binds to canine IL-4Rα at one or more amino acid residue from the amino acid sequence SEQ ID NO: 39.

10. The isolated caninized antibody of claim 3, wherein the IgG heavy chain comprises the amino acid sequence of SEQ ID NO: 30 and the kappa light chain comprises the amino acid sequence of SEQ ID NO: 36.

* * * * *

SEQUENCE LISTING

```
<160> NUMBER OF SEQ ID NOS: 94

<210> SEQ ID NO 1
<211> LENGTH: 2469
<212> TYPE: DNA
<213> ORGANISM: Canis familiaris

<400> SEQUENCE: 1
atgggcagac tgtgcagcgg cctgaccttc cccgtgagct gcctggtgct ggtgtgggtg    60
```

-continued

```
gccagcagcg gcagcgtgaa ggtgctgcac gagcccagct gcttcagcga ctacatcagc      120
accagcgtgt gccagtggaa gatggaccac cccaccaact gcagcgccga gctgagactg      180
agctaccagc tggacttcat gggcagcgag aaccacacct gcgtgcccga aacagagag       240 gacagcgtgt gcgtgtgcag catgcccatc gacgacgccg tggaggccga cgtgtaccag      300
ctggacctgt gggccggcca gcagctgctg tggagcggca gcttccagcc cagcaagcac      360
gtgaagccca aaccccggg caacctgacc gtgcaccca acatcagcca cctggctg          420 ctgatgtgga ccaacccta ccccaccgag aaccacctgc acagcgagct gacctacatg       480
gtgaacgtga gcaacgacaa cgaccccgag gacttcaagg tgtacaacgt gacctacatg      540
ggccccaccc tgagactggc cgccagcacc ctgaagagcg gcgccagcta cagcgccaga      600
gtgagagcct gggcccagac ctacaacagc acctggagcg actggagccc cagcaccacc      660
tggctgaact actacgagcc ctgggagcag cacctgcccc tgggcgtgag catcagctgc      720
ctggtgatcc tggccatctg cctgagctgc tacttcagca tcatcaagat caagaagggc      780
tggtgggacc agatccccaa ccccgccac agccccctgg tggccatcgt gatccaggac      840
agccaggtga gcctgtgggg caagagaagc agaggccagg agcccgccaa gtgccccac      900 tggaagacct gcctgaccaa gctgctgccc tgcctgctgg agcacggcct gggcagagag      960
gaggagagcc ccaagaccgc caagaacggc cccctgcagg gccccggcaa gcccgcctgg     1020
tgccccgtgg aggtgagcaa gaccatcctg tggcccgaga gcatcagcgt ggtgcagtgc     1080
gtggagctga gcgaggcccc cgtggacaac gaggaggagg aggagtgga ggaggacaag      1140 agaagcctgt gccccagcct ggagggcagc ggcggcagct ccaggaggg cagagagggc     1200 atcgtggcca gactgaccga gagcctgttc ctggacctgc tgggcggcga aacggcggc      1260 ttctgccccc agggcctgga ggagagctgc ctgcccccc ccagcggcag cgtgggcgcc      1320
cagatgccct gggcccagtt ccccagagcc ggccccagag ccgccccga gggccccgag       1380 cagcccagaa gacccgagag cgccctgcag gccagcccca ccccagagcgc cggcagcagc    1440 gccttccccg agcccccccc cgtggtgacc gacaacccg cctacagaag cttcggcagc      1500
ttcctgggcc agagcagcga ccccggcgac ggcgacagcg accccgagct ggccgacaga     1560
cccggcgagg ccgaccccgg catccccagc gccccccagc ccccgagcc ccccgccgcc      1620 ctgcagcccg agcccgagag ctgggagcag atcctgagac agagcgtgct gcagcacaga     1680
gccgcccccg ccccggccc cggccccggc agcggctaca gagagttcac ctgcgccgtg     1740
aagcagggca gcgccccga cgccggcggc cccggcttcg gccccagcgg cgaggccggc      1800
tacaaggcct tctgcagcct gctgcccggc ggcgccacct gccccggcac cagcggcggc     1860
gaggccggca gcggcgaggg cggctacaag cccttccaga gcctgacccc cggctgcccc     1920 ggcgcccca ccccgtgcc cgtgccctg ttcaccttcg gcctggacac cgagcccccc        1980
ggcagccccc aggacagcct gggcgccggc agcagcccg agcacctggg cgtgagcccc      2040
gccggcaagg aggaggacag cagaaagacc ctgctggccc ccgagcaggc caccgacccc     2100
ctgagagacg acctggccag cagcatcgtg tacagcgccc tgacctgcca cctgtgcggc     2160
cacctgaagc agtggcacga ccaggaggag gaggcaagg cccacatcgt gcccagcccc     2220
tgctgcggct gctgctgcgg cgacagaagc agcctgctgc tgagcccct gagagcccc      2280 aacgtgctgc ccggcggcgt gctgctggag gccagcctga gcccgccag cctggtgccc     2340 agcggcgtga gcaaggaggg caagagcagc cccttcagcc agcccgccag cagcagcgcc     2400
cagagcagca gccagacccc aagaagctg gccgtgctga gcaccgagcc cacctgcatg      2460
``` agcgccagc 2469

<210> SEQ ID NO 2
<211> LENGTH: 823
<212> TYPE: PRT
<213> ORGANISM: Canis familiaris

<400> SEQUENCE: 2

```
Met Gly Arg Leu Cys Ser Gly Leu Thr Phe Pro Val Ser Cys Leu Val
1               5                   10                  15

Leu Val Trp Val Ala Ser Ser Gly Ser Val Lys Val Leu His Glu Pro
            20                  25                  30

Ser Cys Phe Ser Asp Tyr Ile Ser Thr Ser Val Cys Gln Trp Lys Met
        35                  40                  45

Asp His Pro Thr Asn Cys Ser Ala Glu Leu Arg Leu Ser Tyr Gln Leu
    50                  55                  60

Asp Phe Met Gly Ser Glu Asn His Thr Cys Val Pro Glu Asn Arg Glu
65                  70                  75                  80

Asp Ser Val Cys Val Cys Ser Met Pro Ile Asp Asp Ala Val Glu Ala
                85                  90                  95

Asp Val Tyr Gln Leu Asp Leu Trp Ala Gly Gln Gln Leu Leu Trp Ser
            100                 105                 110

Gly Ser Phe Gln Pro Ser Lys His Val Lys Pro Arg Thr Pro Gly Asn
        115                 120                 125

Leu Thr Val His Pro Asn Ile Ser His Thr Trp Leu Leu Met Trp Thr
    130                 135                 140

Asn Pro Tyr Pro Thr Glu Asn His Leu His Ser Glu Leu Thr Tyr Met
145                 150                 155                 160

Val Asn Val Ser Asn Asp Asn Asp Pro Glu Asp Phe Lys Val Tyr Asn
                165                 170                 175

Val Thr Tyr Met Gly Pro Thr Leu Arg Leu Ala Ala Ser Thr Leu Lys
            180                 185                 190

Ser Gly Ala Ser Tyr Ser Ala Arg Val Arg Trp Ala Gln Thr Tyr
        195                 200                 205

Asn Ser Thr Trp Ser Asp Trp Ser Pro Ser Thr Thr Trp Leu Asn Tyr
    210                 215                 220

Tyr Glu Pro Trp Glu Gln His Leu Pro Leu Gly Val Ser Ile Ser Cys
225                 230                 235                 240

Leu Val Ile Leu Ala Ile Cys Leu Ser Cys Tyr Phe Ser Ile Ile Lys
                245                 250                 255

Ile Lys Lys Gly Trp Trp Asp Gln Ile Pro Asn Pro Ala His Ser Pro
            260                 265                 270

Leu Val Ala Ile Val Ile Gln Asp Ser Gln Val Ser Leu Trp Gly Lys
        275                 280                 285

Arg Ser Arg Gly Gln Glu Pro Ala Lys Cys Pro His Trp Lys Thr Cys
    290                 295                 300

Leu Thr Lys Leu Leu Pro Cys Leu Leu Glu His Gly Leu Gly Arg Glu
305                 310                 315                 320

Glu Glu Ser Pro Lys Thr Ala Lys Asn Gly Pro Leu Gln Gly Pro Gly
                325                 330                 335

Lys Pro Ala Trp Cys Pro Val Glu Val Ser Lys Thr Ile Leu Trp Pro
            340                 345                 350

Glu Ser Ile Ser Val Val Gln Cys Val Glu Leu Ser Glu Ala Pro Val
        355                 360                 365
```

```
Asp Asn Glu Glu Glu Glu Val Glu Glu Asp Lys Arg Ser Leu Cys
    370                 375                 380

Pro Ser Leu Glu Gly Ser Gly Gly Ser Phe Gln Gly Arg Glu Gly
385                 390                 395                 400

Ile Val Ala Arg Leu Thr Glu Ser Leu Phe Leu Asp Leu Leu Gly
                405                 410                 415

Glu Asn Gly Gly Phe Cys Pro Gln Gly Leu Glu Glu Ser Cys Leu Pro
                420                 425                 430

Pro Pro Ser Gly Ser Val Gly Ala Gln Met Pro Trp Ala Gln Phe Pro
            435                 440                 445

Arg Ala Gly Pro Arg Ala Ala Pro Glu Gly Pro Glu Gln Pro Arg Arg
    450                 455                 460

Pro Glu Ser Ala Leu Gln Ala Ser Pro Thr Gln Ser Ala Gly Ser Ser
465                 470                 475                 480

Ala Phe Pro Glu Pro Pro Val Val Thr Asp Asn Pro Ala Tyr Arg
                485                 490                 495

Ser Phe Gly Ser Phe Leu Gly Gln Ser Ser Asp Pro Gly Asp Gly Asp
                500                 505                 510

Ser Asp Pro Glu Leu Ala Asp Arg Pro Gly Glu Ala Asp Pro Gly Ile
    515                 520                 525

Pro Ser Ala Pro Gln Pro Pro Glu Pro Ala Ala Leu Gln Pro Glu
530                 535                 540

Pro Glu Ser Trp Glu Gln Ile Leu Arg Gln Ser Val Leu Gln His Arg
545                 550                 555                 560

Ala Ala Pro Ala Pro Gly Pro Gly Pro Gly Ser Gly Tyr Arg Glu Phe
                565                 570                 575

Thr Cys Ala Val Lys Gln Gly Ser Ala Pro Asp Ala Gly Gly Pro Gly
            580                 585                 590

Phe Gly Pro Ser Gly Glu Ala Gly Tyr Lys Ala Phe Cys Ser Leu Leu
                595                 600                 605

Pro Gly Gly Ala Thr Cys Pro Gly Thr Ser Gly Gly Glu Ala Gly Ser
    610                 615                 620

Gly Glu Gly Gly Tyr Lys Pro Phe Gln Ser Leu Thr Pro Gly Cys Pro
625                 630                 635                 640

Gly Ala Pro Thr Pro Val Pro Val Pro Leu Phe Thr Phe Gly Leu Asp
                645                 650                 655

Thr Glu Pro Pro Gly Ser Pro Gln Asp Ser Leu Gly Ala Gly Ser Ser
                660                 665                 670

Pro Glu His Leu Gly Val Glu Pro Ala Gly Lys Glu Asp Ser Arg
    675                 680                 685

Lys Thr Leu Leu Ala Pro Glu Gln Ala Thr Asp Pro Leu Arg Asp Asp
    690                 695                 700

Leu Ala Ser Ser Ile Val Tyr Ser Ala Leu Thr Cys His Leu Cys Gly
705                 710                 715                 720

His Leu Lys Gln Trp His Asp Gln Glu Glu Arg Gly Lys Ala His Ile
                725                 730                 735

Val Pro Ser Pro Cys Cys Gly Cys Cys Cys Gly Asp Arg Ser Ser Leu
            740                 745                 750

Leu Leu Ser Pro Leu Arg Ala Pro Asn Val Leu Pro Gly Gly Val Leu
        755                 760                 765

Leu Glu Ala Ser Leu Ser Pro Ala Ser Leu Val Pro Ser Gly Val Ser
    770                 775                 780
```

Lys Glu Gly Lys Ser Ser Pro Phe Ser Gln Pro Ala Ser Ser Ala
785                 790                 795                 800

Gln Ser Ser Ser Gln Thr Pro Lys Lys Leu Ala Val Leu Ser Thr Glu
            805                 810                 815

Pro Thr Cys Met Ser Ala Ser
            820

<210> SEQ ID NO 3
<211> LENGTH: 2394
<212> TYPE: DNA
<213> ORGANISM: Canis familiaris

<400> SEQUENCE: 3

| | | | | |
|---|---|---|---|---|
| gtgaaggtgc | tgcacgagcc | cagctgcttc | agcgactaca | tcagcaccag cgtgtgccag | 60 |
| tggaagatgg | accaccccac | caactgcagc | gccgagctga | gactgagcta ccagctggac | 120 |
| ttcatgggca | gcgagaacca | cacctgcgtg | cccgagaaca | gagaggacag cgtgtgcgtg | 180 |
| tgcagcatgc | ccatcgacga | cgccgtggag | gccgacgtgt | accagctgga cctgtgggcc | 240 |
| ggccagcagc | tgctgtggag | cggcagcttc | agcccagca | agcacgtgaa gcccagaacc | 300 |
| cccggcaacc | tgaccgtgca | ccccaacatc | agccacacct | ggctgctgat gtggaccaac | 360 |
| ccctacccca | ccgagaacca | cctgcacagc | gagctgacct | acatggtgaa cgtgagcaac | 420 |
| gacaacgacc | ccgaggactt | caaggtgtac | aacgtgacct | acatgggccc caccctgaga | 480 |
| ctggccgcca | gcaccctgaa | gagcggcgcc | agctacagcg | ccagagtgag agcctgggcc | 540 |
| cagacctaca | acagcacctg | gagcgactgg | agccccagca | ccacctggct gaactactac | 600 |
| gagccctggg | agcagcacct | gccctgggc | gtgagcatca | gctgcctggt gatcctggcc | 660 |
| atctgcctga | gctgctactt | cagcatcatc | aagatcaaga | agggctggtg ggaccagatc | 720 |
| cccaaccccg | cccacagccc | cctggtggcc | atcgtgatcc | aggacagcca ggtgagcctg | 780 |
| tggggcaaga | gaagcagagg | ccaggagccc | gccaagtgcc | cccactggaa gacctgcctg | 840 |
| accaagctgc | tgccctgcct | gctggagcac | ggcctgggca | gagaggagga gagccccaag | 900 |
| accgccaaga | acggccccct | gcagggcccc | ggcaagcccg | cctggtgccc cgtggaggtg | 960 |
| agcaagacca | tcctgtggcc | cgagagcatc | agcgtggtgc | agtgcgtgga gctgagcgag | 1020 |
| gcccccgtgg | acaacgagga | ggaggaggag | gtggaggagg | acaagagaag cctgtgcccc | 1080 |
| agcctggagg | cagcggcgg | cagcttccag | gagggcagag | agggcatcgt ggccagactg | 1140 |
| accgagagcc | tgttcctgga | cctgctgggc | ggcgagaacg | gcggcttctg ccccagggc | 1200 |
| ctggaggaga | gctgcctgcc | cccccccagc | ggcagcgtgg | gcgcccagat gcctgggcc | 1260 |
| cagttccccca | gagccggccc | cagagccgcc | ccgagggcc | ccgagcagcc cagaagaccc | 1320 |
| gagagcgccc | tgcaggccag | ccccacccag | agcgccggca | gcgcgcctt ccccgagccc | 1380 |
| ccccccgtgg | tgaccgacaa | ccccgcctac | agaagcttcg | gcagcttcct gggccagagc | 1440 |
| agcgaccccg | cgacggcga | cagcgacccc | gagctggccg | acagacccgg cgaggccgac | 1500 |
| cccggcatcc | ccagcgcccc | ccagccccc | gagccccccg | ccgccctgca gcccgagccc | 1560 |
| gagagctggg | agcagatcct | gagacagagc | gtgctgcagc | acagagccgc ccccgccccc | 1620 |
| ggccccggcc | ccgcagcgg | ctacagagag | ttcacctgcg | ccgtgaagca gggcagcgcc | 1680 |
| cccgacgccg | gcgcccggg | cttcggcccc | agcggcgagg | ccggctacaa ggccttctgc | 1740 |
| agcctgctgc | ccgcggcgc | cacctgcccc | ggcaccagcg | gcggcgaggc cggcagcggc | 1800 |
| gagggcggct | acaagccctt | ccagagcctg | accccggct | gccccggcgc cccacccccc | 1860 |

```
gtgcccgtgc ccctgttcac cttcggcctg gacaccgagc ccccggcag ccccccaggac   1920 agcctgggcg ccggcagcag ccccgagcac ctgggcgtgg agcccgccgg caaggaggag   1980
gacagcagaa agaccctgct ggccccccgag caggccaccg accccctgag agacgacctg   2040
gccagcagca tcgtgtacag cgccctgacc tgccacctgt gcggccacct gaagcagtgg   2100
cacgaccagg aggagagagg caaggcccac atcgtgccca gccctgctg cggctgctgc   2160 tgcggcgaca gaagcagcct gctgctgagc cccctgagag cccccaacgt gctgcccggc   2220
ggcgtgctgc tggaggccag cctgagcccc gccagcctgg tgcccagcgg cgtgagcaag   2280
gagggcaaga gcagccctt cagccagccc gccagcagca gcgcccagag cagcagccag   2340 accccccaaga agctggccgt gctgagcacc gagcccacct gcatgagcgc cagc        2394
```

<210> SEQ ID NO 4
<211> LENGTH: 798
<212> TYPE: PRT
<213> ORGANISM: Canis familiaris

<400> SEQUENCE: 4

```
Val Lys Val Leu His Glu Pro Ser Cys Phe Ser Asp Tyr Ile Ser Thr
1               5                   10                  15

Ser Val Cys Gln Trp Lys Met Asp His Pro Thr Asn Cys Ser Ala Glu
                20                  25                  30

Leu Arg Leu Ser Tyr Gln Leu Asp Phe Met Gly Ser Glu Asn His Thr
            35                  40                  45

Cys Val Pro Glu Asn Arg Glu Asp Ser Val Cys Val Cys Ser Met Pro
        50                  55                  60

Ile Asp Asp Ala Val Glu Ala Asp Val Tyr Gln Leu Asp Leu Trp Ala
65                  70                  75                  80

Gly Gln Gln Leu Leu Trp Ser Gly Ser Phe Gln Pro Ser Lys His Val
                85                  90                  95

Lys Pro Arg Thr Pro Gly Asn Leu Thr Val His Pro Asn Ile Ser His
                100                 105                 110

Thr Trp Leu Leu Met Trp Thr Asn Pro Tyr Pro Thr Glu Asn His Leu
            115                 120                 125

His Ser Glu Leu Thr Tyr Met Val Asn Val Ser Asn Asp Asn Asp Pro
        130                 135                 140

Glu Asp Phe Lys Val Tyr Asn Val Thr Tyr Met Gly Pro Thr Leu Arg
145                 150                 155                 160

Leu Ala Ala Ser Thr Leu Lys Ser Gly Ala Ser Tyr Ser Ala Arg Val
                165                 170                 175

Arg Ala Trp Ala Gln Thr Tyr Asn Ser Thr Trp Ser Asp Trp Ser Pro
                180                 185                 190

Ser Thr Thr Trp Leu Asn Tyr Tyr Glu Pro Trp Glu Gln His Leu Pro
            195                 200                 205

Leu Gly Val Ser Ile Ser Cys Leu Val Ile Leu Ala Ile Cys Leu Ser
        210                 215                 220

Cys Tyr Phe Ser Ile Ile Lys Ile Lys Lys Gly Trp Trp Asp Gln Ile
225                 230                 235                 240

Pro Asn Pro Ala His Ser Pro Leu Val Ala Ile Val Ile Gln Asp Ser
                245                 250                 255

Gln Val Ser Leu Trp Gly Lys Arg Ser Arg Gly Gln Glu Pro Ala Lys
                260                 265                 270

Cys Pro His Trp Lys Thr Cys Leu Thr Lys Leu Leu Pro Cys Leu Leu
            275                 280                 285
```

```
Glu His Gly Leu Gly Arg Glu Glu Ser Pro Lys Thr Ala Lys Asn
    290                 295                 300
Gly Pro Leu Gln Gly Pro Gly Lys Pro Ala Trp Cys Pro Val Glu Val
305                 310                 315                 320
Ser Lys Thr Ile Leu Trp Pro Glu Ser Ile Ser Val Val Gln Cys Val
                325                 330                 335
Glu Leu Ser Glu Ala Pro Val Asp Asn Glu Glu Glu Glu Val Glu
            340                 345                 350
Glu Asp Lys Arg Ser Leu Cys Pro Ser Leu Glu Gly Ser Gly Gly Ser
        355                 360                 365
Phe Gln Glu Gly Arg Glu Gly Ile Val Ala Arg Leu Thr Glu Ser Leu
    370                 375                 380
Phe Leu Asp Leu Leu Gly Gly Glu Asn Gly Gly Phe Cys Pro Gln Gly
385                 390                 395                 400
Leu Glu Glu Ser Cys Leu Pro Pro Ser Gly Ser Val Gly Ala Gln
                405                 410                 415
Met Pro Trp Ala Gln Phe Pro Arg Ala Gly Pro Arg Ala Ala Pro Glu
            420                 425                 430
Gly Pro Glu Gln Pro Arg Arg Pro Glu Ser Ala Leu Gln Ala Ser Pro
        435                 440                 445
Thr Gln Ser Ala Gly Ser Ser Ala Phe Pro Glu Pro Pro Val Val
    450                 455                 460
Thr Asp Asn Pro Ala Tyr Arg Ser Phe Gly Ser Phe Leu Gly Gln Ser
465                 470                 475                 480
Ser Asp Pro Gly Asp Gly Asp Ser Asp Pro Glu Leu Ala Asp Arg Pro
                485                 490                 495
Gly Glu Ala Asp Pro Gly Ile Pro Ser Ala Pro Gln Pro Pro Glu Pro
            500                 505                 510
Pro Ala Ala Leu Gln Pro Glu Pro Glu Ser Trp Glu Gln Ile Leu Arg
        515                 520                 525
Gln Ser Val Leu Gln His Arg Ala Ala Pro Ala Pro Gly Pro Gly Pro
    530                 535                 540
Gly Ser Gly Tyr Arg Glu Phe Thr Cys Ala Val Lys Gln Gly Ser Ala
545                 550                 555                 560
Pro Asp Ala Gly Gly Pro Gly Phe Gly Pro Ser Gly Glu Ala Gly Tyr
                565                 570                 575
Lys Ala Phe Cys Ser Leu Leu Pro Gly Gly Ala Thr Cys Pro Gly Thr
            580                 585                 590
Ser Gly Gly Glu Ala Gly Ser Gly Glu Gly Gly Tyr Lys Pro Phe Gln
        595                 600                 605
Ser Leu Thr Pro Gly Cys Pro Gly Ala Pro Thr Pro Val Pro Val Pro
    610                 615                 620
Leu Phe Thr Phe Gly Leu Asp Thr Glu Pro Pro Gly Ser Pro Gln Asp
625                 630                 635                 640
Ser Leu Gly Ala Gly Ser Ser Pro Glu His Leu Gly Val Glu Pro Ala
                645                 650                 655
Gly Lys Glu Glu Asp Ser Arg Lys Thr Leu Leu Ala Pro Glu Gln Ala
            660                 665                 670
Thr Asp Pro Leu Arg Asp Asp Leu Ala Ser Ser Ile Val Tyr Ser Ala
        675                 680                 685
Leu Thr Cys His Leu Cys Gly His Leu Lys Gln Trp His Asp Gln Glu
    690                 695                 700
```

```
Glu Arg Gly Lys Ala His Ile Val Pro Ser Pro Cys Cys Gly Cys Cys
705                 710                 715                 720

Cys Gly Asp Arg Ser Ser Leu Leu Leu Ser Pro Leu Arg Ala Pro Asn
            725                 730                 735

Val Leu Pro Gly Gly Val Leu Leu Glu Ala Ser Leu Ser Pro Ala Ser
        740                 745                 750

Leu Val Pro Ser Gly Val Ser Lys Glu Gly Lys Ser Ser Pro Phe Ser
    755                 760                 765

Gln Pro Ala Ser Ser Ser Ala Gln Ser Ser Ser Gln Thr Pro Lys Lys
770                 775                 780

Leu Ala Val Leu Ser Thr Glu Pro Thr Cys Met Ser Ala Ser
785                 790                 795

<210> SEQ ID NO 5
<211> LENGTH: 624
<212> TYPE: DNA
<213> ORGANISM: Canis familiaris

<400> SEQUENCE: 5
gtgaaggtgc tgcacgagcc cagctgcttc agcgactaca tcagcaccag cgtgtgccag      60
tggaagatgg accaccccac caactgcagc gccgagctga actgagcta ccagctggac     120 ttcatgggca gcgagaacca cacctgcgtg cccgagaaca gagaggacag cgtgtgcgtg     180
tgcagcatgc ccatcgacga cgccgtggag gccgacgtgt accagctgga cctgtgggcc     240
ggccagcagc tgctgtggag cggcagcttc cagcccagca agcacgtgaa gcccagaacc     300
cccggcaacc tgaccgtgca ccccaacatc agccacacct ggctgctgat gtggaccaac     360
ccctacccca ccgagaacca cctgcacagc gagctgacct acatggtgaa cgtgagcaac     420
gacaacgacc ccgaggactt caaggtgtac aacgtgacct acatgggccc caccctgaga     480
ctggccgcca gcaccctgaa gagcggcgcc agctacagcg ccagagtgag agcctgggcc     540
cagacctaca acagcacctg gagcgactgg agccccagca ccacctggct gaactactac     600
gagccctggg agcagcacct gccc                                            624

<210> SEQ ID NO 6
<211> LENGTH: 208
<212> TYPE: PRT
<213> ORGANISM: Canis familiaris

<400> SEQUENCE: 6

Val Lys Val Leu His Glu Pro Ser Cys Phe Ser Asp Tyr Ile Ser Thr
1               5                   10                  15

Ser Val Cys Gln Trp Lys Met Asp His Pro Thr Asn Cys Ser Ala Glu
            20                  25                  30

Leu Arg Leu Ser Tyr Gln Leu Asp Phe Met Gly Ser Glu Asn His Thr
        35                  40                  45

Cys Val Pro Glu Asn Arg Glu Asp Ser Val Cys Val Cys Ser Met Pro
    50                  55                  60

Ile Asp Asp Ala Val Glu Ala Asp Val Tyr Gln Leu Asp Leu Trp Ala
65                  70                  75                  80

Gly Gln Gln Leu Leu Trp Ser Gly Ser Phe Gln Pro Ser Lys His Val
            85                  90                  95

Lys Pro Arg Thr Pro Gly Asn Leu Thr Val His Pro Asn Ile Ser His
            100                 105                 110

Thr Trp Leu Leu Met Trp Thr Asn Pro Tyr Pro Thr Glu Asn His Leu
        115                 120                 125
```

His Ser Glu Leu Thr Tyr Met Val Asn Val Ser Asn Asp Pro
    130                 135                 140

Glu Asp Phe Lys Val Tyr Asn Val Thr Tyr Met Gly Pro Thr Leu Arg
145                 150                 155                 160

Leu Ala Ala Ser Thr Leu Lys Ser Gly Ala Ser Tyr Ser Ala Arg Val
                165                 170                 175

Arg Ala Trp Ala Gln Thr Tyr Asn Ser Thr Trp Ser Asp Trp Ser Pro
            180                 185                 190

Ser Thr Thr Trp Leu Asn Tyr Tyr Glu Pro Trp Glu Gln His Leu Pro
        195                 200                 205

<210> SEQ ID NO 7
<211> LENGTH: 648
<212> TYPE: DNA
<213> ORGANISM: Artificial Sequence
<220> FEATURE:
<223> OTHER INFORMATION: Canis familiaris plus His Tag

<400> SEQUENCE: 7
gtgaaggtgc tgcacgagcc cagctgcttc agcgactaca tcagcaccag cgtgtgccag    60
tggaagatgg accaccccac caactgcagc gccgagctga actgagcta ccagctggac   120
ttcatgggca gcgagaacca cacctgcgtg cccgagaaca gagaggacag cgtgtgcgtg   180
tgcagcatgc ccatcgacga cgccgtggag gccgacgtgt accagctgga cctgtgggcc   240
ggccagcagc tgctgtggag cggcagcttc agcccagca agcacgtgaa gccagaacc   300
cccggcaacc tgaccgtgca ccccaacatc agccacacct ggctgctgat gtggaccaac   360
ccctacccca ccgagaacca cctgcacagc gagctgacct acatggtgaa cgtgagcaac   420
gacaacgacc ccgaggactt caaggtgtac aacgtgacct acatgggccc caccctgaga   480
ctggccgcca gcaccctgaa gagcggcgcc agctacagcg ccagagtgag agcctgggcc   540
cagacctaca acagcacctg gagcgactgg agccccagca ccacctggct gaactactac   600
gagccctggg agcagcacct gccccaccac caccaccac accaccac            648

<210> SEQ ID NO 8
<211> LENGTH: 216
<212> TYPE: PRT
<213> ORGANISM: Artificial Sequence
<220> FEATURE:
<223> OTHER INFORMATION: Canis familiaris plus His Tag

<400> SEQUENCE: 8

Val Lys Val Leu His Glu Pro Ser Cys Phe Ser Asp Tyr Ile Ser Thr
1               5                   10                  15

Ser Val Cys Gln Trp Lys Met Asp His Pro Thr Asn Cys Ser Ala Glu
            20                  25                  30

Leu Arg Leu Ser Tyr Gln Leu Asp Phe Met Gly Ser Glu Asn His Thr
        35                  40                  45

Cys Val Pro Glu Asn Arg Glu Asp Ser Val Cys Val Cys Ser Met Pro
    50                  55                  60

Ile Asp Asp Ala Val Glu Ala Asp Val Tyr Gln Leu Asp Leu Trp Ala
65                  70                  75                  80

Gly Gln Gln Leu Leu Trp Ser Gly Ser Phe Gln Pro Ser Lys His Val
                85                  90                  95

Lys Pro Arg Thr Pro Gly Asn Leu Thr Val His Pro Asn Ile Ser His
            100                 105                 110

Thr Trp Leu Leu Met Trp Thr Asn Pro Tyr Pro Thr Glu Asn His Leu
            115                 120                 125

His Ser Glu Leu Thr Tyr Met Val Asn Val Ser Asn Asp Asn Asp Pro
        130                 135                 140

Glu Asp Phe Lys Val Tyr Asn Val Thr Tyr Met Gly Pro Thr Leu Arg
145                 150                 155                 160

Leu Ala Ala Ser Thr Leu Lys Ser Gly Ala Ser Tyr Ser Ala Arg Val
                165                 170                 175

Arg Ala Trp Ala Gln Thr Tyr Asn Ser Thr Trp Ser Asp Trp Ser Pro
            180                 185                 190

Ser Thr Thr Trp Leu Asn Tyr Tyr Glu Pro Trp Glu Gln His Leu Pro
        195                 200                 205

His His His His His His His His
    210                 215

<210> SEQ ID NO 9
<211> LENGTH: 1317
<212> TYPE: DNA
<213> ORGANISM: Artificial Sequence
<220> FEATURE:
<223> OTHER INFORMATION: Canis familiaris plus human

<400> SEQUENCE: 9
gtgaaggtgc tgcacgagcc cagctgcttc agcgactaca tcagcaccag cgtgtgccag      60
tggaagatgg accaccccac caactgcagc gccgagctga actgagcta ccagctggac     120 ttcatgggca gcagaaacca cacctgcgtg cccgagaaca gagaggacag cgtgtgcgtg     180
tgcagcatgc ccatcgacga cgccgtggag gccgacgtgt accagctgga cctgtgggcc     240
ggccagcagc tgctgtggag cggcagcttc agcccagca agcacgtgaa gcccagaacc     300
cccggcaacc tgaccgtgca ccccaacatc agccacacct ggctgctgat gtggaccaac     360
ccctacccca ccgagaacca cctgcacagc gagctgacct acatggtgaa cgtgagcaac     420
gacaacgacc ccgaggactt caaggtgtac aacgtgacct acatgggccc caccctgaga     480
ctggccgcca gcaccctgaa gagcggcgcc agctacagcg ccagagtgag agcctgggcc     540
cagacctaca acagcacctg gagcgactgg agccccagca ccacctggct gaactactac     600
gagccctggg agcagcacct ggagcccaag agctgcgaca gaccccacac ctgccccccc     660
tgccccgccc ccgagctgct gggcggcccc agcgtgttcc tgttcccccc caagcccaag     720 gacacccctga tgatcagcag aacccccgag gtgacctgcg tggtggtgga cgtgagccac     780
gaggaccccg aggtgaagtt caactggtac gtggacggcg tggaggtgca caacgccaag     840
accaagccca gagaggagca gtacaacagc acctacagag tggtgagcgt gctgaccgtg     900
ctgcaccagg actggctgaa cggcaaggag tacaagtgca aggtgagcaa caaggccctg     960
cccgccccca tcgagaagac catcagcaag gccaagggcc agccagaga gccccaggtg    1020 tacaccctgc cccccagcag agacgagctg accaagaacc aggtgagcct gacctgcctg    1080
gtgaagggct tctaccccag cgacatcgcc gtggagtggg agagcaacgg ccagcccgag    1140
aacaactaca agaccacccc ccccgtgctg gacagcgacg gcagcttctt cctgtacagc    1200
aagctgaccg tggacaagag cagatggcag caggcaactg tgttcagctg cagcgtgatg    1260
cacgaggccc tgcacaacca ctacacccag aagagcctga gcctgagccc cggcaag      1317

<210> SEQ ID NO 10
<211> LENGTH: 439
<212> TYPE: PRT

<213> ORGANISM: Artificial Sequence
<220> FEATURE:
<223> OTHER INFORMATION: Canis familiaris plus human

<400> SEQUENCE: 10

```
Val Lys Val Leu His Glu Pro Ser Cys Phe Ser Asp Tyr Ile Ser Thr
1               5                   10                  15

Ser Val Cys Gln Trp Lys Met Asp His Pro Thr Asn Cys Ser Ala Glu
            20                  25                  30

Leu Arg Leu Ser Tyr Gln Leu Asp Phe Met Gly Ser Glu Asn His Thr
        35                  40                  45

Cys Val Pro Glu Asn Arg Glu Asp Ser Val Cys Val Cys Ser Met Pro
50                  55                  60

Ile Asp Asp Ala Val Glu Ala Asp Val Tyr Gln Leu Asp Leu Trp Ala
65                  70                  75                  80

Gly Gln Gln Leu Leu Trp Ser Gly Ser Phe Gln Pro Ser Lys His Val
                85                  90                  95

Lys Pro Arg Thr Pro Gly Asn Leu Thr Val His Pro Asn Ile Ser His
            100                 105                 110

Thr Trp Leu Leu Met Trp Thr Asn Pro Tyr Pro Thr Glu Asn His Leu
        115                 120                 125

His Ser Glu Leu Thr Tyr Met Val Asn Val Ser Asn Asp Asn Asp Pro
130                 135                 140

Glu Asp Phe Lys Val Tyr Asn Val Thr Tyr Met Gly Pro Thr Leu Arg
145                 150                 155                 160

Leu Ala Ala Ser Thr Leu Lys Ser Gly Ala Ser Tyr Ser Ala Arg Val
                165                 170                 175

Arg Ala Trp Ala Gln Thr Tyr Asn Ser Thr Trp Ser Asp Trp Ser Pro
            180                 185                 190

Ser Thr Thr Trp Leu Asn Tyr Tyr Glu Pro Trp Glu Gln His Leu Glu
        195                 200                 205

Pro Lys Ser Cys Asp Lys Thr His Thr Cys Pro Pro Cys Pro Ala Pro
210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
        275                 280                 285

Asn Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Tyr Thr Leu Pro Pro Ser Arg Asp Glu Leu Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
```

```
385                 390                 395                 400
Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro Gly Lys
        435

<210> SEQ ID NO 11
<211> LENGTH: 336
<212> TYPE: PRT
<213> ORGANISM: Canis familiaris

<400> SEQUENCE: 11

Ser Ala Ser Thr Thr Ala Pro Ser Val Phe Pro Leu Ala Pro Ser Cys
1               5                   10                  15

Gly Ser Thr Ser Gly Ser Thr Val Ala Leu Ala Cys Leu Val Ser Gly
            20                  25                  30

Tyr Phe Pro Glu Pro Val Thr Val Ser Trp Asn Ser Gly Ser Leu Thr
        35                  40                  45

Ser Gly Val His Thr Phe Pro Ser Val Leu Gln Ser Ser Gly Leu Tyr
    50                  55                  60

Ser Leu Ser Ser Met Val Thr Val Pro Ser Ser Arg Trp Pro Ser Glu
65                  70                  75                  80

Thr Phe Thr Cys Asn Val Ala His Pro Ala Ser Lys Thr Lys Val Asp
                85                  90                  95

Lys Pro Val Pro Lys Arg Glu Asn Gly Arg Val Pro Arg Pro Pro Asp
            100                 105                 110

Cys Pro Lys Cys Pro Ala Pro Glu Met Leu Gly Gly Pro Ser Val Phe
        115                 120                 125

Ile Phe Pro Pro Lys Pro Lys Asp Thr Leu Leu Ile Ala Arg Thr Pro
    130                 135                 140

Glu Val Thr Cys Val Val Val Asp Leu Asp Pro Glu Asp Pro Glu Val
145                 150                 155                 160

Gln Ile Ser Trp Phe Val Asp Gly Lys Gln Met Gln Thr Ala Lys Thr
                165                 170                 175

Gln Pro Arg Glu Glu Gln Phe Asn Gly Thr Tyr Arg Val Val Ser Val
            180                 185                 190

Leu Pro Ile Gly His Gln Asp Trp Leu Lys Gly Lys Gln Phe Thr Cys
        195                 200                 205

Lys Val Asn Asn Lys Ala Leu Pro Ser Pro Ile Glu Arg Thr Ile Ser
    210                 215                 220

Lys Ala Arg Gly Gln Ala His Gln Pro Ser Val Tyr Val Leu Pro Pro
225                 230                 235                 240

Ser Arg Glu Glu Leu Ser Lys Asn Thr Val Ser Leu Thr Cys Leu Ile
                245                 250                 255

Lys Asp Phe Phe Pro Pro Asp Ile Asp Val Glu Trp Gln Ser Asn Gly
            260                 265                 270

Gln Gln Glu Pro Glu Ser Lys Tyr Arg Thr Thr Pro Pro Gln Leu Asp
        275                 280                 285

Glu Asp Gly Ser Tyr Phe Leu Tyr Ser Lys Leu Ser Val Asp Lys Ser
    290                 295                 300

Arg Trp Gln Arg Gly Asp Thr Phe Ile Cys Ala Val Met His Glu Ala
305                 310                 315                 320
```

Leu His Asn His Tyr Thr Gln Glu Ser Leu Ser His Ser Pro Gly Lys
                    325                 330                 335

<210> SEQ ID NO 12
<211> LENGTH: 331
<212> TYPE: PRT
<213> ORGANISM: Artificial Sequence
<220> FEATURE:
<223> OTHER INFORMATION: modified Canis familiaris

<400> SEQUENCE: 12

Ser Ala Ser Thr Thr Ala Pro Ser Val Phe Pro Leu Ala Pro Ser Cys
1               5                   10                  15

Gly Ser Thr Ser Gly Ser Thr Val Ala Leu Ala Cys Leu Val Ser Gly
                20                  25                  30

Tyr Phe Pro Glu Pro Val Thr Val Ser Trp Asn Ser Gly Ser Leu Thr
            35                  40                  45

Ser Gly Val His Thr Phe Pro Ser Val Leu Gln Ser Ser Gly Leu Tyr
        50                  55                  60

Ser Leu Ser Ser Met Val Thr Val Pro Ser Ser Arg Trp Pro Ser Glu
65                  70                  75                  80

Thr Phe Thr Cys Asn Val Ala His Pro Ala Ser Lys Thr Lys Val Asp
                85                  90                  95

Lys Pro Val Phe Asn Glu Cys Arg Cys Thr Asp Thr Pro Pro Cys Pro
            100                 105                 110

Ala Pro Glu Met Leu Gly Gly Pro Ser Val Phe Ile Phe Pro Pro Lys
        115                 120                 125

Pro Lys Ala Thr Leu Leu Ile Ala Arg Thr Pro Glu Val Thr Cys Val
130                 135                 140

Val Val Asp Leu Asp Pro Glu Asp Pro Glu Val Gln Ile Ser Trp Phe
145                 150                 155                 160

Val Asp Gly Lys Gln Met Gln Thr Ala Lys Thr Gln Pro Arg Glu Glu
                165                 170                 175

Gln Phe Ala Gly Thr Tyr Arg Val Val Ser Val Leu Pro Ile Gly His
            180                 185                 190

Gln Asp Trp Leu Lys Gly Lys Gln Phe Thr Cys Lys Val Asn Asn Lys
        195                 200                 205

Ala Leu Pro Ser Pro Ile Glu Arg Thr Ile Ser Lys Ala Arg Gly Gln
210                 215                 220

Ala His Gln Pro Ser Val Tyr Val Leu Pro Pro Ser Arg Glu Glu Leu
225                 230                 235                 240

Ser Lys Asn Thr Val Ser Leu Thr Cys Leu Ile Lys Asp Phe Phe Pro
                245                 250                 255

Pro Asp Ile Asp Val Glu Trp Gln Ser Asn Gly Gln Gln Glu Pro Glu
            260                 265                 270

Ser Lys Tyr Arg Thr Thr Pro Pro Gln Leu Asp Glu Asp Gly Ser Tyr
        275                 280                 285

Phe Leu Tyr Ser Lys Leu Ser Val Asp Lys Ser Arg Trp Gln Arg Gly
290                 295                 300

Asp Thr Phe Ile Cys Ala Val Met His Glu Ala Leu His Asn His Tyr
305                 310                 315                 320

Thr Gln Glu Ser Leu Ser His Ser Pro Gly Lys
                325                 330

<210> SEQ ID NO 13
<211> LENGTH: 331

```
<212> TYPE: PRT
<213> ORGANISM: Artificial Sequence
<220> FEATURE:
<223> OTHER INFORMATION: modified Canis familiaris

<400> SEQUENCE: 13

Ser Ala Ser Thr Thr Ala Pro Ser Val Phe Pro Leu Ala Pro Ser Cys
1               5                   10                  15

Gly Ser Thr Ser Gly Ser Thr Val Ala Leu Ala Cys Leu Val Ser Gly
                20                  25                  30

Tyr Phe Pro Glu Pro Val Thr Val Ser Trp Asn Ser Gly Ser Leu Thr
            35                  40                  45

Ser Gly Val His Thr Phe Pro Ser Val Leu Gln Ser Ser Gly Leu Tyr
50                  55                  60

Ser Leu Ser Ser Met Val Thr Val Pro Ser Ser Arg Trp Pro Ser Glu
65                  70                  75                  80

Thr Phe Thr Cys Asn Val Ala His Pro Ala Ser Lys Thr Lys Val Asp
                85                  90                  95

Lys Pro Val Pro Lys Glu Ser Thr Cys Lys Cys Ile Ser Pro Cys Pro
            100                 105                 110

Ala Pro Glu Met Leu Gly Gly Pro Ser Val Phe Ile Phe Pro Pro Lys
        115                 120                 125

Pro Lys Ala Thr Leu Leu Ile Ala Arg Thr Pro Glu Val Thr Cys Val
130                 135                 140

Val Val Asp Leu Asp Pro Glu Asp Pro Glu Val Gln Ile Ser Trp Phe
145                 150                 155                 160

Val Asp Gly Lys Gln Met Gln Thr Ala Lys Thr Gln Pro Arg Glu Glu
                165                 170                 175

Gln Phe Ala Gly Thr Tyr Arg Val Val Ser Val Leu Pro Ile Gly His
            180                 185                 190

Gln Asp Trp Leu Lys Gly Lys Gln Phe Thr Cys Lys Val Asn Asn Lys
        195                 200                 205

Ala Leu Pro Ser Pro Ile Glu Arg Thr Ile Ser Lys Ala Arg Gly Gln
210                 215                 220

Ala His Gln Pro Ser Val Tyr Val Leu Pro Pro Ser Arg Glu Glu Leu
225                 230                 235                 240

Ser Lys Asn Thr Val Ser Leu Thr Cys Leu Ile Lys Asp Phe Phe Pro
                245                 250                 255

Pro Asp Ile Asp Val Glu Trp Gln Ser Asn Gly Gln Gln Glu Pro Glu
            260                 265                 270

Ser Lys Tyr Arg Thr Thr Pro Pro Gln Leu Asp Glu Asp Gly Ser Tyr
        275                 280                 285

Phe Leu Tyr Ser Lys Leu Ser Val Asp Lys Ser Arg Trp Gln Arg Gly
290                 295                 300

Asp Thr Phe Ile Cys Ala Val Met His Glu Ala Leu His Asn His Tyr
305                 310                 315                 320

Thr Gln Glu Ser Leu Ser His Ser Pro Gly Lys
                325                 330

<210> SEQ ID NO 14
<211> LENGTH: 336
<212> TYPE: PRT
<213> ORGANISM: Artificial Sequence
<220> FEATURE:
<223> OTHER INFORMATION: modified Canis familiaris

<400> SEQUENCE: 14
```

```
Ser Ala Ser Thr Thr Ala Pro Ser Val Phe Pro Leu Ala Pro Ser Cys
1               5                   10                  15

Gly Ser Thr Ser Gly Ser Thr Val Ala Leu Ala Cys Leu Val Ser Gly
            20                  25                  30

Tyr Phe Pro Glu Pro Val Thr Val Ser Trp Asn Ser Gly Ser Leu Thr
        35                  40                  45

Ser Gly Val His Thr Phe Pro Ser Val Leu Gln Ser Ser Gly Leu Tyr
    50                  55                  60

Ser Leu Ser Ser Met Val Thr Val Pro Ser Ser Arg Trp Pro Ser Glu
65              70                  75                  80

Thr Phe Thr Cys Asn Val Ala His Pro Ala Ser Lys Thr Lys Val Asp
            85                  90                  95

Lys Pro Val Pro Lys Arg Glu Asn Gly Arg Val Pro Arg Pro Pro Asp
            100                 105                 110

Cys Pro Lys Cys Pro Ala Pro Glu Met Leu Gly Gly Pro Ser Val Phe
            115                 120                 125

Ile Phe Pro Pro Lys Pro Lys Ala Thr Leu Leu Ile Ala Arg Thr Pro
        130                 135                 140

Glu Val Thr Cys Val Val Val Asp Leu Asp Pro Glu Asp Pro Glu Val
145                 150                 155                 160

Gln Ile Ser Trp Phe Val Asp Gly Lys Gln Met Gln Thr Ala Lys Thr
                165                 170                 175

Gln Pro Arg Glu Glu Gln Phe Ala Gly Thr Tyr Arg Val Val Ser Val
            180                 185                 190

Leu Pro Ile Gly His Gln Asp Trp Leu Lys Gly Lys Gln Phe Thr Cys
        195                 200                 205

Lys Val Asn Asn Lys Ala Leu Pro Ser Pro Ile Glu Arg Thr Ile Ser
210                 215                 220

Lys Ala Arg Gly Gln Ala His Gln Pro Ser Val Tyr Val Leu Pro Pro
225                 230                 235                 240

Ser Arg Glu Glu Leu Ser Lys Asn Thr Val Ser Leu Thr Cys Leu Ile
            245                 250                 255

Lys Asp Phe Phe Pro Pro Asp Ile Asp Val Glu Trp Gln Ser Asn Gly
            260                 265                 270

Gln Gln Glu Pro Glu Ser Lys Tyr Arg Thr Thr Pro Pro Gln Leu Asp
        275                 280                 285

Glu Asp Gly Ser Tyr Phe Leu Tyr Ser Lys Leu Ser Val Asp Lys Ser
        290                 295                 300

Arg Trp Gln Arg Gly Asp Thr Phe Ile Cys Ala Val Met His Glu Ala
305                 310                 315                 320

Leu His Asn His Tyr Thr Gln Glu Ser Leu Ser His Ser Pro Gly Lys
                325                 330                 335

<210> SEQ ID NO 15
<211> LENGTH: 1380
<212> TYPE: DNA
<213> ORGANISM: Artificial Sequence
<220> FEATURE:
<223> OTHER INFORMATION: Canis familiaris plus human

<400> SEQUENCE: 15
gaggtgcagc tggtggagtc cggaggagga ctggagcagc ccggaggaag cctgagactg      60
agctgcgctg gcagcggctt caccttcagg gactacgcca tgacctgggt gagacaggcc     120
cctggcaagg gactggagtg ggtgagcagc atcagcggct ccggcggcaa cacctactac     180
```

-continued

```
gccgacagcg tgaagggcag gttcaccatc agcagggaca acagcaagaa cacccctgtac    240 ctgcagatga acagcctgag ggccgaggac accgccgtgt actactgcgc caaggaccgt    300
ttatctatca ccatcaggcc caggtactac ggactggacg tgtggggcca gggcaccaca    360
gtgaccgtga gcagcgcttc cacaaccgcg ccatcagtct tccgttggc cccatcatgc     420 gggtcgacga gcggatcgac tgtggccctg gcgtgcttgg tgtcgggata ctttcccgaa    480
cccgtcacgg tcagctggaa ctccggatcg cttacgagcg tgtgcatac gttccctcg      540 gtcttgcaat catcagggct ctactcgctg tcgagcatgg taacggtgcc ctcatcgagg    600
tggccctccg aaacgttcac atgtaacgta gcacatccag cctccaaaac caaggtggat    660
aaacccgtgc cgaaaagaga aatgggcgg gtgcctcgac ccctgattg ccccaagtgt      720 ccggctccgg aaatgctcgg tggacccctca gtgtttatct tccctccgaa gcccaaggac   780
actctgctga tcgcgcgcac tccagaagta acatgtgtag tggtggcact tgatcccgag    840
gaccccgaag tccagatctc ctggtttgta gatgggaaac agatgcagac cgcaaaaact    900
caacccagag aggagcagtt cgcaggaaca taccgagtgg tatccgtcct tccgattggc    960
caccaggact ggttgaaagg gaagcagttt acgtgtaaag tcaacaataa ggcgttgcct   1020
agccctattg agcggacgat ttcgaaagct aggggacagg cccaccagcc atcggtctat   1080
gtccttccgc cttcccgcga ggagctctcg aagaatacag tgagccttac atgcctcatt   1140
aaggatttct tcccgcctga tatcgacgta gagtggcaat caaacggtca acaggagccg   1200
gaatccaagt atagaaccac tccgccccag cttgacgagg acggatcata cttttttgtat  1260 tcaaaactgt cggtggataa gagccggtgg cagagaggtg acaccttcat ctgtgcggtg   1320
atgcacgaag cactccataa tcactacacc caagagagcc tctcgcattc ccccggaaag   1380
```

<210> SEQ ID NO 16
<211> LENGTH: 460
<212> TYPE: PRT
<213> ORGANISM: Artificial Sequence
<220> FEATURE:
<223> OTHER INFORMATION: Canis familiaris plus human

<400> SEQUENCE: 16

```
Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser Ser Ala Ser Thr
        115                 120                 125

Thr Ala Pro Ser Val Phe Pro Leu Ala Pro Ser Cys Gly Ser Thr Ser
    130                 135                 140

Gly Ser Thr Val Ala Leu Ala Cys Leu Val Ser Gly Tyr Phe Pro Glu
```

```
                145                 150                 155                 160
Pro Val Thr Val Ser Trp Asn Ser Gly Ser Leu Thr Ser Gly Val His
                    165                 170                 175
Thr Phe Pro Ser Val Leu Gln Ser Ser Gly Leu Tyr Ser Leu Ser Ser
                    180                 185                 190
Met Val Thr Val Pro Ser Ser Arg Trp Pro Ser Glu Thr Phe Thr Cys
                    195                 200                 205
Asn Val Ala His Pro Ala Ser Lys Thr Lys Val Asp Lys Pro Val Pro
                    210                 215                 220
Lys Arg Glu Asn Gly Arg Val Pro Arg Pro Asp Cys Pro Lys Cys
225                 230                 235                 240
Pro Ala Pro Glu Met Leu Gly Gly Pro Ser Val Phe Ile Phe Pro Pro
                    245                 250                 255
Lys Pro Lys Asp Thr Leu Leu Ile Ala Arg Thr Pro Glu Val Thr Cys
                    260                 265                 270
Val Val Val Ala Leu Asp Pro Glu Asp Pro Glu Val Gln Ile Ser Trp
                    275                 280                 285
Phe Val Asp Gly Lys Gln Met Gln Thr Ala Lys Thr Gln Pro Arg Glu
                    290                 295                 300
Glu Gln Phe Ala Gly Thr Tyr Arg Val Val Ser Val Leu Pro Ile Gly
305                 310                 315                 320
His Gln Asp Trp Leu Lys Gly Lys Gln Phe Thr Cys Lys Val Asn Asn
                    325                 330                 335
Lys Ala Leu Pro Ser Pro Ile Glu Arg Thr Ile Ser Lys Ala Arg Gly
                    340                 345                 350
Gln Ala His Gln Pro Ser Val Tyr Val Leu Pro Pro Ser Arg Glu Glu
                    355                 360                 365
Leu Ser Lys Asn Thr Val Ser Leu Thr Cys Leu Ile Lys Asp Phe Phe
                    370                 375                 380
Pro Pro Asp Ile Asp Val Glu Trp Gln Ser Asn Gly Gln Gln Glu Pro
385                 390                 395                 400
Glu Ser Lys Tyr Arg Thr Thr Pro Pro Gln Leu Asp Glu Asp Gly Ser
                    405                 410                 415
Tyr Phe Leu Tyr Ser Lys Leu Ser Val Asp Lys Ser Arg Trp Gln Arg
                    420                 425                 430
Gly Asp Thr Phe Ile Cys Ala Val Met His Glu Ala Leu His Asn His
                    435                 440                 445
Tyr Thr Gln Glu Ser Leu Ser His Ser Pro Gly Lys
                    450                 455                 460

<210> SEQ ID NO 17
<211> LENGTH: 669
<212> TYPE: DNA
<213> ORGANISM: Artificial Sequence
<220> FEATURE:
<223> OTHER INFORMATION: Canis familiaris plus human

<400> SEQUENCE: 17
gacatcgtga tgacccagag cccccctgagc ctgcctgtga cacctggcga gcctgccagc      60
atcagctgca ggtccagcca gagcctgctg tacagcatcg gctacaacta cctggactgg     120
tacctgcaga gagcggcca gagccccag ctgctgatct acctgggcag caatagagcc      180
agcggcgtgc ccgatagatt tagcggcagc ggcagcggca cagacttcac cctgaagatc     240
agcagggtgg aggccgagga cgtgggcttc tactactgca tgcaggccct gcagacccc      300
```

```
tacaccttcg gccagggcac caagctggaa atcaagagga acgacgctca gccagccgtg      360
tacctcttcc agccttcgcc ggaccagctt catacggggt cagcgtcggt ggtgtgcctg      420
ttgaactcgt tttaccccaa ggacattaac gtgaagtgga aggtagacgg ggtaattcaa      480
gacactggca ttcaagagtc cgtcacggaa caagactcaa aagactcaac gtattcactg      540
tcgtcaacct tgacgatgtc aagcaccgag tatcttagcc atgagctgta ttcgtgcgag      600
atcacccaca agtccctccc ctccactctt atcaaatcct ttcagcggtc ggaatgtcag      660
cgggtcgat                                                              669
```

<210> SEQ ID NO 18
<211> LENGTH: 223
<212> TYPE: PRT
<213> ORGANISM: Artificial Sequence
<220> FEATURE:
<223> OTHER INFORMATION: Canis familiaris plus human

<400> SEQUENCE: 18

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Asn Asp Ala Gln Pro Ala Val Tyr Leu Phe Gln Pro Ser Pro Asp
        115                 120                 125

Gln Leu His Thr Gly Ser Ala Ser Val Val Cys Leu Leu Asn Ser Phe
    130                 135                 140

Tyr Pro Lys Asp Ile Asn Val Lys Trp Lys Val Asp Gly Val Ile Gln
145                 150                 155                 160

Asp Thr Gly Ile Gln Glu Ser Val Thr Glu Gln Asp Ser Lys Asp Ser
                165                 170                 175

Thr Tyr Ser Leu Ser Ser Thr Leu Thr Met Ser Ser Thr Glu Tyr Leu
            180                 185                 190

Ser His Glu Leu Tyr Ser Cys Glu Ile Thr His Lys Ser Leu Pro Ser
        195                 200                 205

Thr Leu Ile Lys Ser Phe Gln Arg Ser Glu Cys Gln Arg Val Asp
    210                 215                 220
```

<210> SEQ ID NO 19
<211> LENGTH: 1353
<212> TYPE: DNA
<213> ORGANISM: Artificial Sequence
<220> FEATURE:
<223> OTHER INFORMATION: Canis familiaris plus human

<400> SEQUENCE: 19

```
caggtgcagc tggtgcagag cggcgccgaa gtgaagaagc tggcgccag cgtgaaggtg      60 agctgcaagg ccagcggcta cgccttcacc agctactaca tgcactgggc cagacaggcc     120
```

```
cctggacagg gactggagtg gatgggcatc atcaaccta ggggcggcag caccagctac      180
gcccagaagt tccagggcag ggtggccatg accaggaca ccagcaccag caccgtgtac      240
atggaactga gcagcctgag acccgaggac accgccgtgt actactgcgc aggggcaag     300 tactggatgt acgactgggg caagggcacc ctcgtgaccg tgagcagcgc ttccacaacc     360
gcgccatcag tctttccgtt ggccccatca tgcgggtcga cgagcggatc gactgtggcc     420
ctggcgtgct tggtgtcggg atactttccc gaacccgtca cggtcagctg aactccgga     480 tcgcttacga gcggtgtgca tacgttcccc tcggtcttgc aatcatcagg gctctactcg     540
ctgtcgagca tggtaacggt gccctcatcg aggtggccct ccgaaacgtt cacatgtaac     600
gtagcacatc cagcctccaa aaccaaggtg ataaacccg tgccgaaaag agagaatggg     660
cgggtgcctc gaccccctga ttgccccaag tgtccggctc cggaaatgct cggtggaccc     720
tcagtgttta tcttccctcc gaagcccaag acactctgc tgatcgcgcg cactccagaa     780
gtaacatgtg tagtggtggc acttgatccc gaggaccccg aagtccagat ctcctggttt     840
gtagatggga aacagatgca gaccgcaaaa actcaaccca gagaggagca gttcgcagga     900
acataccgag tggtatccgt ccttccgatt ggccaccagg actggttgaa agggaagcag     960
tttacgtgta aagtcaacaa taaggcgttg cctagccta ttgagcggac gatttcgaaa     1020
gctaggggac aggcccacca gccatcggtc tatgtccttc cgccttcccg cgaggagctc     1080
tcgaagaata cagtgagcct tacatgcctc attaaggatt cttcccgcc tgatatcgac     1140 gtagagtggc aatcaaacgg tcaacaggag ccggaatcca agtatagaac cactccgccc     1200
cagcttgacg aggacggatc atactttttg tattcaaaac tgtcggtgga taagagccgg     1260 tgcagagag gtgacacctt catctgtgcg gtgatgcacg aagcactcca taatcactac     1320
acccaagaga gcctctcgca ttcccccgga aag                                  1353
```

<210> SEQ ID NO 20
<211> LENGTH: 451
<212> TYPE: PRT
<213> ORGANISM: Artificial Sequence
<220> FEATURE:
<223> OTHER INFORMATION: Canis familiaris plus human

<400> SEQUENCE: 20

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Tyr
            20                  25                  30

Tyr Met His Trp Ala Arg Gln Ala Pro Gly Gln Gly Leu Glu Trp Met
        35                  40                  45

Gly Ile Ile Asn Pro Arg Gly Gly Ser Thr Ser Tyr Ala Gln Lys Phe
    50                  55                  60

Gln Gly Arg Val Ala Met Thr Arg Asp Thr Ser Thr Ser Thr Val Tyr
65                  70                  75                  80

Met Glu Leu Ser Ser Leu Arg Pro Glu Asp Thr Ala Val Tyr Tyr Cys
                85                  90                  95

Ala Arg Gly Lys Tyr Trp Met Tyr Asp Trp Lys Gly Thr Leu Val
            100                 105                 110

Thr Val Ser Ser Ala Ser Thr Thr Ala Pro Ser Val Phe Pro Leu Ala
        115                 120                 125

Pro Ser Cys Gly Ser Thr Ser Gly Ser Thr Val Ala Leu Ala Cys Leu
    130                 135                 140
```

Val Ser Gly Tyr Phe Pro Glu Pro Val Thr Val Ser Trp Asn Ser Gly
145                 150                 155                 160

Ser Leu Thr Ser Gly Val His Thr Phe Pro Ser Val Leu Gln Ser Ser
            165                 170                 175

Gly Leu Tyr Ser Leu Ser Ser Met Val Thr Val Pro Ser Ser Arg Trp
        180                 185                 190

Pro Ser Glu Thr Phe Thr Cys Asn Val Ala His Pro Ala Ser Lys Thr
    195                 200                 205

Lys Val Asp Lys Pro Val Pro Lys Arg Glu Asn Gly Arg Val Pro Arg
210                 215                 220

Pro Pro Asp Cys Pro Lys Cys Pro Ala Pro Glu Met Leu Gly Gly Pro
225                 230                 235                 240

Ser Val Phe Ile Phe Pro Pro Lys Pro Lys Asp Thr Leu Leu Ile Ala
                245                 250                 255

Arg Thr Pro Glu Val Thr Cys Val Val Val Ala Leu Asp Pro Glu Asp
            260                 265                 270

Pro Glu Val Gln Ile Ser Trp Phe Val Asp Gly Lys Gln Met Gln Thr
        275                 280                 285

Ala Lys Thr Gln Pro Arg Glu Glu Gln Phe Ala Gly Thr Tyr Arg Val
    290                 295                 300

Val Ser Val Leu Pro Ile Gly His Gln Asp Trp Leu Lys Gly Lys Gln
305                 310                 315                 320

Phe Thr Cys Lys Val Asn Asn Lys Ala Leu Pro Ser Pro Ile Glu Arg
                325                 330                 335

Thr Ile Ser Lys Ala Arg Gly Gln Ala His Gln Pro Ser Val Tyr Val
            340                 345                 350

Leu Pro Pro Ser Arg Glu Glu Leu Ser Lys Asn Thr Val Ser Leu Thr
        355                 360                 365

Cys Leu Ile Lys Asp Phe Phe Pro Pro Asp Ile Asp Val Glu Trp Gln
    370                 375                 380

Ser Asn Gly Gln Gln Glu Pro Glu Ser Lys Tyr Arg Thr Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Arg Gly Asp Thr Phe Ile Cys Ala Val Met
            420                 425                 430

His Glu Ala Leu His Asn His Tyr Thr Gln Glu Ser Leu Ser His Ser
        435                 440                 445

Pro Gly Lys
    450

<210> SEQ ID NO 21
<211> LENGTH: 666
<212> TYPE: DNA
<213> ORGANISM: Artificial Sequence
<220> FEATURE:
<223> OTHER INFORMATION: Canis familiaris plus human

<400> SEQUENCE: 21
cagagcgtgc tgacccagcc tcctagcgtg agcgccgctc ccggccagaa agtgaccatc      60
agctgcagcg gcggcggaag cagcatcggc aacagctacg tgtcctggta ccagcagctg     120
cccggaaccg cccctaagct gctgatctac gacaacaaca gaggccctc cggcgtgccc      180 gacagattta gcggcagcaa gagcggcacc agcgccacac tggccatcac aggcctgcag     240

-continued

```
accggcgatg aggccgacta ctactgcggc acctgggaca caagccctgt gtgggaatgg    300
cccttcggca ccggcaccaa gctgaccgtg ctgaggaacg acgctcagcc agccgtgtac    360
ctcttccagc cttcgccgga ccagcttcat acggggtcag cgtcggtggt gtgcctgttg    420
aactcgtttt accccaagga cattaacgtg aagtggaagg tagacggggt aattcaagac    480
actggcattc aagagtccgt cacggaacaa gactcaaaag actcaacgta ttcactgtcg    540
tcaaccttga cgatgtcaag caccgagtat cttagccatg agctgtattc gtgcgagatc    600
acccacaagt ccctcccctc cactcttatc aaatcctttc agcggtcgga atgtcagcgg    660
gtcgat                                                               666
```

<210> SEQ ID NO 22
<211> LENGTH: 222
<212> TYPE: PRT
<213> ORGANISM: Artificial Sequence
<220> FEATURE:
<223> OTHER INFORMATION: Canis familiaris plus human

<400> SEQUENCE: 22

```
Gln Ser Val Leu Thr Gln Pro Pro Ser Val Ser Ala Ala Pro Gly Gln
1               5                   10                  15

Lys Val Thr Ile Ser Cys Ser Gly Gly Ser Ser Ile Gly Asn Ser
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Thr Ser Pro
                85                  90                  95

Val Trp Glu Trp Pro Phe Gly Thr Gly Thr Lys Leu Thr Val Leu Arg
            100                 105                 110

Asn Asp Ala Gln Pro Ala Val Tyr Leu Phe Gln Pro Ser Pro Asp Gln
        115                 120                 125

Leu His Thr Gly Ser Ala Ser Val Val Cys Leu Leu Asn Ser Phe Tyr
    130                 135                 140

Pro Lys Asp Ile Asn Val Lys Trp Lys Val Asp Gly Val Ile Gln Asp
145                 150                 155                 160

Thr Gly Ile Gln Glu Ser Val Thr Glu Gln Asp Ser Lys Asp Ser Thr
                165                 170                 175

Tyr Ser Leu Ser Ser Thr Leu Thr Met Ser Ser Thr Glu Tyr Leu Ser
            180                 185                 190

His Glu Leu Tyr Ser Cys Glu Ile Thr His Lys Ser Leu Pro Ser Thr
        195                 200                 205

Leu Ile Lys Ser Phe Gln Arg Ser Glu Cys Gln Arg Val Asp
    210                 215                 220
```

<210> SEQ ID NO 23
<211> LENGTH: 1350
<212> TYPE: DNA
<213> ORGANISM: Artificial Sequence
<220> FEATURE:
<223> OTHER INFORMATION: Canis familiaris plus human

<400> SEQUENCE: 23

```
gaggtgcagc tggtgcagag cggaggcgga ctggtgcatc ccggaggaag cctgagactg    60
```

```
tcctgcgccg gcagcggctt caccttcagc aggaacgcca tgttctgggt gagacaggcc      120
cccggcaagg gactggaatg ggtgagcctg atcggaaccg gaggcgccac caactacgcc      180
gacagcgtga agggcaggtt caccatcagc agggacaacg ccaagaacag cctgtacctg      240
cagatgaaca gcctgagggc cgaggacatg gccgtgtact actgcgccag ggcaggtac       300 tacttcgact attggggcca gggcaccctc gtgaccgtgt ccagcgcttc cacaaccgcg      360
ccatcagtct ttccgttggc cccatcatgc gggtcgacga gcggatcgac tgtggccctg      420
gcgtgcttgg tgtcgggata ctttcccgaa cccgtcacgg tcagctggaa ctccggatcg      480
cttacgagcg gtgtgcatac gttccccctcg gtcttgcaat catcagggct ctactcgctg      540
tcgagcatgg taacggtgcc ctcatcgagg tggccctccg aaacgttcac atgtaacgta      600
gcacatccag cctccaaaac caaggtggat aaacccgtgc cgaaaagaga gaatgggcgg      660
gtgcctcgac ccctgattg ccccaagtgt ccggctccgg aaatgctcgg tggaccctca      720
gtgtttatct tccctccgaa gcccaaggac actctgctga tcgcgcgcac tccagaagta      780
acatgtgtag tggtggcact tgatcccgag gaccccgaag tccagatctc ctggtttgta      840
gatgggaaac agatgcagac cgcaaaaact caacccagag aggagcagtt cgcaggaaca      900
taccgagtgg tatccgtcct tccgattggc caccaggact ggttgaaagg aagcagtttt     960
acgtgtaaag tcaacaataa ggcgttgcct agcctattg agcggacgat ttcgaaagct      1020
aggggacagg cccaccagcc atcggtctat gtccttccgc ctcccgcga ggagctctcg      1080 aagaatacag tgagccttac atgcctcatt aaggatttct tcccgcctga tatcgacgta      1140
gagtggcaat caaacggtca acaggagccg gaatccaagt atagaaccac tccgccccag      1200
cttgacgagg acggatcata ctttttgtat tcaaaactgt cggtggataa gagccggtgg      1260
cagagaggtg acaccttcat ctgtgcggtg atgcacgaag cactccataa tcactacacc      1320
caagagagcc tctcgcattc ccccggaaag                                       1350
```

<210> SEQ ID NO 24
<211> LENGTH: 450
<212> TYPE: PRT
<213> ORGANISM: Artificial Sequence
<220> FEATURE:
<223> OTHER INFORMATION: Canis familiaris plus human

<400> SEQUENCE: 24

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Leu Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser Ala Ser Thr Thr Ala Pro Ser Val Phe Pro Leu Ala Pro
        115                 120                 125
```

```
Ser Cys Gly Ser Thr Ser Gly Ser Thr Val Ala Leu Ala Cys Leu Val
130                 135                 140

Ser Gly Tyr Phe Pro Glu Pro Val Thr Val Ser Trp Asn Ser Gly Ser
145                 150                 155                 160

Leu Thr Ser Gly Val His Thr Phe Pro Ser Val Leu Gln Ser Ser Gly
                165                 170                 175

Leu Tyr Ser Leu Ser Ser Met Val Thr Val Pro Ser Ser Arg Trp Pro
                180                 185                 190

Ser Glu Thr Phe Thr Cys Asn Val Ala His Pro Ala Ser Lys Thr Lys
                195                 200                 205

Val Asp Lys Pro Val Pro Lys Arg Glu Asn Gly Arg Val Pro Arg Pro
210                 215                 220

Pro Asp Cys Pro Lys Cys Pro Ala Pro Glu Met Leu Gly Gly Pro Ser
225                 230                 235                 240

Val Phe Ile Phe Pro Pro Lys Pro Lys Asp Thr Leu Leu Ile Ala Arg
                245                 250                 255

Thr Pro Glu Val Thr Cys Val Val Val Ala Leu Asp Pro Glu Asp Pro
                260                 265                 270

Glu Val Gln Ile Ser Trp Phe Val Asp Gly Lys Gln Met Gln Thr Ala
                275                 280                 285

Lys Thr Gln Pro Arg Glu Glu Gln Phe Ala Gly Thr Tyr Arg Val Val
290                 295                 300

Ser Val Leu Pro Ile Gly His Gln Asp Trp Leu Lys Gly Lys Gln Phe
305                 310                 315                 320

Thr Cys Lys Val Asn Asn Lys Ala Leu Pro Ser Pro Ile Glu Arg Thr
                325                 330                 335

Ile Ser Lys Ala Arg Gly Gln Ala His Gln Pro Ser Val Tyr Val Leu
                340                 345                 350

Pro Pro Ser Arg Glu Glu Leu Ser Lys Asn Thr Val Ser Leu Thr Cys
                355                 360                 365

Leu Ile Lys Asp Phe Phe Pro Pro Asp Ile Asp Val Glu Trp Gln Ser
                370                 375                 380

Asn Gly Gln Gln Glu Pro Glu Ser Lys Tyr Arg Thr Thr Pro Pro Gln
385                 390                 395                 400

Leu Asp Glu Asp Gly Ser Tyr Phe Leu Tyr Ser Lys Leu Ser Val Asp
                405                 410                 415

Lys Ser Arg Trp Gln Arg Gly Asp Thr Phe Ile Cys Ala Val Met His
                420                 425                 430

Glu Ala Leu His Asn His Tyr Thr Gln Glu Ser Leu Ser His Ser Pro
                435                 440                 445

Gly Lys
    450

<210> SEQ ID NO 25
<211> LENGTH: 660
<212> TYPE: DNA
<213> ORGANISM: Artificial Sequence
<220> FEATURE:
<223> OTHER INFORMATION: Canis familiaris plus human

<400> SEQUENCE: 25
gagatcgtgc tgacccagag ccctggcaca ctgagcctga gccccggaga gagggctacc      60
ctgagctgca gggccagcca gagcgtgagc agcagctacc tggcctggta ccagcagaaa     120
cccggccagg cccccagact gctgatcttt ggcgccagca gcagagccac cggcatcccc     180
```

```
gatagattta gcggcagcgg cagcggcacc gactttaccc tgaccatcag caggctggag    240
cccgaggact tcgccgtgta ctactgccag cagtacggca gcagccctcc ttggaccttc    300
ggccagggca ccaaggtgga gatcaagagg aacgacgctc agccagccgt gtacctcttc    360
cagccttcgc cggaccagct tcatacgggg tcagcgtcgg tggtgtgcct gttgaactcg    420
ttttacccca aggacattaa cgtgaagtgg aaggtagacg gggtaattca agacactggc    480
attcaagagt ccgtcacgga acaagactca aaagactcaa cgtattcact gtcgtcaacc    540
ttgacgatgt caagcaccga gtatcttagc catgagctgt attcgtgcga gatcacccac    600
aagtccctcc cctccactct tatcaaatcc tttcagcggt cggaatgtca gcgggtcgat    660
```

<210> SEQ ID NO 26
<211> LENGTH: 220
<212> TYPE: PRT
<213> ORGANISM: Artificial Sequence
<220> FEATURE:
<223> OTHER INFORMATION: Canis familiaris plus human

<400> SEQUENCE: 26

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Thr Phe Gly Gln Gly Thr Lys Val Glu Ile Lys Arg Asn Asp
            100                 105                 110

Ala Gln Pro Ala Val Tyr Leu Phe Gln Pro Ser Pro Asp Gln Leu His
        115                 120                 125

Thr Gly Ser Ala Ser Val Val Cys Leu Leu Asn Ser Phe Tyr Pro Lys
    130                 135                 140

Asp Ile Asn Val Lys Trp Lys Val Asp Gly Val Ile Gln Asp Thr Gly
145                 150                 155                 160

Ile Gln Glu Ser Val Thr Glu Gln Asp Ser Lys Asp Ser Thr Tyr Ser
                165                 170                 175

Leu Ser Ser Thr Leu Thr Met Ser Ser Thr Glu Tyr Leu Ser His Glu
            180                 185                 190

Leu Tyr Ser Cys Glu Ile Thr His Lys Ser Leu Pro Ser Thr Leu Ile
        195                 200                 205

Lys Ser Phe Gln Arg Ser Glu Cys Gln Arg Val Asp
    210                 215                 220
```

<210> SEQ ID NO 27
<211> LENGTH: 1380
<212> TYPE: DNA
<213> ORGANISM: Artificial Sequence
<220> FEATURE:
<223> OTHER INFORMATION: Canis familiaris plus human

<400> SEQUENCE: 27

```
gaggtgcagc tggtggagag cggcggagac ctggtgaagc ctggaggcag cctgagactg    60
```

```
agctgcgtgg ccagcggctt caccttcagg gactacgcca tgacctgggt gaggcaggct    120
cctggaaagg gcctgcagtg ggtggcctcc attagcggca gcggcggcaa cacatactac    180
gccgacagcg tgaagggcag gttcaccatc agcagggaca acgccaagaa caccctgtac    240
ctgcagatga acagcctgag ggccgaggac accgccgtgt actactgcac cagggacagg    300
ctgtccatca ccatcaggcc caggtactac ggcctggatg tgtggggcca gggcacactg    360
gtgaccgtga gcagcgcttc cacaaccgcg ccatcagtct tccgttggc ccatcatgc     420 gggtcgacga gcggatcgac tgtggccctg gcgtgcttgg tgtcgggata ctttcccgaa    480
cccgtcacgt cagctggaa ctccggatcg cttacgagcg tgtgcatac gttcccctcg      540 gtcttgcaat catcagggct ctactcgctg tcgagcatgg taacggtgcc ctcatcgagg    600
tggccctccg aaacgttcac atgtaacgta gcacatccag cctccaaaac caaggtggat    660
aaacccgtgc cgaaaagaga gaatgggcgg gtgcctcgac cccctgattg ccccaagtgt    720
ccggctccgg aaatgctcgg tggaccctca gtgtttatct tccctccgaa gcccaaggac    780
actctgctga tcgcgcgcac tccagaagta acatgtgtag tggtggcact tgatcccgag    840
gaccccgaag tccagatctc ctggtttgta gatgggaaac agatgcagac cgcaaaaact    900
caacccagag aggagcagtt cgcaggaaca taccgagtgg tatccgtcct tccgattggc    960
caccaggact ggttgaaagg gaagcagttt acgtgtaaag tcaacaataa ggcgttgcct   1020
agccctattg agcggacgat ttcgaaagct aggggacagg cccaccagcc atcggtctat   1080
gtccttccgc cttcccgcga ggagctctcg aagaatacag tgagccttac atgcctcatt   1140
aaggatttct cccgcctga tatcgacgta gagtggcaat caaacggtca acaggagccg   1200
gaatccaagt atagaaccac tccgccccag cttgacgagg acggatcata cttttttgtat   1260 tcaaaactgt cggtggataa gagccggtgg cagagaggtg acaccttcat ctgtgcggtg   1320
atgcacgaag cactccataa tcactacacc aagagagcc tctcgcattc ccccggaaag    1380
```

<210> SEQ ID NO 28
<211> LENGTH: 460
<212> TYPE: PRT
<213> ORGANISM: Artificial Sequence
<220> FEATURE:
<223> OTHER INFORMATION: Canis familiaris plus human

<400> SEQUENCE: 28

```
Glu Val Gln Leu Val Glu Ser Gly Gly Asp Leu Val Lys Pro Gly Gly
1               5                   10                  15

Ser Leu Arg Leu Ser Cys Val Ala Ser Gly Phe Thr Phe Arg Asp Tyr
            20                  25                  30

Ala Met Thr Trp Val Arg Gln Ala Pro Gly Lys Gly Leu Gln Trp Val
        35                  40                  45

Ala Ser Ile Ser Gly Ser Gly Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Asp Arg Leu Ser Ile Thr Ile Arg Pro Arg Tyr Tyr Gly Leu
            100                 105                 110

Asp Val Trp Gly Gln Gly Thr Leu Val Thr Val Ser Ser Ala Ser Thr
        115                 120                 125
```

```
Thr Ala Pro Ser Val Phe Pro Leu Ala Pro Ser Cys Gly Ser Thr Ser
    130                 135                 140
Gly Ser Thr Val Ala Leu Ala Cys Leu Val Ser Gly Tyr Phe Pro Glu
145                 150                 155                 160
Pro Val Thr Val Ser Trp Asn Ser Gly Ser Leu Thr Ser Gly Val His
                165                 170                 175
Thr Phe Pro Ser Val Leu Gln Ser Ser Gly Leu Tyr Ser Leu Ser Ser
            180                 185                 190
Met Val Thr Val Pro Ser Ser Arg Trp Pro Ser Glu Thr Phe Thr Cys
        195                 200                 205
Asn Val Ala His Pro Ala Ser Lys Thr Lys Val Asp Lys Pro Val Pro
210                 215                 220
Lys Arg Glu Asn Gly Arg Val Pro Arg Pro Asp Cys Pro Lys Cys
225                 230                 235                 240
Pro Ala Pro Glu Met Leu Gly Gly Pro Ser Val Phe Ile Phe Pro Pro
                245                 250                 255
Lys Pro Lys Asp Thr Leu Leu Ile Ala Arg Thr Pro Glu Val Thr Cys
            260                 265                 270
Val Val Val Ala Leu Asp Pro Glu Asp Pro Glu Val Gln Ile Ser Trp
        275                 280                 285
Phe Val Asp Gly Lys Gln Met Gln Thr Ala Lys Thr Gln Pro Arg Glu
290                 295                 300
Glu Gln Phe Ala Gly Thr Tyr Arg Val Val Ser Val Leu Pro Ile Gly
305                 310                 315                 320
His Gln Asp Trp Leu Lys Gly Lys Gln Phe Thr Cys Lys Val Asn Asn
                325                 330                 335
Lys Ala Leu Pro Ser Pro Ile Glu Arg Thr Ile Ser Lys Ala Arg Gly
            340                 345                 350
Gln Ala His Gln Pro Ser Val Tyr Val Leu Pro Pro Ser Arg Glu Glu
        355                 360                 365
Leu Ser Lys Asn Thr Val Ser Leu Thr Cys Leu Ile Lys Asp Phe Phe
370                 375                 380
Pro Pro Asp Ile Asp Val Glu Trp Gln Ser Asn Gly Gln Gln Glu Pro
385                 390                 395                 400
Glu Ser Lys Tyr Arg Thr Thr Pro Pro Gln Leu Asp Glu Asp Gly Ser
                405                 410                 415
Tyr Phe Leu Tyr Ser Lys Leu Ser Val Asp Lys Ser Arg Trp Gln Arg
            420                 425                 430
Gly Asp Thr Phe Ile Cys Ala Val Met His Glu Ala Leu His Asn His
        435                 440                 445
Tyr Thr Gln Glu Ser Leu Ser His Ser Pro Gly Lys
450                 455                 460

<210> SEQ ID NO 29
<211> LENGTH: 1380
<212> TYPE: DNA
<213> ORGANISM: Artificial Sequence
<220> FEATURE:
<223> OTHER INFORMATION: Canis familiaris plus human

<400> SEQUENCE: 29
gaggtgcagc tggtggagag cggcggcgat ctggtgaagc tggaggcag cctgagactg      60 agctgcgccg aagcggctt caccttcagg gactacgcca tgacctgggt gagacaggcc    120
cctggaaagg gcctgcagtg ggtgagcagc atctccggca gcggcggcaa cacctactac    180
```

-continued

```
gccgacagcg tgaagggcag gttcaccatc agcagggaca cgccaagaa caccctgtac    240 ctgcagatga acagcctgag ggccgaggac accgccgtgt actactgcgc caaggacaga   300
ctgagcatca ccatcaggcc caggtactac ggcctggacg tgtggggaca gggcacactg   360
gtgaccgtga gcagcgcttc cacaaccgcg ccatcagtct ttccgttggc ccatcatgc    420 gggtcgacga gcggatcgac tgtggccctg gcgtgcttgg tgtcgggata ctttcccgaa   480
cccgtcacgg tcagctggaa ctccggatcg cttacgagcg tgtgcatac gttccctcg    540 gtcttgcaat catcagggct ctactcgctg tcgagcatgg taacggtgcc ctcatcgagg   600
tggccctccg aaacgttcac atgtaacgta gcacatccag cctccaaaac caaggtggat   660 aaaccgtgc cgaaaagaga gaatgggcgg gtgcctcgac ccctgattg ccccaagtgt    720 ccggctccgg aaatgctcgg tggaccctca gtgtttatct tccctccgaa gcccaaggac   780
actctgctga tcgcgcgcac tccagaagta acatgtgtag tggtggcact tgatcccgag   840
gaccccgaag tccagatctc ctggtttgta gatgggaaac agatgcagac cgcaaaaact   900
caacccagag aggagcagtt cgcaggaaca taccgagtgg tatccgtcct tccgattggc   960
caccaggact ggttgaaagg gaagcagttt acgtgtaaag tcaacaataa ggcgttgcct  1020
agccctattg agcggacgat ttcgaaagct aggggacagg cccaccagcc atcggtctat  1080
gtccttccgc cttcccgcga ggagctctcg aagaatacag tgagccttac atgcctcatt  1140
aaggatttct ccccgcctga tatcgacgta gagtggcaat caaacggtca acaggagccg  1200
gaatccaagt atagaaccac tccgccccag cttgacgagg acggatcata cttttttgtat  1260 tcaaaactgt cggtggataa gagccggtgg cagagaggtg acaccttcat ctgtgcggtg  1320
atgcacgaag cactccataa tcactacacc caagagagcc tctcgcattc ccccggaaag  1380
```

<210> SEQ ID NO 30
<211> LENGTH: 460
<212> TYPE: PRT
<213> ORGANISM: Artificial Sequence
<220> FEATURE:
<223> OTHER INFORMATION: Canis familiaris plus human

<400> SEQUENCE: 30

```
Glu Val Gln Leu Val Glu Ser Gly Gly Asp Leu Val Lys Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Gln Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Leu Val Thr Val Ser Ser Ala Ser Thr
        115                 120                 125

Thr Ala Pro Ser Val Phe Pro Leu Ala Pro Ser Cys Gly Ser Thr Ser
    130                 135                 140

Gly Ser Thr Val Ala Leu Ala Cys Leu Val Ser Gly Tyr Phe Pro Glu
145                 150                 155                 160
```

Pro Val Thr Val Ser Trp Asn Ser Gly Ser Leu Thr Ser Gly Val His
             165                 170                 175

Thr Phe Pro Ser Val Leu Gln Ser Ser Gly Leu Tyr Ser Leu Ser Ser
         180                 185                 190

Met Val Thr Val Pro Ser Ser Arg Trp Pro Ser Glu Thr Phe Thr Cys
         195                 200                 205

Asn Val Ala His Pro Ala Ser Lys Thr Lys Val Asp Lys Pro Val Pro
         210                 215                 220

Lys Arg Glu Asn Gly Arg Val Pro Arg Pro Asp Cys Pro Lys Cys
225                 230                 235                 240

Pro Ala Pro Glu Met Leu Gly Gly Pro Ser Val Phe Ile Phe Pro Pro
             245                 250                 255

Lys Pro Lys Asp Thr Leu Leu Ile Ala Arg Thr Pro Glu Val Thr Cys
             260                 265                 270

Val Val Val Ala Leu Asp Pro Glu Asp Pro Glu Val Gln Ile Ser Trp
             275                 280                 285

Phe Val Asp Gly Lys Gln Met Gln Thr Ala Lys Thr Gln Pro Arg Glu
             290                 295                 300

Glu Gln Phe Ala Gly Thr Tyr Arg Val Val Ser Val Leu Pro Ile Gly
305                 310                 315                 320

His Gln Asp Trp Leu Lys Gly Lys Gln Phe Thr Cys Lys Val Asn Asn
                 325                 330                 335

Lys Ala Leu Pro Ser Pro Ile Glu Arg Thr Ile Ser Lys Ala Arg Gly
             340                 345                 350

Gln Ala His Gln Pro Ser Val Tyr Val Leu Pro Pro Ser Arg Glu Glu
             355                 360                 365

Leu Ser Lys Asn Thr Val Ser Leu Thr Cys Leu Ile Lys Asp Phe Phe
370                 375                 380

Pro Pro Asp Ile Asp Val Glu Trp Gln Ser Asn Gly Gln Gln Glu Pro
385                 390                 395                 400

Glu Ser Lys Tyr Arg Thr Thr Pro Pro Gln Leu Asp Glu Asp Gly Ser
             405                 410                 415

Tyr Phe Leu Tyr Ser Lys Leu Ser Val Asp Lys Ser Arg Trp Gln Arg
             420                 425                 430

Gly Asp Thr Phe Ile Cys Ala Val Met His Glu Ala Leu His Asn His
             435                 440                 445

Tyr Thr Gln Glu Ser Leu Ser His Ser Pro Gly Lys
450                 455                 460

<210> SEQ ID NO 31
<211> LENGTH: 1380
<212> TYPE: DNA
<213> ORGANISM: Artificial Sequence
<220> FEATURE:
<223> OTHER INFORMATION: Canis familiaris plus human

<400> SEQUENCE: 31
gaggtgcagc tggtggagag cggcggcgat ctggtgaagc tggcggaag cctgagactg     60 agctgtgccg gcagcggctt caccttcagg gactacgcca tgacctgggt gagacaggcc    120
cctggcaaag gcctggagtg ggtgagcagc atcagcggca gcggcggcaa cacctactac    180
gccgacagcg tgaagggcag gttcaccatc tccagggaca acagcaagaa caccctgtac    240
ctgcagatga acagcctgag ggccgaggat accgccgtgt actactgcgc caaggacaga    300
ctgagcatca ccatcaggcc caggtactac ggactggatg tgtggggcca gggcacctc     360

```
gtgaccgtgt ccagcgcttc cacaaccgcg ccatcagtct ttccgttggc cccatcatgc    420
gggtcgacga gcggatcgac tgtggccctg gcgtgcttgg tgtcgggata ctttcccgaa    480
cccgtcacgg tcagctggaa ctccggatcg cttacgagcg tgtgcatac gttcccctcg     540 gtcttgcaat catcagggct ctactcgctg tcgagcatgg taacggtgcc ctcatcgagg    600
tggccctccg aaacgttcac atgtaacgta gcacatccag cctccaaaac caaggtggat    660
aaacccgtgc cgaaaagaga gaatgggcgg gtgcctcgac cccctgattg ccccaagtgt    720
ccggctccgg aaatgctcgg tggaccctca gtgtttatct tccctccgaa gcccaaggac    780
actctgctga tcgcgcgcac tccagaagta acatgtgtag tggtggcact tgatcccgag    840
gaccccgaag tccagatctc ctggtttgta gatgggaaac agatgcagac cgcaaaaact    900
caacccagag aggagcagtt cgcaggaaca taccgagtgg tatccgtcct tccgattggc    960
caccaggact ggttgaaagg gaagcagttt acgtgtaaag tcaacaataa ggcgttgcct   1020
agccctattg agcggacgat ttcgaaagct aggggacagg cccaccagcc atcggtctat   1080
gtccttccgc cttccgcgga ggagctctcg aagaatacag tgagccttac atgcctcatt   1140
aaggatttct tcccgcctga tatcgacgta gagtggcaat caaacggtca acaggagccg   1200
gaatccaagt atagaaccac tccgccccag cttgacgagg acggatcata cttttttgtat  1260 tcaaaactgt cggtggataa gagccggtgg cagagaggtg acaccttcat ctgtgcggtg   1320
atgcacgaag cactccataa tcactacacc caagagagcc tctcgcattc ccccggaaag   1380
```

<210> SEQ ID NO 32
<211> LENGTH: 460
<212> TYPE: PRT
<213> ORGANISM: Artificial Sequence
<220> FEATURE:
<223> OTHER INFORMATION: Canis familiaris plus human

<400> SEQUENCE: 32

```
Glu Val Gln Leu Val Glu Ser Gly Gly Asp Leu Val Lys Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Leu Val Thr Val Ser Ser Ala Ser Thr
        115                 120                 125

Thr Ala Pro Ser Val Phe Pro Leu Ala Pro Ser Cys Gly Ser Thr Ser
    130                 135                 140

Gly Ser Thr Val Ala Leu Ala Cys Leu Val Gly Tyr Phe Pro Glu
145                 150                 155                 160

Pro Val Thr Val Ser Trp Asn Ser Gly Ser Leu Thr Ser Gly Val His
                165                 170                 175

Thr Phe Pro Ser Val Leu Gln Ser Ser Gly Leu Tyr Ser Leu Ser Ser
```

|  | 180 |  |  |  | 185 |  |  |  | 190 |  |  |
|---|---|---|---|---|---|---|---|---|---|---|---|

Met Val Thr Val Pro Ser Ser Arg Trp Pro Ser Glu Thr Phe Thr Cys
        195                 200                 205

Asn Val Ala His Pro Ala Ser Lys Thr Lys Val Asp Lys Pro Val Pro
        210                 215                 220

Lys Arg Glu Asn Gly Arg Val Pro Arg Pro Asp Cys Pro Lys Cys
225                 230                 235                 240

Pro Ala Pro Glu Met Leu Gly Gly Pro Ser Val Phe Ile Phe Pro Pro
                245                 250                 255

Lys Pro Lys Asp Thr Leu Leu Ile Ala Arg Thr Pro Glu Val Thr Cys
                260                 265                 270

Val Val Val Ala Leu Asp Pro Glu Asp Pro Glu Val Gln Ile Ser Trp
        275                 280                 285

Phe Val Asp Gly Lys Gln Met Gln Thr Ala Lys Thr Gln Pro Arg Glu
        290                 295                 300

Glu Gln Phe Ala Gly Thr Tyr Arg Val Val Ser Val Leu Pro Ile Gly
305                 310                 315                 320

His Gln Asp Trp Leu Lys Gly Lys Gln Phe Thr Cys Lys Val Asn Asn
                325                 330                 335

Lys Ala Leu Pro Ser Pro Ile Glu Arg Thr Ile Ser Lys Ala Arg Gly
                340                 345                 350

Gln Ala His Gln Pro Ser Val Tyr Val Leu Pro Pro Ser Arg Glu Glu
        355                 360                 365

Leu Ser Lys Asn Thr Val Ser Leu Thr Cys Leu Ile Lys Asp Phe Phe
        370                 375                 380

Pro Pro Asp Ile Asp Val Glu Trp Gln Ser Asn Gly Gln Gln Glu Pro
385                 390                 395                 400

Glu Ser Lys Tyr Arg Thr Thr Pro Pro Gln Leu Asp Glu Asp Gly Ser
                405                 410                 415

Tyr Phe Leu Tyr Ser Lys Leu Ser Val Asp Lys Ser Arg Trp Gln Arg
                420                 425                 430

Gly Asp Thr Phe Ile Cys Ala Val Met His Glu Ala Leu His Asn His
        435                 440                 445

Tyr Thr Gln Glu Ser Leu Ser His Ser Pro Gly Lys
        450                 455                 460

<210> SEQ ID NO 33
<211> LENGTH: 669
<212> TYPE: DNA
<213> ORGANISM: Artificial Sequence
<220> FEATURE:
<223> OTHER INFORMATION: Canis familiaris plus human

<400> SEQUENCE: 33
gacattgtga tgacccagac ccctctgagc ctgtccgtga gccctggcga gcctgctagc      60
atcagctgca ggagcagcca gagcctgctg tacagcatcg ctacaactac ctggactgg     120 ttcaggcaga agcccggcca gagccctcag aggctgatct acctgggaag caacagggcc    180
agcggcgtgc ctgacaggtt tagcggcagc ggcagcggca ccgatttcac cctgaggatc    240
agcagagtgg aggccgatga cgccggcgtg tactactgca tgcaggccct gcagaccccc    300
tacaccttcg gccagggcac caaggtggag atcaagagga cgacgctca gccagccgtg    360 tacctcttcc agccttcgcc ggaccagctt catacggggt cagcgtcggt ggtgtgcctg    420
ttgaactcgt ttaccccccaa ggacattaac gtgaagtgga aggtagacgg ggtaattcaa    480

```
gacactggca ttcaagagtc cgtcacggaa caagactcaa aagactcaac gtattcactg      540
tcgtcaacct tgacgatgtc aagcaccgag tatcttagcc atgagctgta ttcgtgcgag      600
atcacccaca agtccctccc ctccactctt atcaaatcct ttcagcggtc ggaatgtcag      660
cgggtcgat                                                              669
```

<210> SEQ ID NO 34
<211> LENGTH: 223
<212> TYPE: PRT
<213> ORGANISM: Artificial Sequence
<220> FEATURE:
<223> OTHER INFORMATION: Canis familiaris plus human

<400> SEQUENCE: 34

```
Asp Ile Val Met Thr Gln Thr Pro Leu Ser Leu Ser Val Ser Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Phe Arg Gln Lys Pro Gly Gln Ser
        35                  40                  45

Pro Gln Arg Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Asp Ala Gly Val Tyr Tyr Cys Met Gln Ala
                85                  90                  95

Leu Gln Thr Pro Tyr Thr Phe Gly Gln Gly Thr Lys Val Glu Ile Lys
            100                 105                 110

Arg Asn Asp Ala Gln Pro Ala Val Tyr Leu Phe Gln Pro Ser Pro Asp
        115                 120                 125

Gln Leu His Thr Gly Ser Ala Ser Val Val Cys Leu Leu Asn Ser Phe
    130                 135                 140

Tyr Pro Lys Asp Ile Asn Val Lys Trp Lys Val Asp Gly Val Ile Gln
145                 150                 155                 160

Asp Thr Gly Ile Gln Glu Ser Val Thr Glu Gln Asp Ser Lys Asp Ser
                165                 170                 175

Thr Tyr Ser Leu Ser Ser Thr Leu Thr Met Ser Ser Thr Glu Tyr Leu
            180                 185                 190

Ser His Glu Leu Tyr Ser Cys Glu Ile Thr His Lys Ser Leu Pro Ser
        195                 200                 205

Thr Leu Ile Lys Ser Phe Gln Arg Ser Glu Cys Gln Arg Val Asp
    210                 215                 220
```

<210> SEQ ID NO 35
<211> LENGTH: 669
<212> TYPE: DNA
<213> ORGANISM: Artificial Sequence
<220> FEATURE:
<223> OTHER INFORMATION: Canis familiaris plus human

<400> SEQUENCE: 35

```
gacatcgtga tgacccagac ccctctgagc ctgagcgtga gccctggaga gcccgccagc      60
atctcctgca gaagcagcca gagcctgctg tacagcatcg gctacaacta cctggactgg     120
tacctgcaga agcccggcca gagccctcag ctgctgatct acctgggcag caacagagcc     180
agcggcgtgc ctgacagatt tagcggcagc ggcagcggca cagacttcac cctgaggatc     240
agcagagtgg aggccgacga tgccggcgtg tactactgca tgcaggccct gcagaccccc     300
```

```
tacaccttcg gccagggcac caaggtggag atcaagagga cgacgctca gccagccgtg    360 tacctcttcc agccttcgcc ggaccagctt catacggggt cagcgtcggt ggtgtgcctg    420
ttgaactcgt tttaccccaa ggacattaac gtgaagtgga aggtagacgg ggtaattcaa    480
gacactggca ttcaagagtc cgtcacggaa caagactcaa aagactcaac gtattcactg    540
tcgtcaacct tgacgatgtc aagcaccgag tatcttagcc atgagctgta ttcgtgcgag    600
atcacccaca agtccctccc ctccactctt atcaaatcct ttcagcggtc ggaatgtcag    660
cgggtcgat                                                            669
```

```
<210> SEQ ID NO 36
<211> LENGTH: 223
<212> TYPE: PRT
<213> ORGANISM: Artificial Sequence
<220> FEATURE:
<223> OTHER INFORMATION: Canis familiaris plus human

<400> SEQUENCE: 36

Asp Ile Val Met Thr Gln Thr Pro Leu Ser Leu Ser Val Ser Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Asp Asp Ala Gly Val Tyr Tyr Cys Met Gln Ala
                85                  90                  95

Leu Gln Thr Pro Tyr Thr Phe Gly Gln Gly Thr Lys Val Glu Ile Lys
            100                 105                 110

Arg Asn Asp Ala Gln Pro Ala Val Tyr Leu Phe Gln Pro Ser Pro Asp
        115                 120                 125

Gln Leu His Thr Gly Ser Ala Ser Val Val Cys Leu Leu Asn Ser Phe
    130                 135                 140

Tyr Pro Lys Asp Ile Asn Val Lys Trp Lys Val Asp Gly Val Ile Gln
145                 150                 155                 160

Asp Thr Gly Ile Gln Glu Ser Val Thr Glu Gln Asp Ser Lys Asp Ser
                165                 170                 175

Thr Tyr Ser Leu Ser Ser Thr Leu Thr Met Ser Ser Thr Glu Tyr Leu
            180                 185                 190

Ser His Glu Leu Tyr Ser Cys Glu Ile Thr His Lys Ser Leu Pro Ser
        195                 200                 205

Thr Leu Ile Lys Ser Phe Gln Arg Ser Glu Cys Gln Arg Val Asp
    210                 215                 220
```

```
<210> SEQ ID NO 37
<211> LENGTH: 669
<212> TYPE: DNA
<213> ORGANISM: Artificial Sequence
<220> FEATURE:
<223> OTHER INFORMATION: Canis familiaris plus human

<400> SEQUENCE: 37
gacatcgtga tgacccagac acccctgagc ctgagcgtga gccctggcga acctgccagc    60
```

```
atcagctgca ggagctccca gagcctgctg tacagcatcg gctacaacta cctcgactgg     120
tacctgcaga agcccggcca gagccctcag ctgctgatct acctgggctc aacagagcc      180 agcggcgtgc ctgacagatt tagcggcagc ggcagcggaa ccgacttcac cctgaggatc     240
agcagagtgg aggccgacga cgccggcttc tactactgca tgcaggccct gcagaccccc     300
tacaccttcg gccagggcac caagctggag atcaagagga cgacgctca gccagccgtg      360 tacctcttcc agccttcgcc ggaccagctt catacggggt cagcgtcggt ggtgtgcctg     420
ttgaactcgt tttaccccaa ggacattaac gtgaagtgga aggtagacgg ggtaattcaa     480
gacactggca ttcaagagtc cgtcacggaa caagactcaa aagactcaac gtattcactg     540
tcgtcaacct tgacgatgtc aagcaccgag tatcttagcc atgagctgta ttcgtgcgag     600
atcacccaca gtccctccc ctccactctt atcaaatcct ttcagcggtc ggaatgtcag      660
cgggtcgat                                                            669
```

<210> SEQ ID NO 38
<211> LENGTH: 223
<212> TYPE: PRT
<213> ORGANISM: Artificial Sequence
<220> FEATURE:
<223> OTHER INFORMATION: Canis familiaris plus human

<400> SEQUENCE: 38

```
Asp Ile Val Met Thr Gln Thr Pro Leu Ser Leu Ser Val Ser Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Asp Asp Ala Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Asn Asp Ala Gln Pro Ala Val Tyr Leu Phe Gln Pro Ser Pro Asp
        115                 120                 125

Gln Leu His Thr Gly Ser Ala Ser Val Val Cys Leu Leu Asn Ser Phe
    130                 135                 140

Tyr Pro Lys Asp Ile Asn Val Lys Trp Lys Val Asp Gly Val Ile Gln
145                 150                 155                 160

Asp Thr Gly Ile Gln Glu Ser Val Thr Glu Gln Asp Ser Lys Asp Ser
                165                 170                 175

Thr Tyr Ser Leu Ser Ser Thr Leu Thr Met Ser Ser Thr Glu Tyr Leu
            180                 185                 190

Ser His Glu Leu Tyr Ser Cys Glu Ile Thr His Lys Ser Leu Pro Ser
        195                 200                 205

Thr Leu Ile Lys Ser Phe Gln Arg Ser Glu Cys Gln Arg Val Asp
    210                 215                 220
```

<210> SEQ ID NO 39
<211> LENGTH: 21
<212> TYPE: PRT
<213> ORGANISM: Canis familiaris

<400> SEQUENCE: 39

Gln Trp Lys Met Asp His Pro Thr Asn Cys Ser Ala Glu Leu Arg Leu
1               5                   10                  15

Ser Tyr Gln Leu Asp
            20

<210> SEQ ID NO 40
<211> LENGTH: 11
<212> TYPE: PRT
<213> ORGANISM: Canis familiaris

<400> SEQUENCE: 40

Arg Leu Ala Ala Ser Thr Leu Lys Ser Gly Ala
1               5                   10

<210> SEQ ID NO 41
<211> LENGTH: 11
<212> TYPE: PRT
<213> ORGANISM: Canis familiaris

<400> SEQUENCE: 41

Thr Asn Cys Ser Ala Glu Leu Arg Leu Ser Tyr
1               5                   10

<210> SEQ ID NO 42
<211> LENGTH: 4
<212> TYPE: PRT
<213> ORGANISM: Canis familiaris

<400> SEQUENCE: 42

Ser Thr Leu Lys
1

<210> SEQ ID NO 43
<211> LENGTH: 16
<212> TYPE: PRT
<213> ORGANISM: Homo sapiens

<400> SEQUENCE: 43

Arg Ser Ser Gln Ser Leu Leu Tyr Ser Ile Gly Tyr Asn Tyr Leu Asp
1               5                   10                  15

<210> SEQ ID NO 44
<211> LENGTH: 7
<212> TYPE: PRT
<213> ORGANISM: Homo sapiens

<400> SEQUENCE: 44

Leu Gly Ser Asn Arg Ala Ser
1               5

<210> SEQ ID NO 45
<211> LENGTH: 9
<212> TYPE: PRT
<213> ORGANISM: Homo sapiens

<400> SEQUENCE: 45

Met Gln Ala Leu Gln Thr Pro Tyr Thr
1               5

<210> SEQ ID NO 46
<211> LENGTH: 5
<212> TYPE: PRT

<213> ORGANISM: Homo sapiens

<400> SEQUENCE: 46

Asp Tyr Ala Met Thr
1               5

<210> SEQ ID NO 47
<211> LENGTH: 17
<212> TYPE: PRT
<213> ORGANISM: Homo sapiens

<400> SEQUENCE: 47

Ser Ile Ser Gly Ser Gly Gly Asn Thr Tyr Tyr Ala Asp Ser Val Lys
1               5                   10                  15

Gly

<210> SEQ ID NO 48
<211> LENGTH: 16
<212> TYPE: PRT
<213> ORGANISM: Homo sapiens

<400> SEQUENCE: 48

Asp Arg Leu Ser Ile Thr Ile Arg Pro Arg Tyr Gly Leu Asp Val
1               5                   10                  15

<210> SEQ ID NO 49
<211> LENGTH: 13
<212> TYPE: PRT
<213> ORGANISM: Homo sapiens

<400> SEQUENCE: 49

Ser Gly Gly Gly Ser Ser Ile Gly Gln Ser Tyr Val Ser
1               5                   10

<210> SEQ ID NO 50
<211> LENGTH: 7
<212> TYPE: PRT
<213> ORGANISM: Homo sapiens

<400> SEQUENCE: 50

Asp Asn Asn Lys Arg Pro Ser
1               5

<210> SEQ ID NO 51
<211> LENGTH: 12
<212> TYPE: PRT
<213> ORGANISM: Homo sapiens

<400> SEQUENCE: 51

Gly Thr Trp Asp Thr Ser Pro Val Trp Glu Trp Pro
1               5                   10

<210> SEQ ID NO 52
<211> LENGTH: 5
<212> TYPE: PRT
<213> ORGANISM: Homo sapiens

<400> SEQUENCE: 52

Ser Tyr Tyr Met His
1               5

<210> SEQ ID NO 53
<211> LENGTH: 17
<212> TYPE: PRT

<213> ORGANISM: Homo sapiens

<400> SEQUENCE: 53

Ile Ile Asn Pro Arg Gly Gly Ser Thr Ser Tyr Ala Gln Lys Phe Gln
1               5                   10                  15

Gly

<210> SEQ ID NO 54
<211> LENGTH: 7
<212> TYPE: PRT
<213> ORGANISM: Homo sapiens

<400> SEQUENCE: 54

Gly Lys Tyr Trp Met Tyr Asp
1               5

<210> SEQ ID NO 55
<211> LENGTH: 12
<212> TYPE: PRT
<213> ORGANISM: Homo sapiens

<400> SEQUENCE: 55

Arg Ala Ser Gln Ser Val Ser Ser Ser Tyr Leu Ala
1               5                   10

<210> SEQ ID NO 56
<211> LENGTH: 7
<212> TYPE: PRT
<213> ORGANISM: Homo sapiens

<400> SEQUENCE: 56

Gly Ala Ser Ser Arg Ala Thr
1               5

<210> SEQ ID NO 57
<211> LENGTH: 10
<212> TYPE: PRT
<213> ORGANISM: Homo sapiens

<400> SEQUENCE: 57

Gln Gln Tyr Gly Ser Ser Pro Pro Trp Thr
1               5                   10

<210> SEQ ID NO 58
<211> LENGTH: 5
<212> TYPE: PRT
<213> ORGANISM: Homo sapiens

<400> SEQUENCE: 58

Arg Asn Ala Met Phe
1               5

<210> SEQ ID NO 59
<211> LENGTH: 16
<212> TYPE: PRT
<213> ORGANISM: Homo sapiens

<400> SEQUENCE: 59

Leu Ile Gly Thr Gly Gly Ala Thr Asn Tyr Ala Asp Ser Val Lys Gly
1               5                   10                  15

<210> SEQ ID NO 60
<211> LENGTH: 7
<212> TYPE: PRT

```
<213> ORGANISM: Homo sapiens

<400> SEQUENCE: 60

Gly Arg Tyr Tyr Phe Asp Tyr
1               5

<210> SEQ ID NO 61
<211> LENGTH: 17
<212> TYPE: PRT
<213> ORGANISM: Canis familiaris

<400> SEQUENCE: 61

Phe Asn Glu Cys Arg Cys Thr Asp Thr Pro Pro Cys Pro Val Pro Glu
1               5                   10                  15

Pro

<210> SEQ ID NO 62
<211> LENGTH: 22
<212> TYPE: PRT
<213> ORGANISM: Canis familiaris

<400> SEQUENCE: 62

Pro Lys Arg Glu Asn Gly Arg Val Pro Arg Pro Pro Asp Cys Pro Lys
1               5                   10                  15

Cys Pro Ala Pro Glu Met
            20

<210> SEQ ID NO 63
<211> LENGTH: 20
<212> TYPE: PRT
<213> ORGANISM: Canis familiaris

<400> SEQUENCE: 63

Ala Lys Glu Cys Glu Cys Lys Cys Asn Cys Asn Asn Cys Pro Cys Pro
1               5                   10                  15

Gly Cys Gly Leu
            20

<210> SEQ ID NO 64
<211> LENGTH: 17
<212> TYPE: PRT
<213> ORGANISM: Artificial Sequence
<220> FEATURE:
<223> OTHER INFORMATION: modified canis famliaris

<400> SEQUENCE: 64

Pro Lys Glu Ser Thr Cys Lys Cys Ile Pro Pro Cys Pro Val Pro Glu
1               5                   10                  15

Ser

<210> SEQ ID NO 65
<211> LENGTH: 13
<212> TYPE: PRT
<213> ORGANISM: Homo sapiens

<400> SEQUENCE: 65

Ser Gly Gly Ser Ser Asn Ile Gly Asn Ser Tyr Val Ser
1               5                   10

<210> SEQ ID NO 66
<211> LENGTH: 7
<212> TYPE: PRT
<213> ORGANISM: Homo sapiens
```

<400> SEQUENCE: 66

Asp Asn Asn Lys Arg Pro Ser
1               5

<210> SEQ ID NO 67
<211> LENGTH: 12
<212> TYPE: PRT
<213> ORGANISM: Homo sapiens

<400> SEQUENCE: 67

Gly Thr Trp Asp Thr Ser Leu Ser Ala Asn Tyr Val
1               5                   10

<210> SEQ ID NO 68
<211> LENGTH: 5
<212> TYPE: PRT
<213> ORGANISM: Homo sapiens

<400> SEQUENCE: 68

Ser Tyr Tyr Met His
1               5

<210> SEQ ID NO 69
<211> LENGTH: 17
<212> TYPE: PRT
<213> ORGANISM: Homo sapiens

<400> SEQUENCE: 69

Ile Ile Asn Pro Ser Gly Gly Ser Thr Ser Tyr Ala Gln Lys Phe Gln
1               5                   10                  15

Gly

<210> SEQ ID NO 70
<211> LENGTH: 7
<212> TYPE: PRT
<213> ORGANISM: Homo sapiens

<400> SEQUENCE: 70

Gly Lys Trp Trp Leu Asp Tyr
1               5

<210> SEQ ID NO 71
<211> LENGTH: 13
<212> TYPE: PRT
<213> ORGANISM: Homo sapiens

<400> SEQUENCE: 71

Ser Gly Gly Ser Ser Asn Ile Gly Asn Ser Tyr Val Ser
1               5                   10

<210> SEQ ID NO 72
<211> LENGTH: 7
<212> TYPE: PRT
<213> ORGANISM: Homo sapiens

<400> SEQUENCE: 72

Asp Asn Asn Lys Arg Pro Ser
1               5

<210> SEQ ID NO 73
<211> LENGTH: 12
<212> TYPE: PRT
<213> ORGANISM: Homo sapiens

<400> SEQUENCE: 73

Gly Thr Trp Asp Thr Ser Thr Thr Met Tyr Pro Leu
1               5                   10

<210> SEQ ID NO 74
<211> LENGTH: 5
<212> TYPE: PRT
<213> ORGANISM: Homo sapiens

<400> SEQUENCE: 74

Ser Tyr Tyr Met His
1               5

<210> SEQ ID NO 75
<211> LENGTH: 17
<212> TYPE: PRT
<213> ORGANISM: Homo sapiens

<400> SEQUENCE: 75

Ile Ile Asn Pro Ser Gly Gly Ser Thr Ser Tyr Ala Gln Lys Phe Gln
1               5                   10                  15

Gly

<210> SEQ ID NO 76
<211> LENGTH: 7
<212> TYPE: PRT
<213> ORGANISM: Homo sapiens

<400> SEQUENCE: 76

Gly Lys Trp Trp Phe Tyr Asp
1               5

<210> SEQ ID NO 77
<211> LENGTH: 11
<212> TYPE: PRT
<213> ORGANISM: Homo sapiens

<400> SEQUENCE: 77

Arg Ala Ser Gln Ser Val Ser Ser Tyr Leu Ala
1               5                   10

<210> SEQ ID NO 78
<211> LENGTH: 7
<212> TYPE: PRT
<213> ORGANISM: Homo sapiens

<400> SEQUENCE: 78

His Ala Ser Asn Arg Ala Thr
1               5

<210> SEQ ID NO 79
<211> LENGTH: 9
<212> TYPE: PRT
<213> ORGANISM: Homo sapiens

<400> SEQUENCE: 79

Gln Gln Arg Ser Asn Trp Pro Leu Thr
1               5

<210> SEQ ID NO 80
<211> LENGTH: 5
<212> TYPE: PRT
<213> ORGANISM: Homo sapiens

<400> SEQUENCE: 80

Asn Phe Val Met His
1               5

<210> SEQ ID NO 81
<211> LENGTH: 16
<212> TYPE: PRT
<213> ORGANISM: Homo sapiens

<400> SEQUENCE: 81

Ala Ile Gly Thr Gly Gly Gly Thr Tyr Tyr Ala Asp Ser Val Lys Gly
1               5                   10                  15

<210> SEQ ID NO 82
<211> LENGTH: 15
<212> TYPE: PRT
<213> ORGANISM: Homo sapiens

<400> SEQUENCE: 82

Asp Arg Pro Met Val Arg Gly Val Ile Ile Asp Tyr Phe Asp Tyr
1               5                   10                  15

<210> SEQ ID NO 83
<211> LENGTH: 12
<212> TYPE: PRT
<213> ORGANISM: Homo sapiens

<400> SEQUENCE: 83

Arg Ala Ser Gln Ser Val Ser Ser Ser Tyr Leu Ala
1               5                   10

<210> SEQ ID NO 84
<211> LENGTH: 7
<212> TYPE: PRT
<213> ORGANISM: Homo sapiens

<400> SEQUENCE: 84

Gly Ala Ser Ser Arg Ala Thr
1               5

<210> SEQ ID NO 85
<211> LENGTH: 10
<212> TYPE: PRT
<213> ORGANISM: Homo sapiens

<400> SEQUENCE: 85

Gln Gln Tyr Gly Ser Ser Pro Pro Trp Thr
1               5                   10

<210> SEQ ID NO 86
<211> LENGTH: 5
<212> TYPE: PRT
<213> ORGANISM: Homo sapiens

<400> SEQUENCE: 86

Arg Tyr Gly Met His
1               5

<210> SEQ ID NO 87
<211> LENGTH: 17
<212> TYPE: PRT
<213> ORGANISM: Homo sapiens

<400> SEQUENCE: 87

```
Ile Ile Trp Phe Glu Gly Asn Asn Gln Tyr Tyr Ala Asp Ser Val Lys
1               5                   10                  15

Gly

<210> SEQ ID NO 88
<211> LENGTH: 7
<212> TYPE: PRT
<213> ORGANISM: Homo sapiens

<400> SEQUENCE: 88

Gly Lys Tyr Tyr Phe Asp Tyr
1               5

<210> SEQ ID NO 89
<211> LENGTH: 11
<212> TYPE: PRT
<213> ORGANISM: Homo sapiens

<400> SEQUENCE: 89

Arg Ala Ser Gln Gly Ile Ser Thr Trp Leu Ala
1               5                   10

<210> SEQ ID NO 90
<211> LENGTH: 7
<212> TYPE: PRT
<213> ORGANISM: Homo sapiens

<400> SEQUENCE: 90

Val Ala Ser Ser Leu Gln Ser
1               5

<210> SEQ ID NO 91
<211> LENGTH: 9
<212> TYPE: PRT
<213> ORGANISM: Homo sapiens

<400> SEQUENCE: 91

Gln Gln Ala Asn Ser Phe Pro Phe Thr
1               5

<210> SEQ ID NO 92
<211> LENGTH: 5
<212> TYPE: PRT
<213> ORGANISM: Homo sapiens

<400> SEQUENCE: 92

Ser Tyr Ala Met Ser
1               5

<210> SEQ ID NO 93
<211> LENGTH: 17
<212> TYPE: PRT
<213> ORGANISM: Homo sapiens

<400> SEQUENCE: 93

Ser Ile Thr Gly Ser Gly Gly Ser Thr Tyr Tyr Ala Asp Ser Val Lys
1               5                   10                  15

Gly

<210> SEQ ID NO 94
<211> LENGTH: 8
<212> TYPE: PRT
<213> ORGANISM: Homo sapiens
```

```
<400> SEQUENCE: 94

Asp Asn Arg Gly Phe Phe His Tyr
1               5
```